(12) United States Patent
Bourget et al.

(10) Patent No.: US 7,060,441 B2
(45) Date of Patent: Jun. 13, 2006

(54) METHOD FOR FRAGMENTING AND LABELING DNA INVOLVING ABASIC SITES AND PHOSPHATE LABELING

(75) Inventors: Cecile Bourget, Grenoble (FR); Mitsuharu Kotera, Meylan (FR); Jean Lhomme, Meylan (FR); Emmanuelle Trevisiol, Cornebarrieu (FR); Ali Laayoun, Lyons (FR); Christelle Tora, Oytier Saint-Oblas (FR); Isabelle Sothier, Genay (FR)

(73) Assignees: Biomerieux, Marcy l'etoile (FR); Universite Joseph Fourier, Grenoble (FR); Centre National de la Recherche Scientifique, Paris (FR)

( * ) Notice: Subject to any disclaimer, the term of this patent is extended or adjusted under 35 U.S.C. 154(b) by 681 days.

(21) Appl. No.: 10/137,460

(22) Filed: May 3, 2002

(65) Prior Publication Data

US 2003/0143555 A1    Jul. 31, 2003

Related U.S. Application Data

(60) Provisional application No. 60/310,273, filed on Aug. 7, 2001.

(30) Foreign Application Priority Data

May 4, 2001   (FR) .................................. 01 06039

(51) Int. Cl.
*C12Q 1/68*   (2006.01)
*C12P 19/34*   (2006.01)

(52) U.S. Cl. ........................... 435/6; 435/91.2; 436/94
(58) Field of Classification Search .................... 435/6, 435/91.2; 436/94
See application file for complete search history.

(56) References Cited

U.S. PATENT DOCUMENTS

| | | | |
|---|---|---|---|
| 4,683,195 A | | 7/1987 | Mullis et al. |
| 4,683,202 A | | 7/1987 | Mullis |
| 4,800,159 A | | 1/1989 | Mullis et al. |
| 5,328,824 A | | 7/1994 | Ward et al. |
| 5,449,767 A | | 9/1995 | Ward et al. |
| 6,489,114 B1 | * | 12/2002 | Laayoun et al. ................ 435/6 |
| 6,818,398 B1 | * | 11/2004 | Bavykin et al. ................ 435/6 |
| 2002/0081586 A1 | * | 6/2002 | Laayoun et al. ................ 435/6 |
| 2004/0005614 A1 | * | 1/2004 | Kurn et al. .................... 435/6 |

FOREIGN PATENT DOCUMENTS

| | | |
|---|---|---|
| DE | 39 10 151 A1 | 10/1990 |
| EP | 0 063 879 A2 | 11/1982 |
| EP | 0 097 373 A2 | 1/1984 |
| EP | 0 201 184 A2 | 12/1986 |
| EP | 0 286 898 A2 | 10/1988 |
| EP | 0 302 175 A2 | 2/1989 |
| EP | 0 329 198 A2 | 8/1989 |
| EP | 0 567 841 A2 | 11/1993 |
| EP | 0 569 272 A1 | 11/1993 |
| FR | 2 607 507 A1 | 6/1988 |
| WO | WO 90/01069 A1 | 2/1990 |
| WO | WO 93/16094 A2 | 8/1993 |
| WO | WO 95/08000 A2 | 3/1995 |
| WO | WO 98/05766 A1 | 2/1998 |
| WO | WO 99/65926 A1 | 12/1999 |
| WO | WO 00/07982 A1 | 2/2000 |
| WO | WO 00/40590 A2 | 7/2000 |
| WO | WO 01/44506 A1 | 6/2001 |
| WO | WO 01/92361 A1 | 12/2001 |

* cited by examiner

*Primary Examiner*—Kenneth R. Horlick
(74) *Attorney, Agent, or Firm*—Oliff & Berridge, PLC

(57) ABSTRACT

A single- or double-stranded deoxyribonucleic acid (DNA) is fragmented and labeled by chemically fragmenting the DNA by creating at least one abasic site on the DNA, and attaching a marker to at least one of the fragments by means of a labeling reagent, the reagent covalently and predominantly coupling to at least one phosphate of the fragment. This method can be applied in the field of diagnosis.

31 Claims, 21 Drawing Sheets

DPDAM
(DiPhenylIDAM)

PMDAM
(PhenylMethylDAM)

NPDAM
(NitroPhenylIDAM)

PDAM
(PyrenylDiAzoMethane)

BioDPDAM
(BiotinylDPDAM)

m-BioPMDAM
(meta-BiotinylPMDAM)

p-BioPMDAM
(para-BiotinylPMDAM)

o-BioPMDAM
(ortho-BiotinylPMDAM)

Cy5PMDAM

Fig. 5A
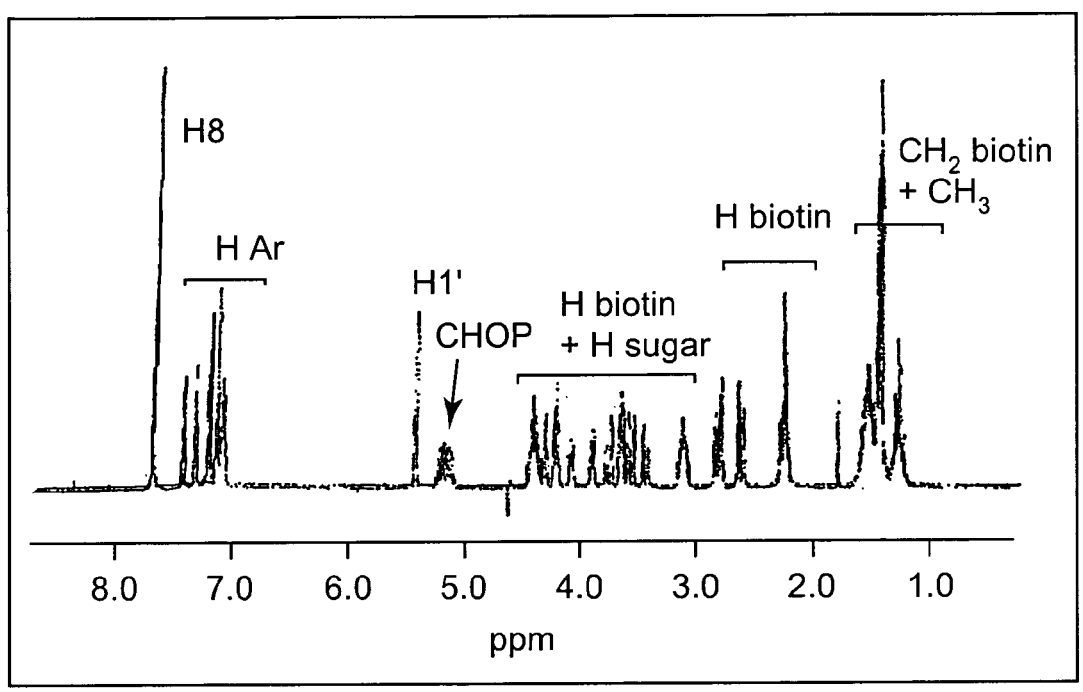
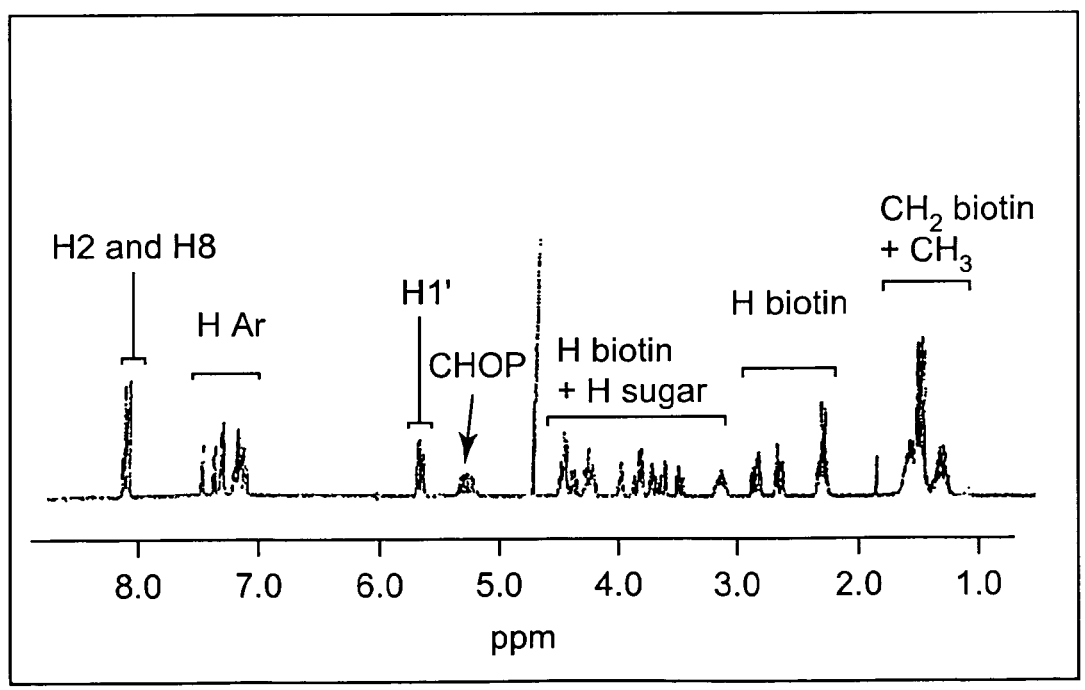
Fig. 5B

METHOD FOR FRAGMENTING AND LABELING DNA INVOLVING ABASIC SITES AND PHOSPHATE LABELING

This application claims the benefit of Provisional application Ser. No. 60/310,273, filed Aug. 7, 2001

BACKGROUND OF THE INVENTION

The present invention relates to a method for fragmenting and labeling DNA and to the applications of this method, in particular in the field of diagnosis.

DESCRIPTION OF THE PRIOR ART

The prior art shows that numerous methods exist for labeling nucleic acids.

A first method consists in attaching the marker to the base, whether the latter is a natural base or a modified base. A second method proposes attaching the marker to the sugar, here again whether it is a natural sugar or a modified sugar. A third method is aimed at attaching the marker to the phosphate.

Labeling on the base has been used in particular in the approach for labeling nucleic acids by incorporating directly labeled nucleotides.

Labeling on the sugar is often used in the case of the oligonucleotides prepared by chemical synthesis.

Labeling on the phosphate has also been used to introduce arms which have been functionalized and markers during the chemical synthesis of oligonucleotides.

In fact, persons skilled in the art, who have to carry out a labeling of a nucleotide, or of a nucleotide analog or of a nucleic acid, are inclined to carry out this attachment onto the base or onto the sugar which offer them more convenience and alternatives. That is in fact what emerges from the study of numerous documents, such as EP-A-0,329,198, EP-A-0,302,175, EP-A-0,097,373, EP-A-0,063,879, U.S. Pat. No. 5,449,767, U.S. Pat. No. 5,328,824, WO-A-93/16094, DE-A-3,910,151, EP-A-0,567,841 for the base or EP-A-0,286,898 for the sugar.

The attachment of the marker to the phosphate is a technique which is more complex than the technique consisting in functionalizing the base or the sugar and has been used a lot less in particular because of the low reactivity of the phosphate (see for example Jencks W. P. et al., J. Amer. Chem. Soc., 82, 1778–1785, 1960). Likewise, in the review by O'Donnel and McLaughlin ("Reporter groups for the analysis of nucleic acid structure", p. 216–243, in "Bioorganic Chemistry: Nucleic Acids", Ed. Hecht S. M., Oxford University Press, 1996) relating to the methods for introducing probes into oligonucleotide fragments, the effective alkylation of the internucleotide phosphodiester is considered as being impossible.

A second problem exists for the labeling of nucleic acids especially for large-size nucleic acids, that is to say of more than one hundred (100) nucleotides, which have to hybridize with nucleic probes. This problem is linked to steric hindrance or to the lack of specificity between the nucleic acid and the nucleic probe. This results in a loss of sensitivity in detection.

Steric hindrance may be the result not only of the length of the nucleic acid, but also of the existence or of the preservation of secondary structures. Fragmentation makes it possible to destroy these structures and thus to optimize the hybridization. This steric hindrance plays a particularly important role in the case of hybridization on surfaces containing capture probes in high density, for example the DNA chips developed by the company Affymetrix ("Accessing Genetic Information with High-Density DNA arrays", M. Shee et al., Science, 274, 610–614. "Light-generated oligonucleotide arrays for rapid DNA sequence analysis", A. Caviani Pease et al., Proc. Natl. Acad. Sci. USA, 1994, 91, 5022–5026).

As regards the fragmentation of nucleic acids, numerous methods are described in the state of the art.

Firstly, the fragmentation may be enzymatic, that is to say that the fragmentation of the nucleic acids may be carried out by nucleases (DNases).

Secondly, the fragmentation may be chemical. For example, in the case of DNA, it is possible to carry out the depurination or the depyrimidination of the DNA, which is then fragmented in the presence of a base by a so-called "β-elimination" mechanism. The fragmentation of the DNA may be carried out by mechanisms of oxidation, alkylation, and addition of free radicals, among others.

Finally, the fragmentation may be physical, for example by sonication or by a photochemical route.

The difficulty consists in fact in combining these two steps of fragmentation and labeling.

Patent application WO-A-99/65926 describes a method for labeling a synthetic or natural ribonucleic acid (RNA) which consists in fragmenting the RNA and in labeling at the level of the terminal phosphate. This document describes a number of reactive functional groups which can be used for labeling in conjunction with fragmentation. These functional groups make it possible to label RNAs, but a fragmentation step has to be associated in order to have effective labeling because this labeling occurs on the phosphate released during fragmentation. Furthermore, it is necessary to add a large excess of labeling reagent relative to the RNA in order to obtain effective labeling, which induces problems of background noise generated by the marker in excess. Finally, this method is not applicable to double-stranded DNA.

A need therefore exists for a simple and effective technique for labeling DNA which allows good labeling yield and therefore good sensitivity, which is specific at the level of the labeling position and in particular which does not affect the hybridization properties of the bases involved in the formation of the double helix via hydrogen bonds, and finally which allows the fragmentation of DNA with the aim of hybridizing these labeled DNA fragments to nucleic probes, and in particular to nucleic probes attached to a solid support.

SUMMARY OF THE INVENTION

The present invention describes a method for labeling and fragmenting a single- or double-stranded deoxyribonucleic acid (DNA) comprising the following steps:

fragmenting the DNA by creating at least one abasic site on said DNA, attaching a marker to at least one of the fragments by means of a labeling reagent, said reagent covalently and predominantly coupling to at least one phosphate of said fragment.

The fragmentation and labeling are carried out in one or two steps and the labeling can be carried out either before, after or simultaneously with the fragmentation.

Preferably, the labeling and/or the fragmentation is (are) carried out in a substantially aqueous homogeneous solution. Preferably, the labeling and the fragmentation are carried out simultaneously, that is to say that the reagents necessary for these two steps are put together in a substantially aqueous solution with the nucleic acid for example. This is in particular the case for chemical or enzymatic fragmentation. In the case of mechanical fragmentation by a physical means, labeling and fragmentation being carried out simultaneously means that the physical means is applied to a solution containing at least the nucleic acids and the labeling reagent.

The expression substantially aqueous solution is understood to mean a solution containing at least 50% of water. This solution preferably contains salts like a buffer solution. The expression homogeneous solution is understood to mean a single-phase solution such as a water/DMSO solution by contrast to a two-phase solution such as a water/chloroform solution.

The fragmentation of the DNA via the creation of an abasic site is carried out by the enzymatic, chemical or physical route.

The fragmentation of DNA by the chemical route is carried out by bringing the nucleic acid into contact with a chemical means of creating an abasic site.

Examples of conditions for chemical fragmentation via an abasic site of the DNA are given in G. Pratviel et al., Angew. Chem. Tnt. Ed. Engl., 34, p. 746–769, 1995; G. Pratviel et al., Adv. Inorg. Chem., 45, p. 251–312, 1998; D. S. Sigman et al., Chem. Rev., 93, p. 2295–2316, 1993; J. Lhomme et al., Biopolymers (Nucleic Acid Sciences), 52, p. 65–83, 1999.

An abasic site is created when the N-glycoside bond linking the modified base to the deoxyribose is hydrolyzed, leaving the phosphodiester bond intact. This phenomenon is called depurination (in the case of purines) or depyrimidination (in the case of pyrimidines). Depurination is a lot more frequent that depyrimidination.

Chemical agents such as acidic pH, oxidizing agents or alkylating agents can induce the phenomenon of depurination and therefore the formation of abasic sites. These alkylating agents consist of electrophilic species which react with the nucleophilic sites of a DNA fragment. The nitrogen atom in the 7-position of the guanine is the principal site of alkylation of DNA. In addition to the protonation of the purines, alkylation is one of the chemical modifications capable of making the N-glycoside bond more labile.

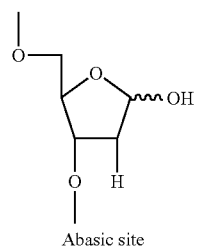

Abasic site

The oxidation of DNA can also generate so-called "alkalilabile" abasic lesions which lead to the fragmentation of DNA in the presence of a base. For example, the ribonolactone residue may be generated by the reaction of the hydroxyl (OH) radical with the C1' carbon.

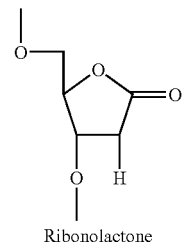

Ribonolactone

The abasic site is very unstable. In its aldehyde form, it can easily undergo a β-elimination of the phosphodiester attached at the 3'-position, which leads to the fragmentation of the DNA strand.

The depurination is spontaneous under physiological conditions (pH 7.4 at 37° C.) but the rate of the reaction is very low, of the order of $3 \times 10^{-11}$ depurination per second, that is to say unusable for an effective fragmentation. To increase the reaction rate, alkylating agents which make the N-glycoside bond fragile or enzymes such as DNA glycosylases are used.

A preferred embodiment of the fragmentation is obtained by the use of an acidic pH, that is to say a pH of less than 5. Advantageously, the pH is about 3.

A sodium formate buffer at pH 3 makes it possible to effectively fragment the nucleic acids according to the present invention. This buffer is compatible with the conditions for labeling in one step as will be demonstrated in the examples. Even more advantageously, an acidic medium (HCl, carbonate, $H_2SO_4$) is used.

In a particular embodiment of the present invention and with the aim of further increasing fragmentation, the deoxyribonucleic acid contains at least one modified base capable of more easily generating an abasic site.

Various modified bases can be used, such as N7-alkylpurines, N3-alkylpurines, O6-alkylpurines, 8-bromopurines, 8-thiopurines, 8-alkylthiopurines, 8-azidopurines or 8-alkylsulfonylpurines.

In the case where the nucleic acid to be labeled is generated by an enzymatic amplification technique such as PCR, the use of an 8-bromopurine makes it possible to have an effective incorporation of said nucleotide during amplification, which correspondingly facilitates the fragmentation and labeling method according to the invention while preserving excellent sensitivity for the enzymatic amplification step. An 8-methylthiopurine is also incorporated without impeding the PCR amplification and incorporation efficiency. Once incorporated, the thioether base is oxidized by a peracid or a monopersulfate derivative, such as potassium peroximonosulfate for example, to the corresponding sulfonyl which is very labile. It has been demonstrated that the half-life period corresponding to the hydrolysis of an 8-methylsulfonylguanosine is less than 2 minutes whereas the half-life period for its natural homolog is 1000 hours.

The expression marker is understood to mean at least one marker capable of directly or indirectly generating a detectable signal. A nonlimiting list of these markers follows:

enzymes which produce a signal detectable for example by colorimetry, fluorescence, luminescence, such as horseradish peroxidase, alkaline phosphatase, β-galactosidase, glucose-6-phosphate dehydrogenase, chromophores such as fluorescent, luminescent or coloring compounds, groups with electron density detectable by electron microscopy or by their electrical property such as conductivity, amperometry, voltametry, impedance, detectable groups, for example whose molecules are of sufficient sizes to induce detectable modifications of their physical and/or chemical characteristics, this detection may be carried out by optical methods such as diffraction, surface plasmon resonance, surface variation, contact angle variation or physical methods such as atomic force spectroscopy, tunnel effect, radioactive molecules such as $^{32}$P, $^{35}$S or $^{125}$I.

Preferably, the marker is not a radioactive marker in order to avoid the safety problems linked to these markers.

In a particular embodiment of the present invention, the marker is electrochemically detectable and in particular the marker is a derivative of an Iron complex such as a ferrocene.

Indirect systems may also be used, such as, for example, ligands capable of reacting with an antiligand. The ligand/antiligand pairs are well known to persons skilled in the art, which is the case, for example, for the following pairs: biotin/streptavidin, hapten/antibody, antigen/antibody, peptide/antibody, sugar/lectin, polynucleotide/complementary strand of the polynucleotide. In this case, it is the ligand which carries the reactive function group. The antiligand may be directly detectable by the markers described in the preceding paragraph or may itself be detectable by another ligand/antiligand pair.

Another example of indirect systems uses a specific covalent bond between the ligand and the antiligand, for example methyl ketone and alkoxyamine. Examples of this system are described in patent applications WO-A-00/40590 and WO-A-98/05766.

In the method of the present invention, the bond between the labeling reagent and the nucleic acid is covalent but it is described above that noncovalent interactions may be used in particular in stacking systems or in the case where the marker is indirectly detectable. The term "attach" therefore covers these various possibilities.

These indirect detection systems may lead, under certain conditions, to amplification of the signal and reference may be made to prior patent applications WO-A-00/07982, WO-A-01/92361 and WO 95/08000 by the applicant for examples of chemical amplification using polymers or to application WO-A-01/44506, also of the applicant, for stacking chemical amplification systems.

In a particular embodiment of signal amplification, at least two markers are present on the labeling reagent.

In a preferred embodiment of the invention, the tracer is a fluorescent compound of low steric hindrance such as fluorescein, dansyl, chromophores of the IR type (Li-COR Inc., Lincoln Nebr., USA), cyanine derivatives such as Cy5 and Cy3 (Randolph J. B. et al., Nucleic Acids Res., 25(14), p. 2923–2929, 1997) and in particular the Cy5 derivatives or alternatively the tracer is a hapten of low steric hindrance such as biotin or an abietane derivative (see application WO-A-00/07982). The expression low steric hindrance is understood to mean a molecular weight of less than 1000 g/mol.

In the case of a fluorophore, it is preferable to work with fluorophores whose excitation wavelength is greater than 450 nm, preferably greater than 600 nm.

In the case where the tracer is a hapten which does not produce a signal by itself, such as for example biotin, the detection is carried out by the reaction of an antiligand as described above. In the case of biotin, streptavidin or an anti-biotin antibody coupled to a fluorescent compound such as fluorescein, Cy5 or Phycoerythrin is preferably used. In the case of abietane, a monoclonal antibody as described in WO-A-00/07982 is used.

The term "deoxyribonucleic acid" or DNA means a succession of at least 2 deoxyribonucleotides optionally comprising at least one modified nucleotide, for example at least one nucleotide containing a modified base such as inosine, methyl-5-deoxycytidine, dimethylamino-5-deoxyuridine, deoxyuridine, diamino-2,6-purine, bromo-5-deoxyuridine or any other modified base allowing hybridization.

This DNA may also be modified at the level of the internucleotide bond such as for example phosphorothioates, H-phosphonates, alkyl phosphonates, at the level of the backbone such as, for example, alpha-oligonucleotides (FR-A-2 607 507) or PNAs (M. Egholm et al., J. Am. Chem. Soc., 114, 1895–1897, 1992). The DNA is natural or synthetic, and/or in the form of a fragment. The DNA is single- or double-stranded.

In particular, the DNA is obtained by an enzymatic amplification technique such as PCR (Polymerase Chain Reaction), described in patents U.S. Pat. No. 4,683,195, U.S. Pat. No. 4,683,202 and U.S. Pat. No. 4,800,159, and its RT-PCR (Reverse Transcription-PCR) derivative, in particular in a one-step format as described in patent application EP-A-0 569 272.

LCR (Ligase Chain Reaction), disclosed for example in patent application EP-A-0 201 184, RCR (Repair Chain Reaction), described in patent application WO-A-90/01069.

The term amplicons is then used to designate the DNA generated by an enzymatic amplification technique. The DNA may also comprise ribonucleotides in a small proportion, for example less than 10%.

Each of these modifications may be taken in combination as long as at least one phosphate is present in the DNA.

The labeling reagent comprises, as reactive functional group, a motif chosen from: diazomethyl; alkyl halide; nitrosourea; spirocyclopropane; aziridine; epoxide; trifluoromethanesulfonates.

The reactive functional groups are described below:

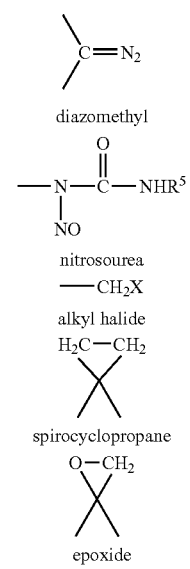

-continued

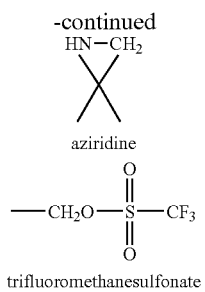

aziridine

—CH₂O—S(=O)(=O)—CF₃ trifluoromethanesulfonate

For the alkyl halide reactive functional group, X means Br, Cl or I. Advantageously, the labeling reagent is 5-(bromomethyl)fluorescein.

For the nitrosourea reactive functional group, $R^5$ is an alkyl or H.

The diazomethyl functional group has already been used for the alkylation of phosphate groups, but a number of problems exist. On the one hand, the diazo derivatives in general are themselves unstable, which generates problems for the use of these labeling reagents in a labeling kit and, on the other hand, the product of coupling is unstable, which rules out its use if the role of the labeled product is to detect the presence of a biological target molecule in any sample, or if it is the labeled target which it is desired to detect.

Finally, the derivatives carrying the diazomethyl functional group are insoluble in water, which leads to two-phase conditions being used for the coupling with nucleic acids, which are only soluble and stable in water or aqueous buffers, but these conditions slow down the rate of reaction and therefore hamper the efficiency of the coupling.

In a preferred embodiment of the method according to the invention, the labeling reagent is chosen from the compounds of formula (1):

in which:
$R^1$ represents H or an alkyl, substituted alkyl, aryl or substituted aryl group,
Z comprises a detectable marker.

Z and/or $R^1$ are chosen in order to stabilize the diazomethyl functional group, that is to say at least one of the two groups Z or $R^1$ has a phenyl nucleus.

Preferably, the labeling reagent is chosen from the compounds of formula (2):

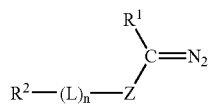

in which:
$R^1$ represents H or an alkyl, aryl or substituted aryl group,
$R^2$ is a detectable marker,
L is a linking arm containing a linear succession of at least two covalent bonds and n is equal to 0 or 1, and
Z is chosen from:

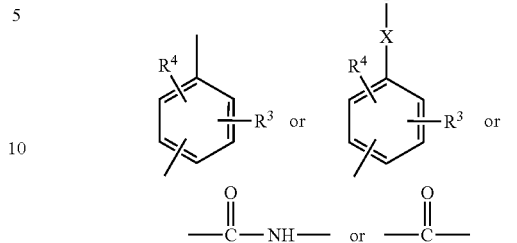

—C(=O)—NH—  or  —C(=O)— in which:
$R^3$ and $R^4$ represent independently of each other: H, $NO_2$, Cl, Br, F, I, OR, SR, $NR_2$, R, NHCOR, CONHR, COOR with R=alkyl or aryl,
—Y—X— represents —CONH—, —NHCO—, —CH₂O—, —CH₂S—.

In a particular embodiment according to formula (1), Z has the following structure:

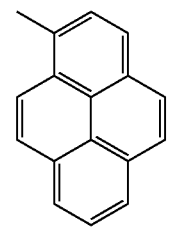

In this case and if $R^2$ is H, the labeling reagent is 1-pyrenyldiazomethane (PDAM).

Although this marker is fluorescent, the excitation wavelength is too close to those of nucleic acids. An indirect detection using a monoclonal antibody directed against the pyrene motif is preferred. The method of producing this antibody is well known to persons skilled in the art (see for example patent application WO-A-00/07982).

In a preferred embodiment of the method, the labeling reagent is of formula (3):

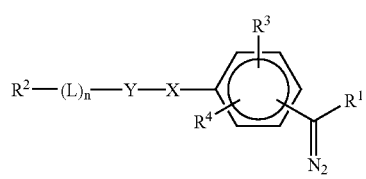

in which:
$R^1$ represents H or an alkyl, aryl or substituted aryl group,
$R^2$ represents a detectable marker,
L is a linking arm containing a linear succession of at least two covalent bonds and n an integer equal to 0 or 1,
$R^3$ and $R^4$ represent independently of each other: H, $NO_2$, Cl, Br, F, I, OR, SR, $NR_2$, R, NHCOR, CONHR, COOR with R=alkyl or aryl,
—Y—X— represents —CONH—, —NHCO—, —CH₂O—, —CH₂S—.

Advantageously, the reagent is of formula (4):

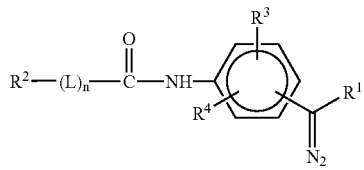

in which:
$R^1$ represents H or an alkyl, aryl or substituted aryl group,
$R^2$ represents a detectable marker,
L is a linking arm containing a linear succession of at least two covalent bonds and n an integer equal to 0 or 1,
$R^3$ and $R^4$ represent independently of each other: H, $NO_2$, Cl, Br, F, I, OR, SR, $NR_2$, R, NHCOR, CONHR, COOR with R=alkyl or aryl.

Advantageously, the reagent is of formula (5):

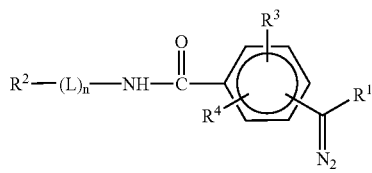

in which:
$R^1$ represents H or an alkyl, aryl or substituted aryl group,
$R^2$ represents a detectable marker,
L is a linking arm containing a linear succession of at least two covalent bonds and n an integer equal to 0 or 1,
$R^3$ and $R^4$ represent independently of each other: H, $NO_2$, Cl, Br, F, I, OR, SR, $NR_2$, R, NHCOR, CONHR, COOR with R=alkyl or aryl.

Advantageously, the reagent is of formula (6):

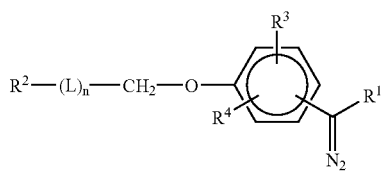

in which:
$R^1$ represents H or an alkyl, aryl or substituted aryl group,
$R^2$ represents a detectable marker,
L is a linking arm containing a linear succession of at least two covalent bonds and n an integer equal to 0 or 1,
$R^3$ and $R^4$ represent independently of each other: H, $NO_2$, Cl, Br, F, I, OR, SR, $NR_2$, R, NHCOR, CONHR, COOR with R=alkyl or aryl.

In the above formulae (3) to (6), advantageously $R^3$ and $R^4$ represent independently of each other: H, $NO_2$, $OCH_3$.

Thus, a preferred compound according to formula (6) is of formula (6'):

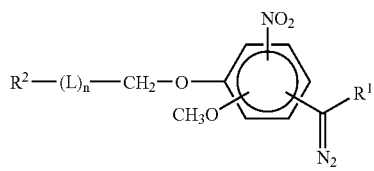

in which:
$R^1$ represents H or an alkyl, aryl or substituted aryl group,
$R^2$ represents a detectable marker,
L is a linking arm containing a linear succession of at least two covalent bonds and n an integer equal to 0 or 1.

A preferred compound according to formula (4) is of formula (4'):

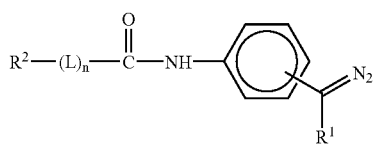

in which:
$R^1$ represents H or an alkyl, aryl or substituted aryl group,
$R^2$ represents a detectable marker,
L is a linking arm containing a linear succession of at least two covalent bonds and n an integer equal to 0 or 1.

In a particular embodiment of the method where it is desired to amplify the signal, at least two markers are present on the labeling reagent. In particular, a reagent which makes it possible to carry out the signal amplification according to the present invention possesses a structure $R^2$-$(L)_n$- of formula (7) below:

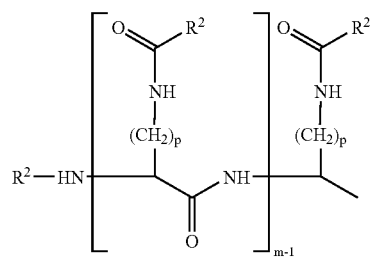

in which:
$R^2$ represents a detectable marker,
m is an integer between 1 and 100, preferably between 1 and 20,
p is an integer between 1 and 10, advantageously 2 to 6, preferably 4.

This structure of $R^2$-$(L)_n$ applies without distinction to formulae (2) to (6) above.

Another preferred labeling reagent for the signal amplification is the reagent of formula (8):

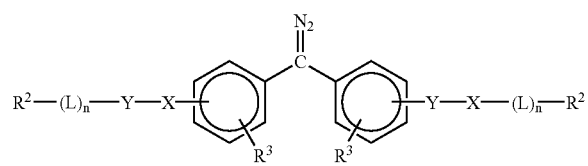

in which:
$R^2$ represents a detectable marker,
$R^3$ represents H, $NO_2$, Cl, Br, F, I, OR, SR, $NR_2$, R, NHCOR, CONHR, COOR with R=alkyl or aryl,
L is a linking arm containing a linear succession of at least two covalent bonds and n an integer equal to 0 or 1,
—Y—X— represents —CONH—, —NHCO—, —$CH_2O$—, —$CH_2$—.

Advantageously, the reagent for the signal amplification has the formula (9)

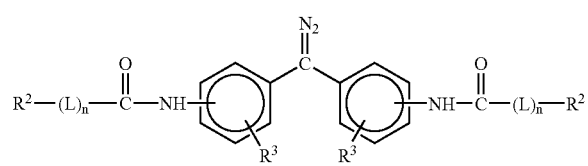

in which:
$R^2$ represents a detectable marker,
$R^3$ represents H, $NO_2$, Cl, Br, F, I, OR, SR, $NR_2$, R, NHCOR, CONHR, COOR with R=alkyl or aryl, preferably $R^3$ represents H, $NO_2$ or $OCH_3$,
L is a linking arm containing a linear succession of at least two covalent bonds and n an integer equal to 0 or 1.

Some advantageous reagents of the invention are:

a) of formula (10):

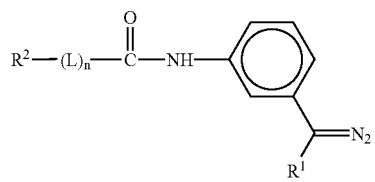

in which:
$R^1$ represents H or an alkyl or aryl or substituted aryl group,
$R^2$ represents a detectable marker,
L is a linking arm containing a linear succession of at least two covalent bonds and n an integer equal to 0 or 1, b) of formula (11):

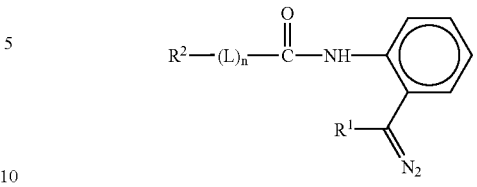

in which:
$R^1$ represents H or an alkyl or aryl or substituted aryl group,
$R^2$ represents a detectable marker,
L is a linking arm containing a linear succession of at least two covalent bonds and n an integer equal to 0 or 1.

c) of formula (12):

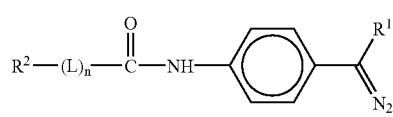

in which:
$R^1$ represents H or an alkyl or aryl or substituted aryl group,
$R^2$ represents a detectable marker,
L is a linking arm containing a linear succession of at least two covalent bonds and n an integer equal to 0 or 1.

Preferably, the labeling reagent has:

a) the structure

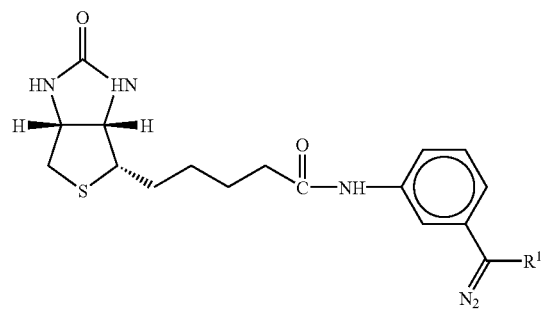

in which $R^1$ represents a methyl group or a phenyl, or b) the structure:

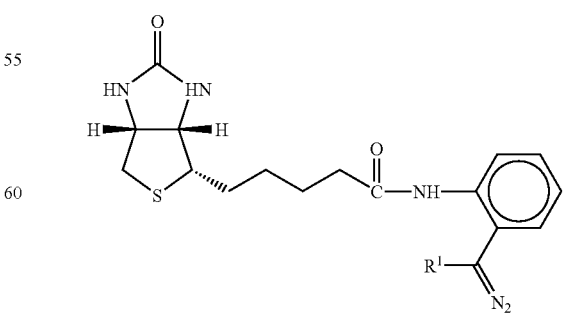

in which $R^1$ represents a methyl or phenyl group, or c) the structure:

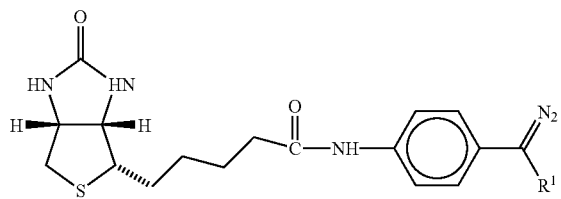

in which R¹ represents a methyl or phenyl group.

Other preferred reagents according to the invention have the formula (13):

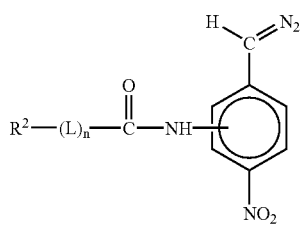

in which:

R² represents a detectable marker,

L is a linking arm containing a linear succession of at least two covalent bonds and n an integer equal to 0 or 1.

In particular, the labeling reagents according to the method of the invention are soluble in water-miscible polar solvents such as DMF, DMSO, CH₃CN, THF, DMA (dimethylacetamide), NMP (N-methylpyrrolidone), DME (dimethoxyethane).

Preferably, the labeling reagents are soluble in DMSO or water.

The expression water-miscible solvent is understood to mean a solvent which is miscible in a proportion of at least 5% by volume with water or an aqueous buffer containing salts.

Advantageously, in the preceding formulae, the arm L comprises an ethylene glycol or polyethylene glycol motif in order to increase the solubility of the reagent in water.

These reagents can thus bind in the homogeneous phase to nucleic acids, the homogeneous phase consisting of a substantially aqueous solution, that is to say containing at least 50% of water.

One aim of the present invention is to describe a method for detecting a single- or double-stranded target deoxyribonucleic acid (DNA) comprising the following steps:

a) fragmenting and labeling said DNAs according to any one of the methods described above, b) hybridizing the labeled fragments to at least one nucleic probe which is sufficiently specific for the target nucleic acid, c) detecting the hybrid formed using the marker.

As will be demonstrated in the examples, the denaturation of the DNA before hybridization makes it possible to increase the sensitivity. This denaturation step takes place after the fragmentation and the labeling.

In a particular embodiment of the method, an enzymatic amplification step occurs before the fragmentation and the labeling. The enzymatic amplification step generates DNA amplicons from a target DNA nucleic acid but also from a target RNA nucleic acid such as a messenger RNA, a transfer RNA or a ribosomal RNA. The RT-PCR technique, for example, is a known means for amplifying RNA.

Preferably, the fragmentation, labeling and denaturation steps take place at the same time both in the case of a target natural nucleic acid and in the case of a target nucleic acid obtained by an enzymatic amplification technique.

The fragmentation by creation of an abasic site involves the loss of a base. In the methods for detecting a target nucleic acid and in particular in the genotyping methods, that is to say in the methods where the target nucleic acid exhibits a polymorphism distributed over its sequence, it is necessary to identify a plurality of modifications of sequences some of which represent the modification of a single base between the target and the nucleic probes whose function is to identify this modification (capture probes). Specificity is therefore essential in this context. Surprisingly, the present invention demonstrates that this loss of a base does not at all affect the hybridization specificity for a labeled and fragmented nucleic acid according to the invention.

The subject of the present invention is also a method for detecting a polymorphism distributed in predetermined or nonpredetermined positions of a target nucleic acid by the presence of a plurality of deletions and/or insertions and/or mutations in the sequence of said target nucleic acid relative to a so-called reference sequence, comprising the following steps:

a) having a target DNA containing the entire polymorphism to be studied, said DNA being optionally generated by an enzymatic amplification technique, b) fragmenting and labeling said DNA by one of the methods described above, c) hybridizing said fragments to a plurality of nucleic probes termed capture probes, the plurality of capture probes being attached to a solid support and the plurality of capture probes covering in its entirety at least the polymorphism to be studied, d) detecting the hybrids formed between the labeled fragments and at least part of the nucleic probes using the marker and deducing therefrom the polymorphism of the target DNA.

As indicated above, a denaturation step after the fragmentation and labeling step makes it possible to improve the sensitivity of the method and this step is preferably carried out simultaneously with the labeling and fragmentation step.

The fragmentation and labeling method according to the invention is particularly useful in the case where the labeled and fragmented DNA has to hybridize with a multitude of nucleic acids, especially oligonucleotides, attached to the solid support at a predetermined position in order to form a DNA chip. The expression "DNA chip" is understood to mean a small-size solid support where a multitude of capture probes are attached at predetermined positions. The expression multitude is understood to mean a solid support containing at least ten nucleic probes of different sequences, advantageously at least four hundred (400), preferably at least one thousand (1000).

Indeed, the density of the nucleic acids attached to the solid support imposes major steric constraints during hybridization and the fragmentation makes it possible to improve this hybridization step. Examples of these DNA chips are given, for example, in the publications by G. Ramsay, Nature Biotechnology, 16, p. 40–44, 1998; F. Ginot, Human Mutation, 10, p. 1–10, 1997; J. Cheng et al., Molecular diagnosis, 1(3), p. 183–200, 1996; T. Livache et al., Nucleic Acids Research, 22(15), p. 2915–2921, 1994; J. Cheng et al., Nature Biotechnology, 16, p. 541–546, 1998. The term "solid support" as used here includes all the materials to which a nucleic acid may be attached. The solid support may be in the form of a microtiter plate, a membrane, a particle or a substantially flat plate.

The invention relates to the use of a labeled DNA, as defined above, as a probe for detecting a target nucleic acid.

To allow the detection and/or quantification and/or purification of the target nucleic acid, the labeled DNA is capable of forming a hybridization complex with a nucleic probe. By way of example, the labeled nucleic acid is sufficiently complementary to the target to become specifically hybridized depending on the reaction conditions and in particular the temperature or the salinity of the reaction medium.

The method of detection is applicable for sequencing, messenger RNA expression profiling or screening of mutations for the purposes of research and screening of drugs in the pharmaceutical industry, the diagnosis of infectious diseases (in bacteriology, virology and parasitology) or of genetic diseases, food or industrial control.

Numerous publications describe these types of applications: Antoine de Saizieu et al., Nature Biotechnology, 16, p. 44–48, 1998; Thomas R. Gingeras et al., Genome Research, 8, p. 435–448, 1998; David J. Lockhart et al., Nature Biotechnology, 14, p. 1675–1680, 1996; Daniel D. Shoemaker et al., Nature Genetics, Vol. 14, p. 450–456, 1996; R. J. Lipshutz et al., BioTechniques, 19(3), p. 442–447, 1995; David G. Wang et al., Science, 280, p. 1077–1082, 1998; Kevin L. Gunderson et al., Genome Research, 8, p. 1142–1152, 1998; Joseph G. Hacia et al., Nature Genetics, Vol. 14, p. 441–447, 1996.

The trend in the field of diagnosis and in particular for infectious diseases (AIDS or Tuberculosis for example) is to lower the sensitivity level down to the detection of a single molecule in a sample which may represent several milliliters in the case of a liquid sample of the blood or urine or cerebrospinal fluid type. This sensitivity level can only be obtained if all the steps, from the taking of the sample to the issuing of results, are optimized. In particular, in the case where an enzymatic amplification step is necessary in order to obtain the necessary sensitivity (viral or bacterial infection such as HIV, HCV or Tuberculosis), a labeling and/or fragmentation method as described in the present invention makes it possible not to affect the sensitivity of the amplification technique either because it is not necessary to replace the amplification technique, or because the incorporated deoxyribonucleotides used in the enzymatic deoxyribonucleotides do not alter the sensitivity.

Additional information can be found in another patent application of the applicant, filed on May 4, 2001 under registration number FR 01/06040, and also in its international extension filed on the same day as the present invention.

BRIEF DESCRIPTION OF THE DRAWINGS

The accompanying figures and examples represent particular embodiments and cannot be considered as limiting the scope of the present invention.

Figure 1:
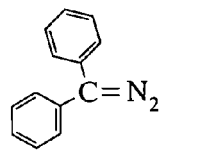
FIG. 1 represents the structural formulae of various reagents used in the present invention as well as the abbreviation designating them. (o—means ortho, m—meta and p—para).
Figure 1:
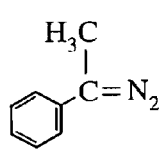
Figure 1:
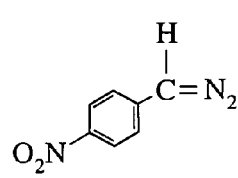
Figure 1:
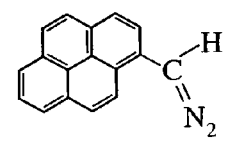
Figure 1:
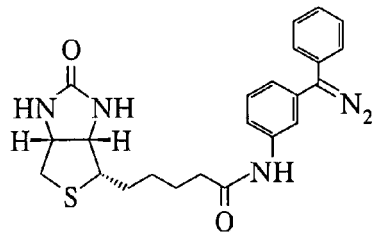
Figure 1:
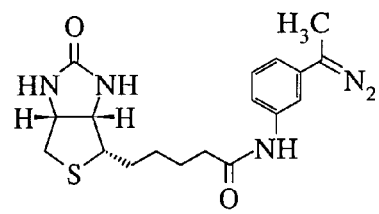
Figure 1:
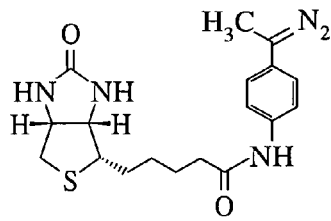
Figure 1:
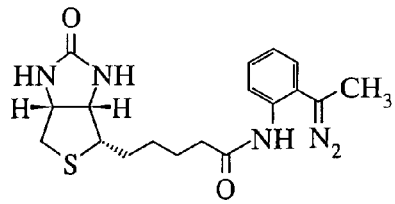
Figure 1:
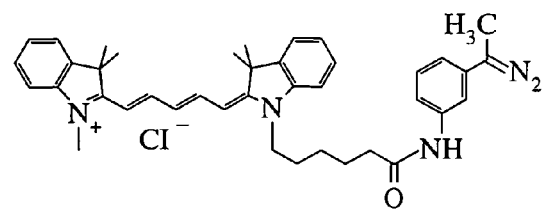
Figure 2A:
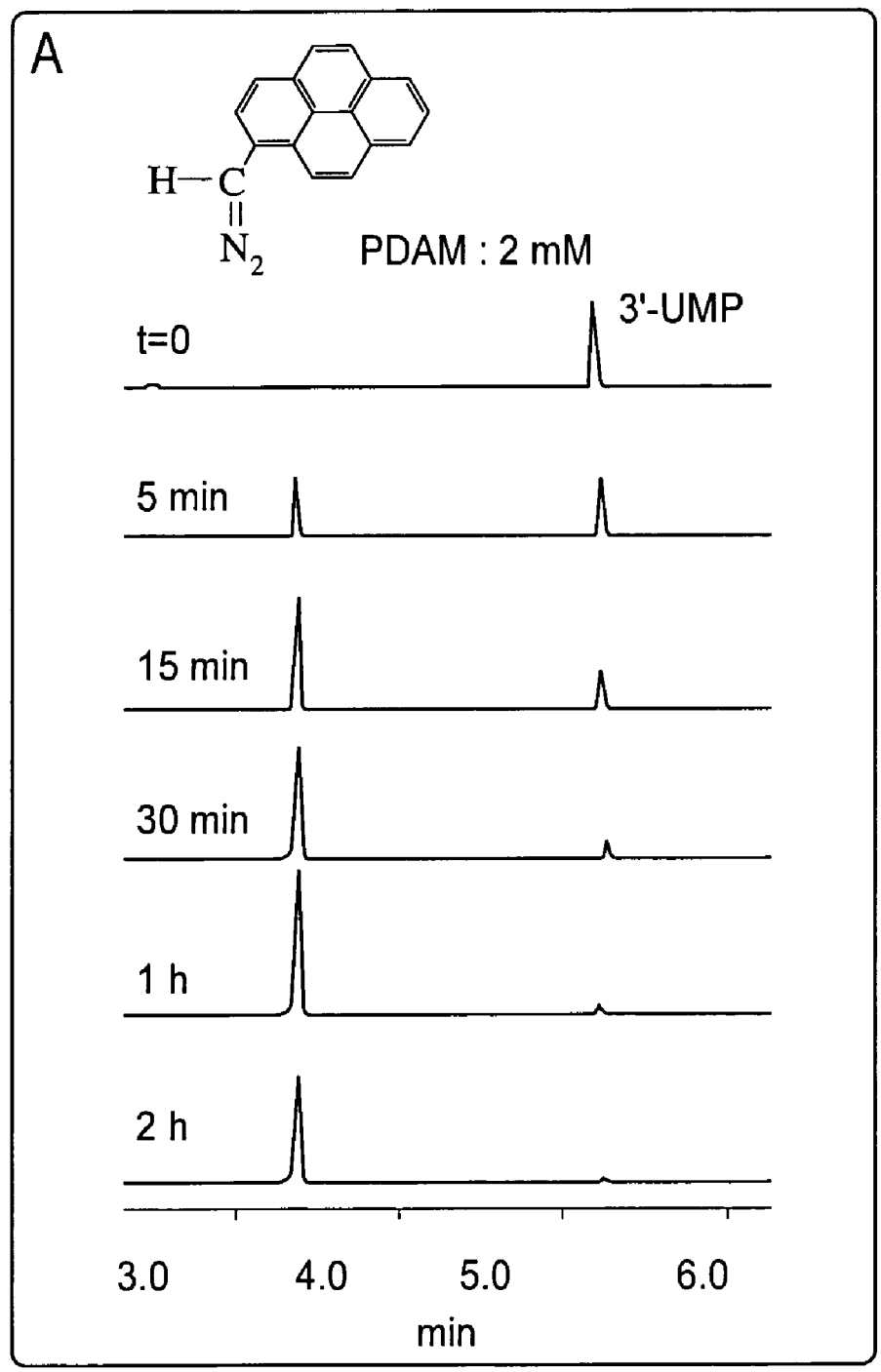
FIGS. 2A to 2I represent the profiles as a function of time, analyzed by capillary electrophoresis, of the covalent coupling of various reagents carrying a diazomethyl functional group on the uridine 3'-monophosphate (3'-UMP) according to Example 6.1. The molecules are as follows.
Figure 2B:
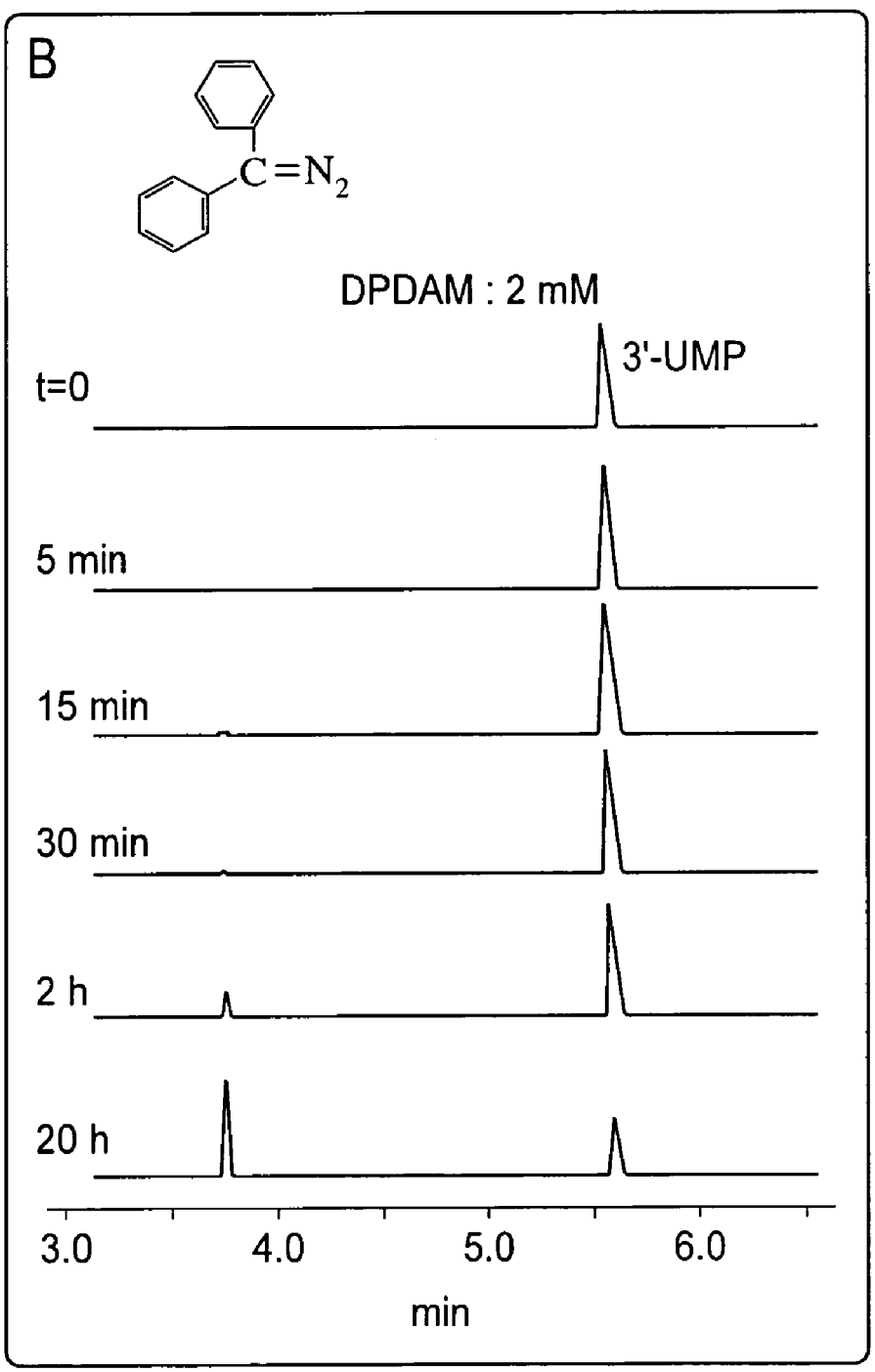
Figure 2C:
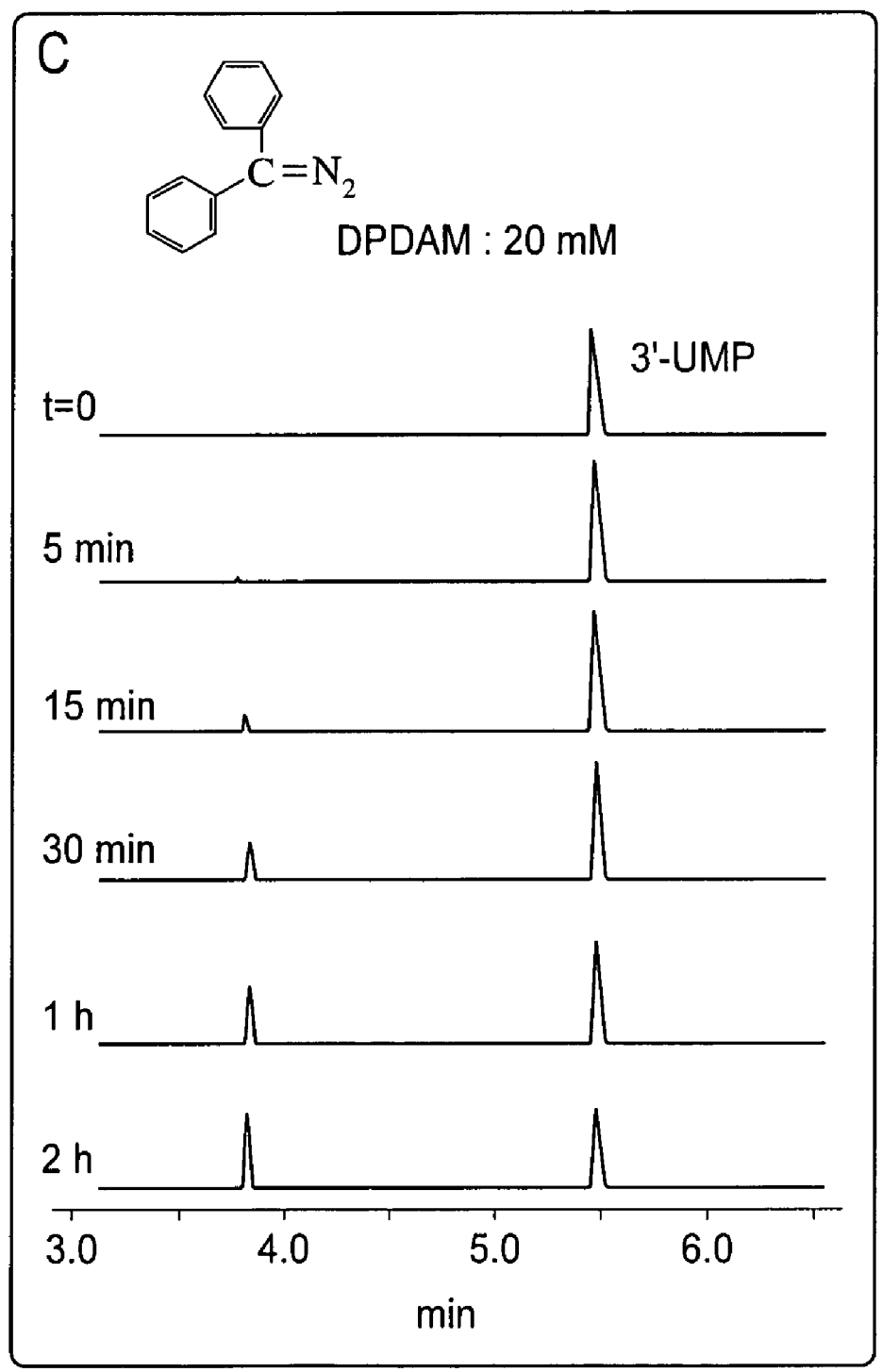
Figure 2D:
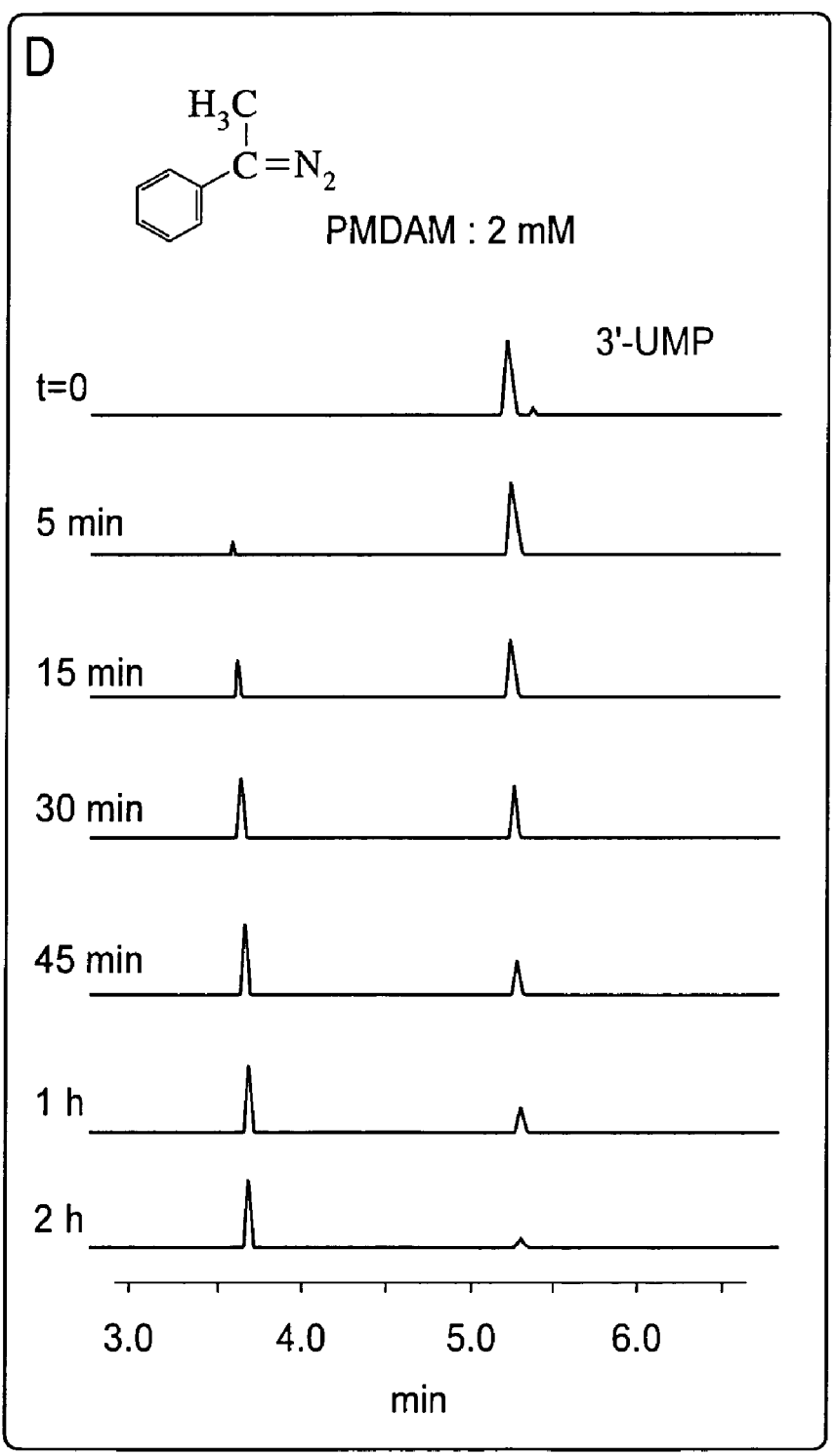
Figure 2E:
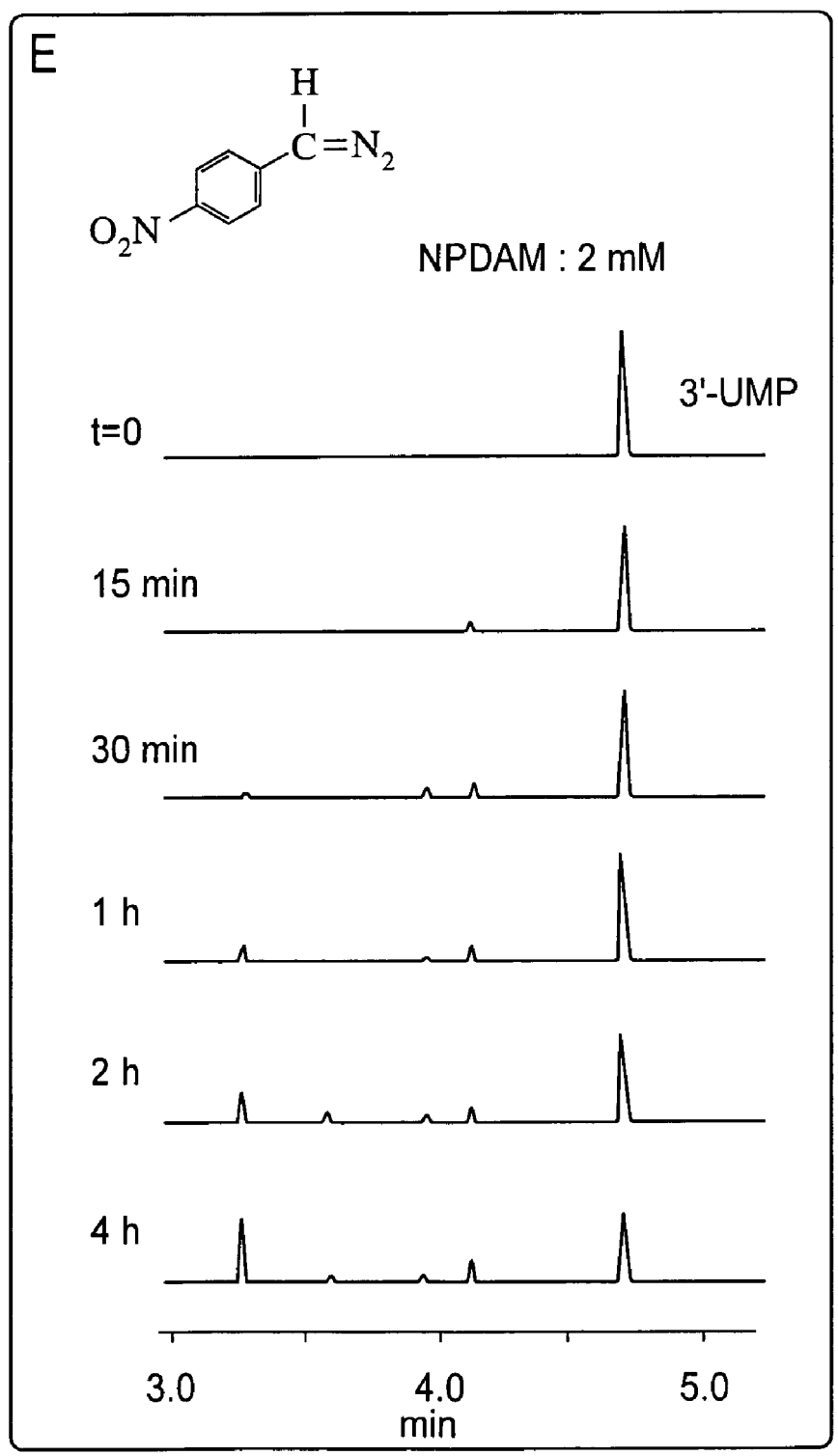
Figure 2F:
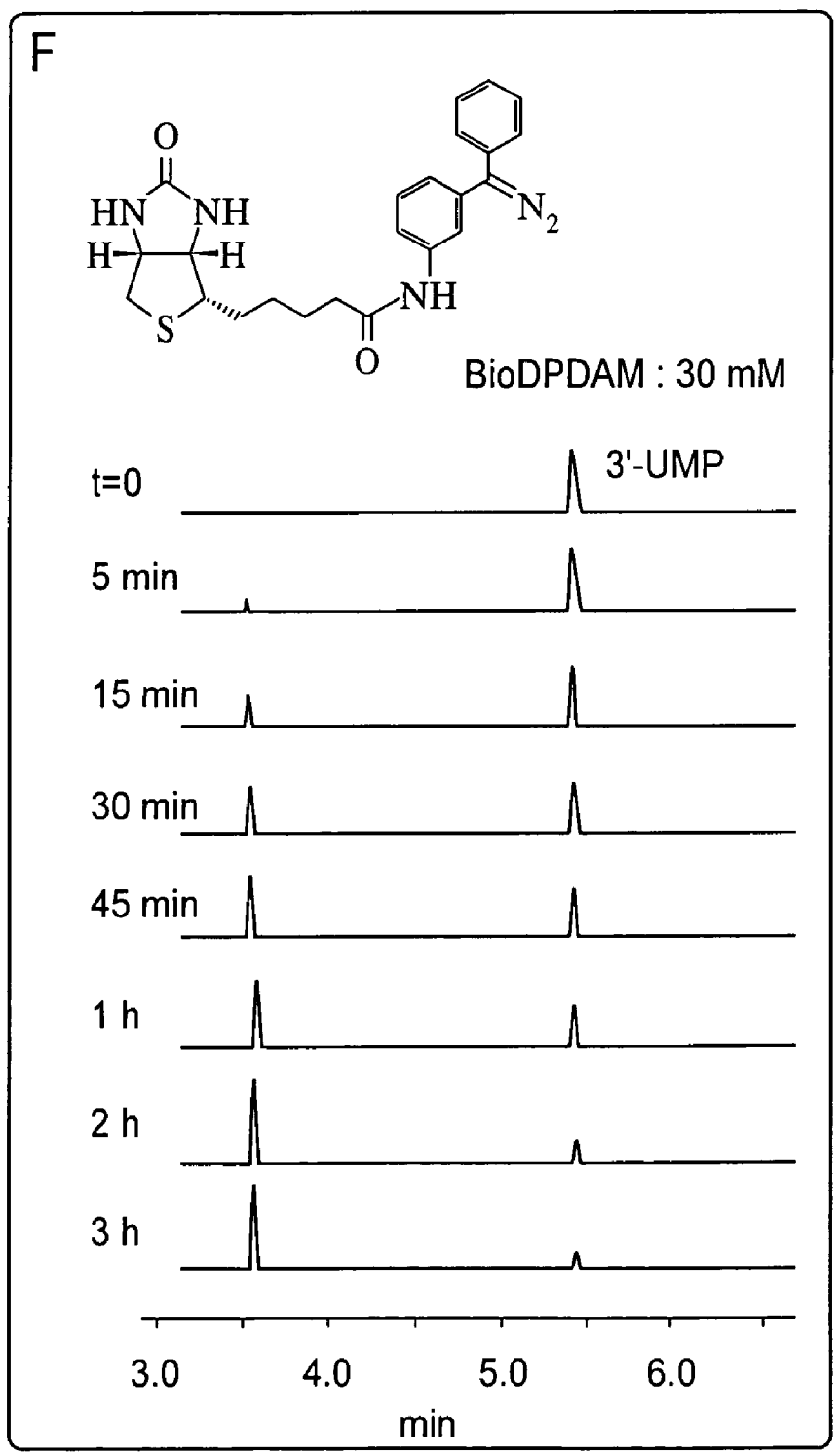
Figure 2G:
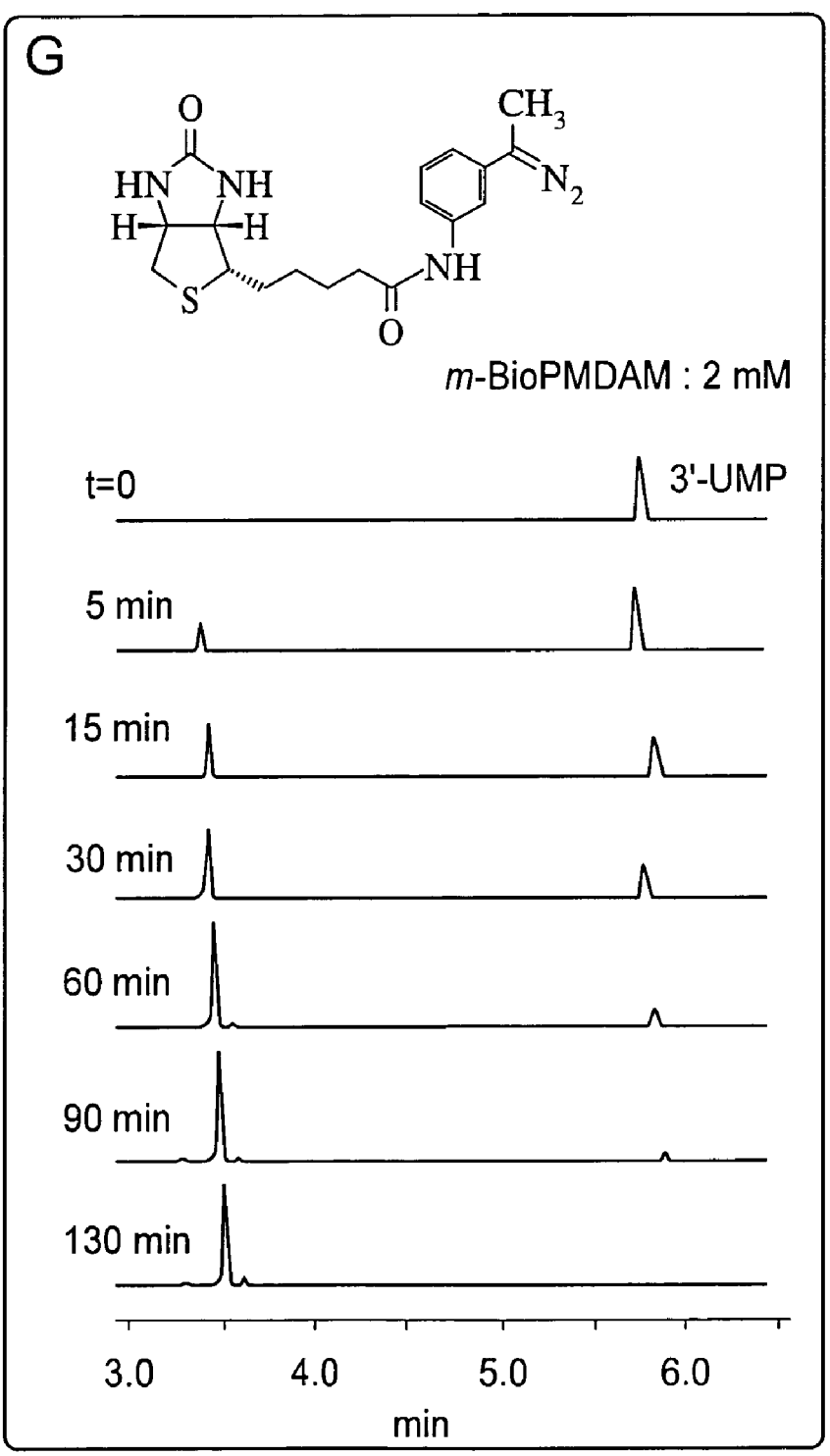
Figure 2H:
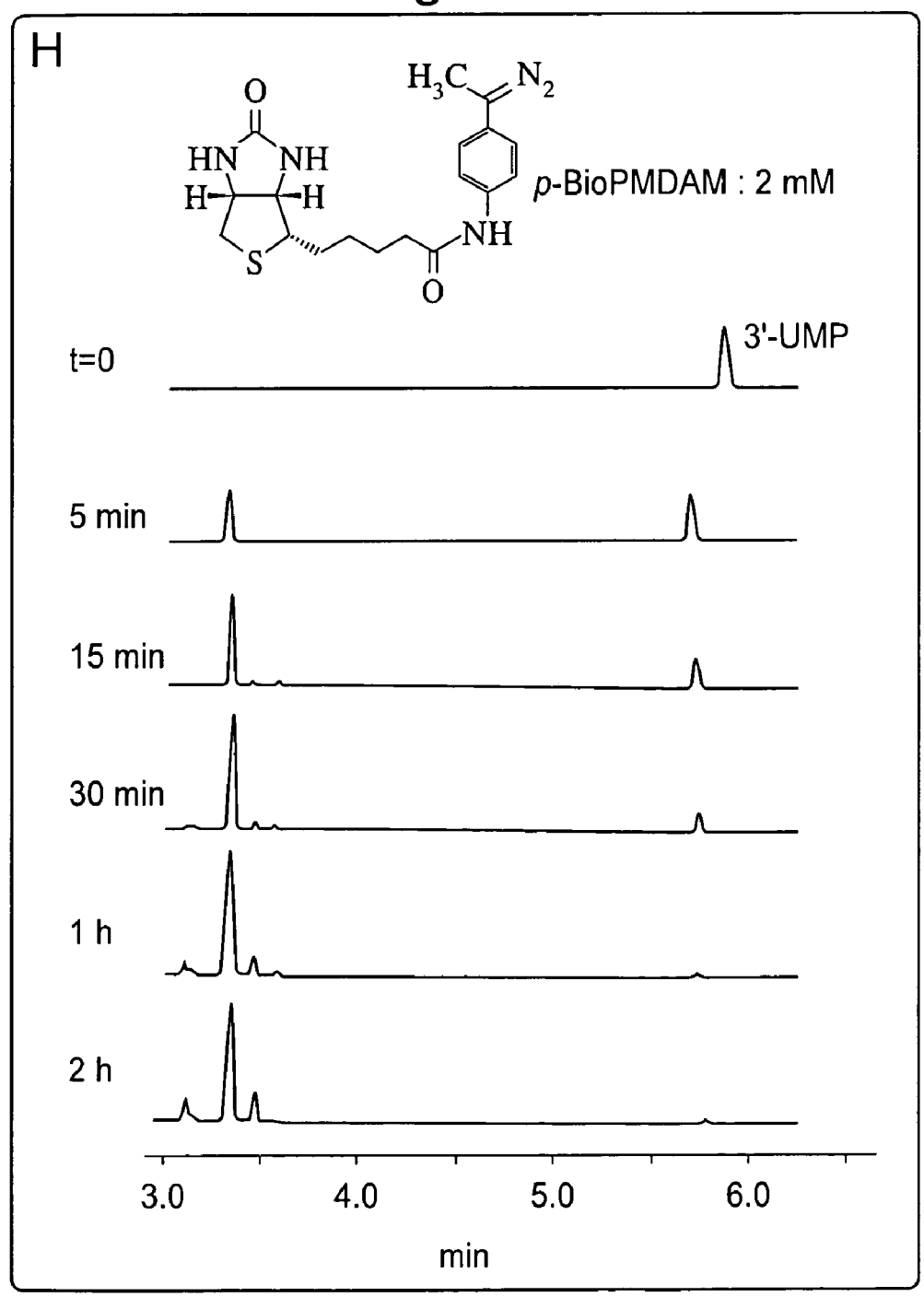
Figure 2I:
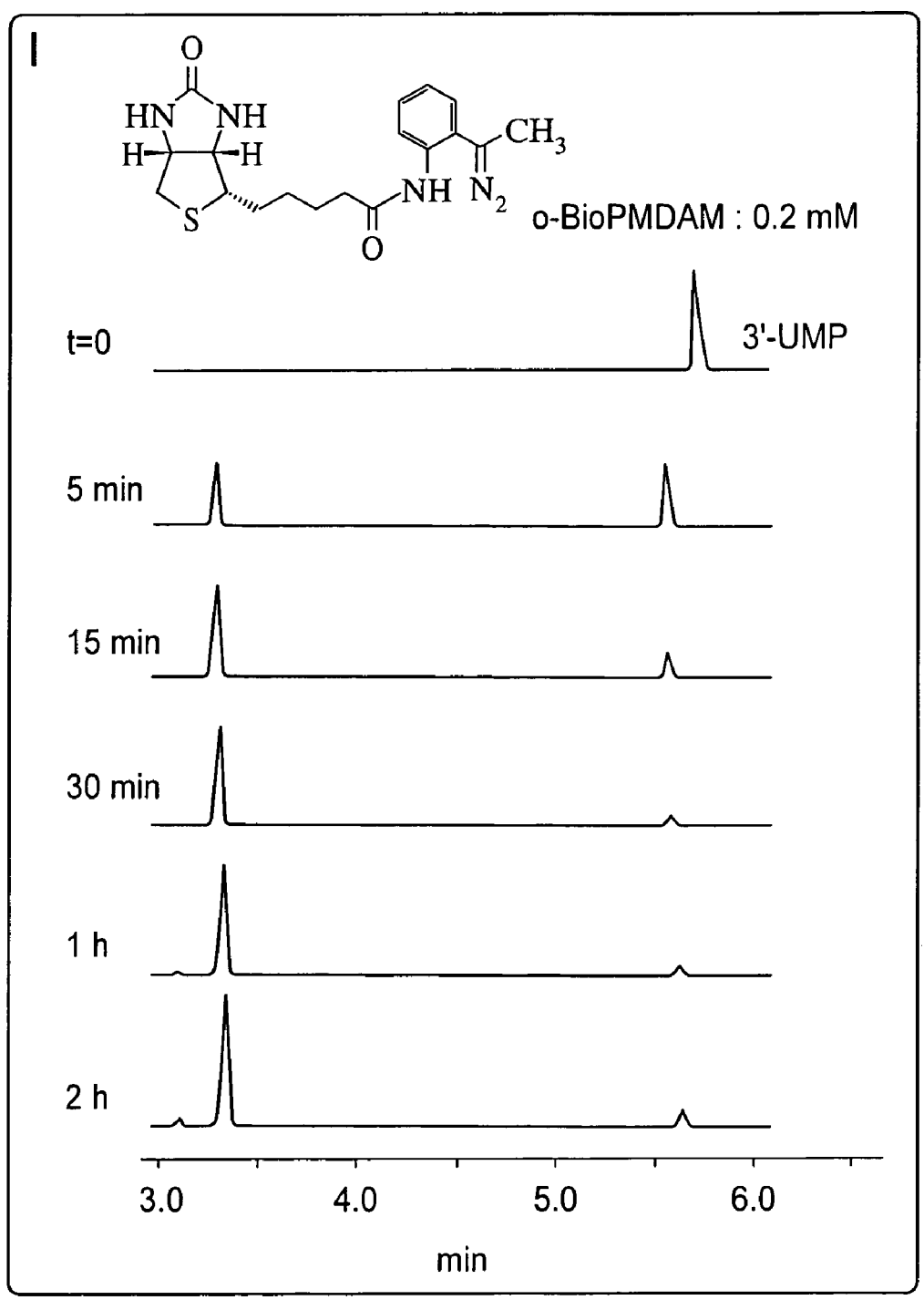

PDAM in FIG. 2A,

DPDAM at 2 mM (millimol per liter) in FIG. 2B,

DPDAM at 20 mM in FIG. 2C,

PMDAM in FIG. 2D,

NPDAM in FIG. 2E,

BioDPDAM in FIG. 2F, meta-BioPMDAM in FIG. 2G, para-BioPMDAM in FIG. 2H, and ortho-BioPMDAM in FIG. 2I.

Figure 3B:
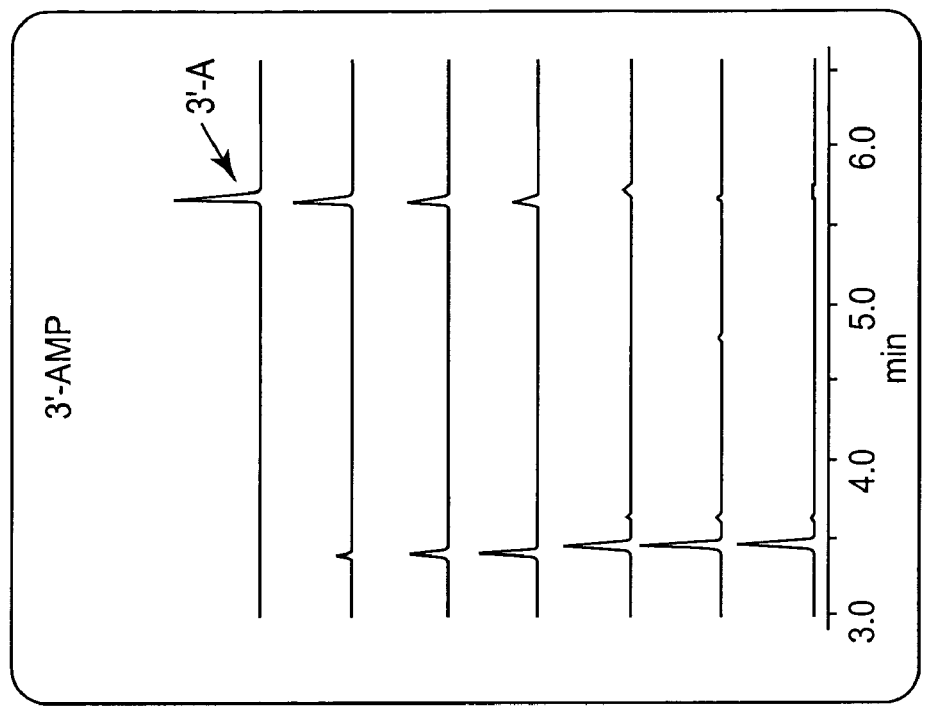
Figure 3A:
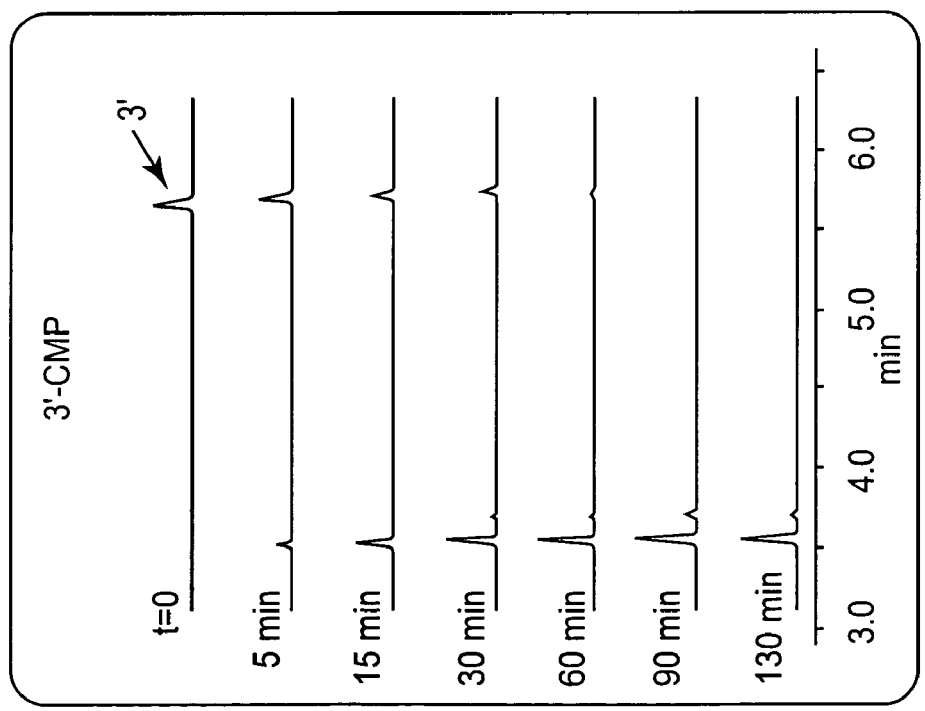

FIGS. 3A to 3D represent the profiles as a function of time, analyzed by capillary electrophoresis, of the reaction of meta-BioPMDAM with four (4) nucleotide 3'-monophosphates according to Example 6.2. The molecules are as follows:

3'-CMP in the ribonucleotide series according to FIG. 3A,

3'-AMP in the ribonucleotide series according to FIG. 3B.

Figure 3D:
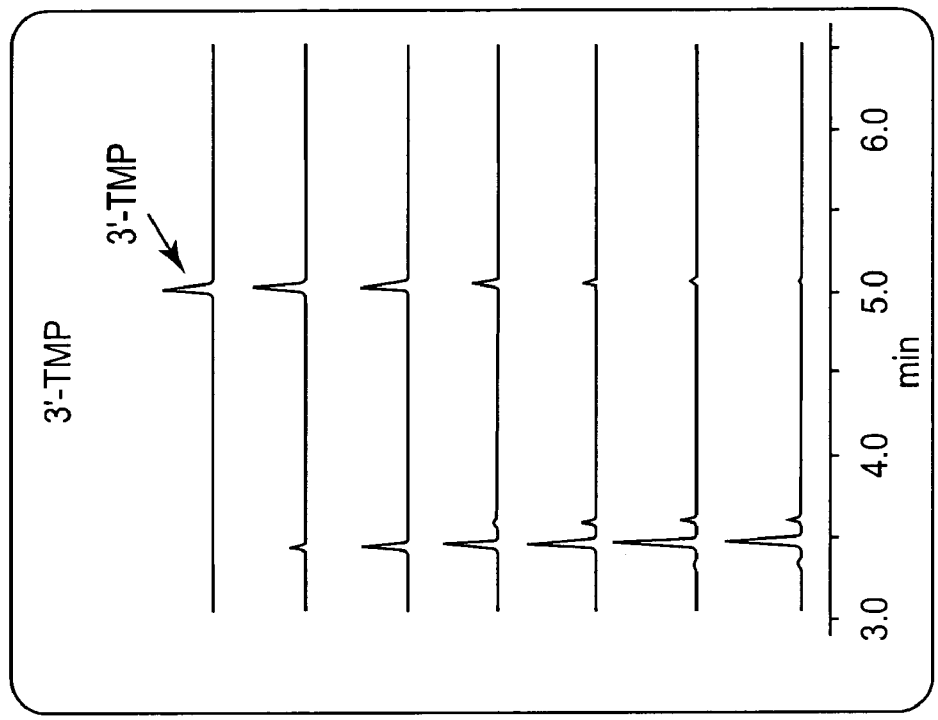
Figure 3C:
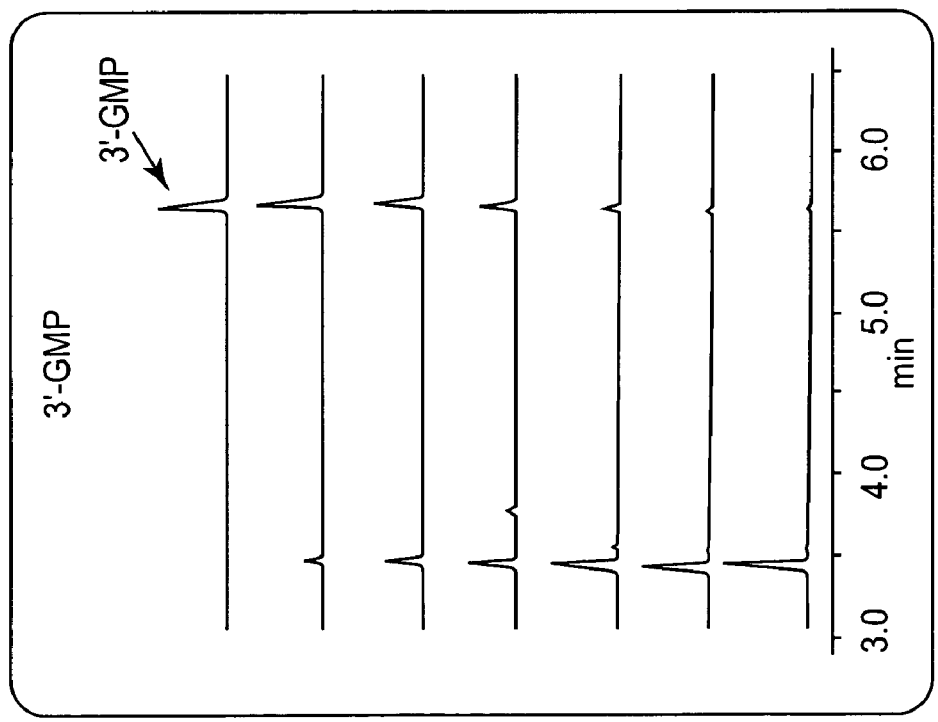

3'-GMP in the ribonucleotide series according to FIG. 3C, and

3'-TMP in the deoxyribonucleotide series according to FIG. 3D.

Figure 4:
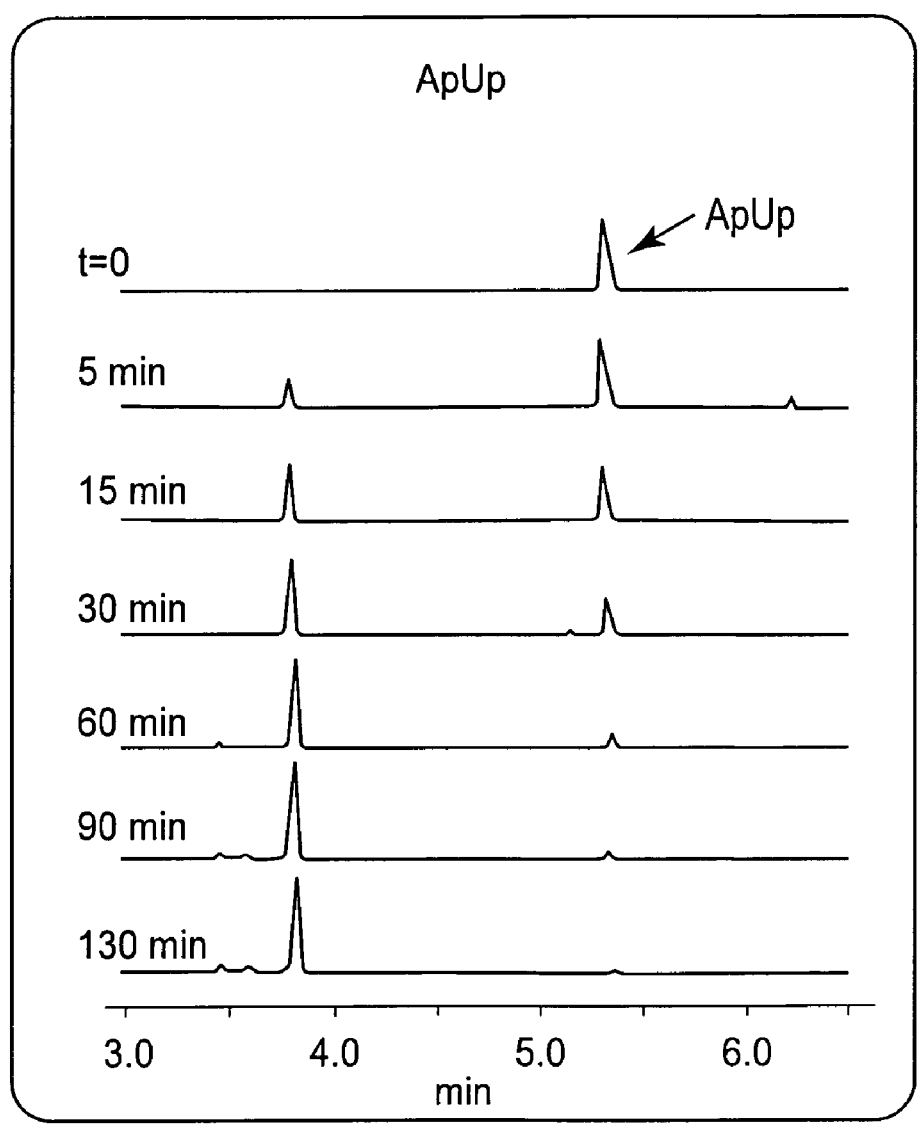

FIG. 4 represents the profiles as a function of time, analyzed by capillary electrophoresis, of the reaction of meta-BioPMDAM with a dinucleotide 5'-ApUp according to Example 6.3.

Figure 5C:
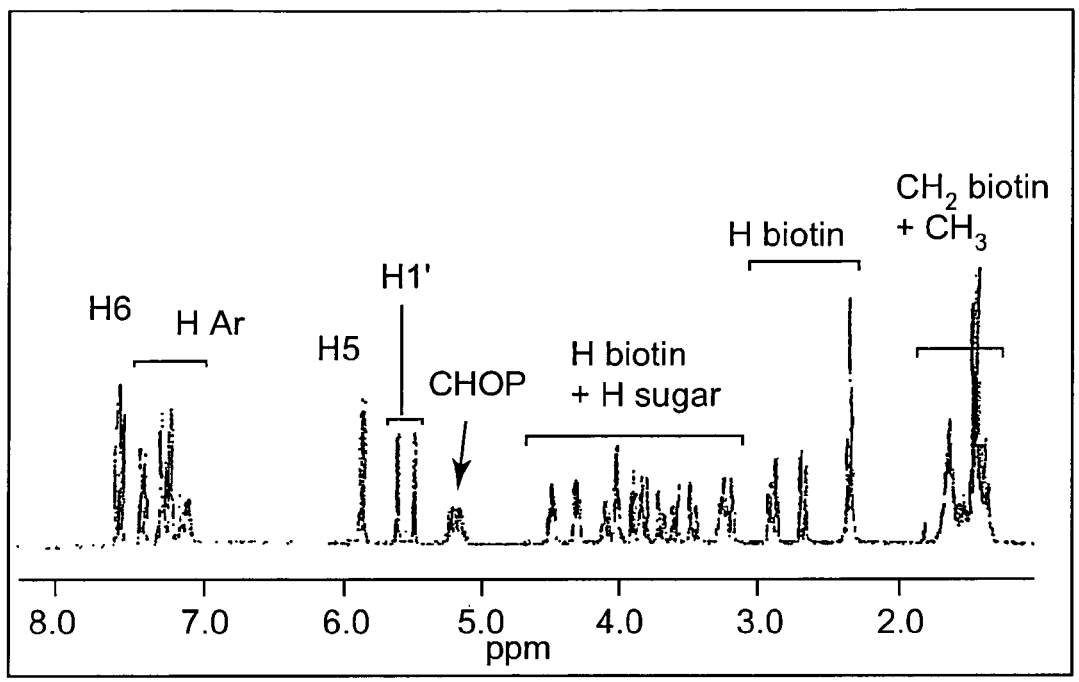

FIGS. 5A to 5D represent the proton NMR spectrum in $D_2O$ of various conjugates between the meta-BioPMDAM reagent and four (4) ribonucleotide 3'-monophosphates according to Example 6.4. The molecules are as follows:

3'-GMP in FIG. 5A,

3'-AMP in FIG. 5B,

3'-CMP in FIG. 5C, and

Figure 5D:
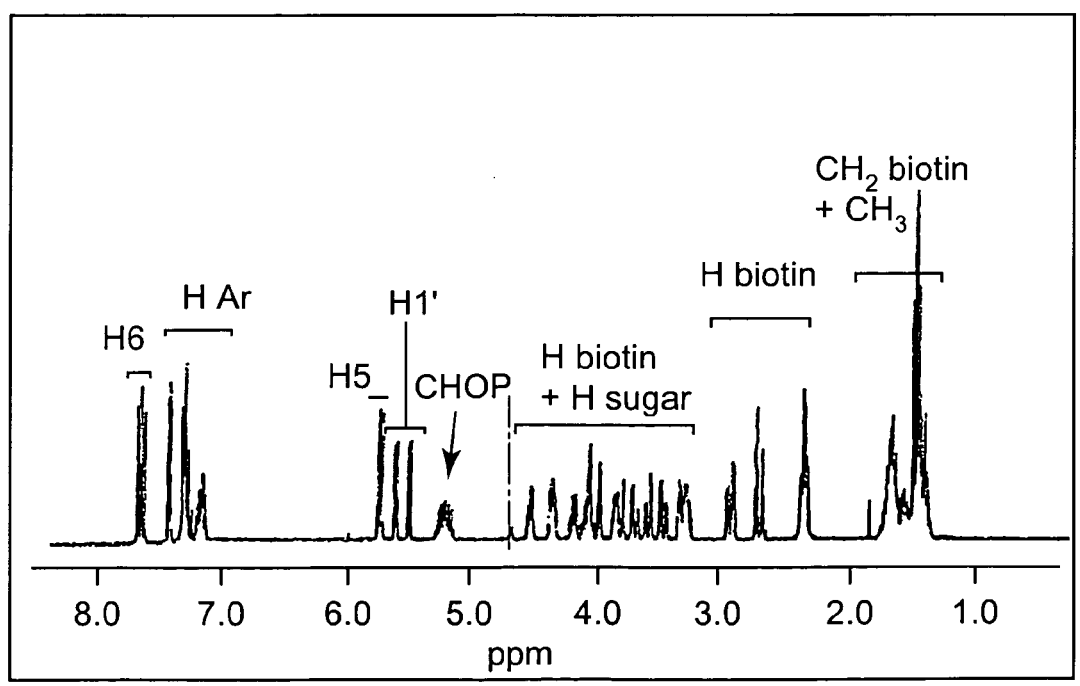

3'-UMP in FIG. 5D.

Figure 6:
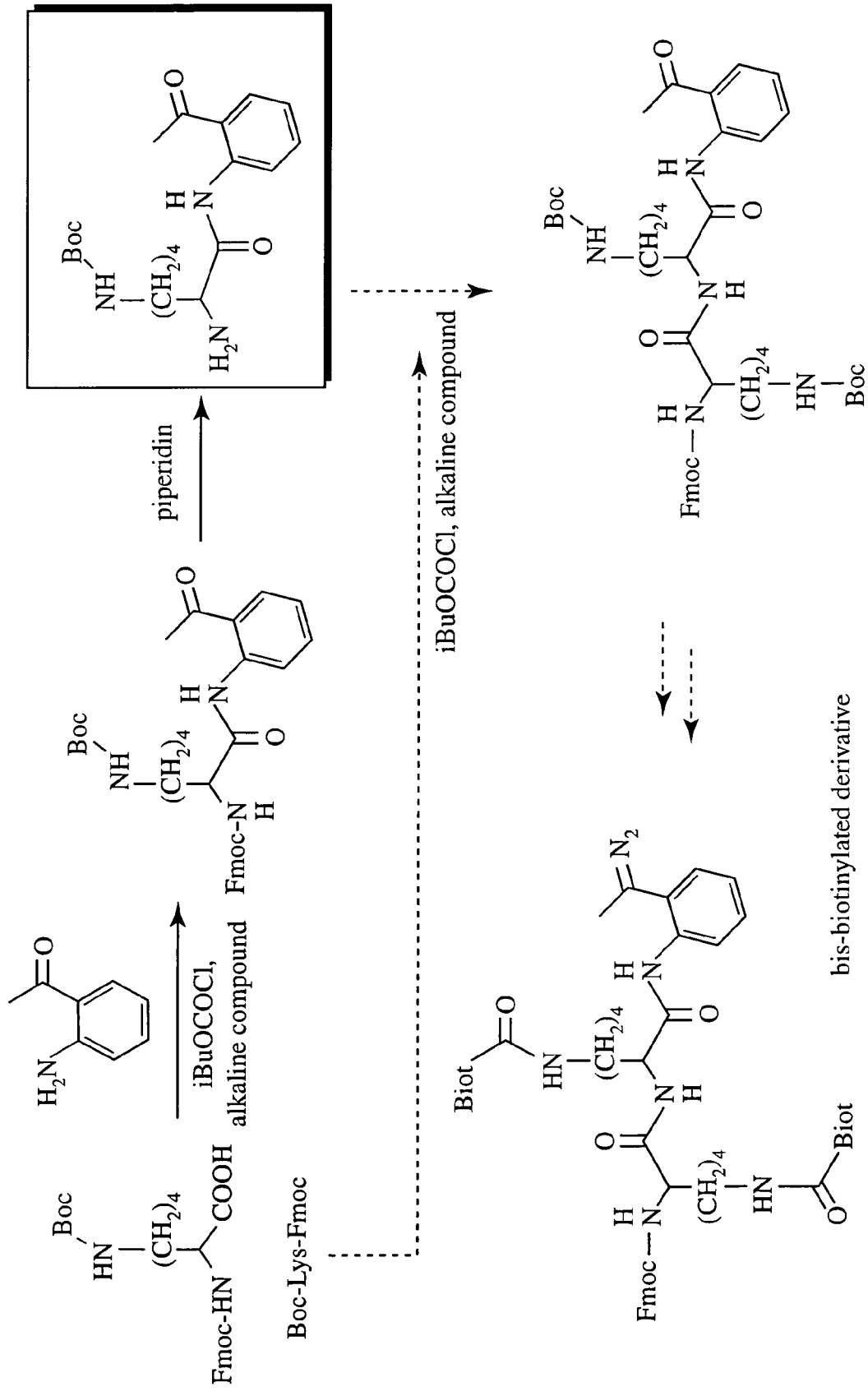

FIG. 6 represents a scheme for the synthesis of a labeling reagent carrying two biotins for the chemical amplification of the signal.

Figure 7:
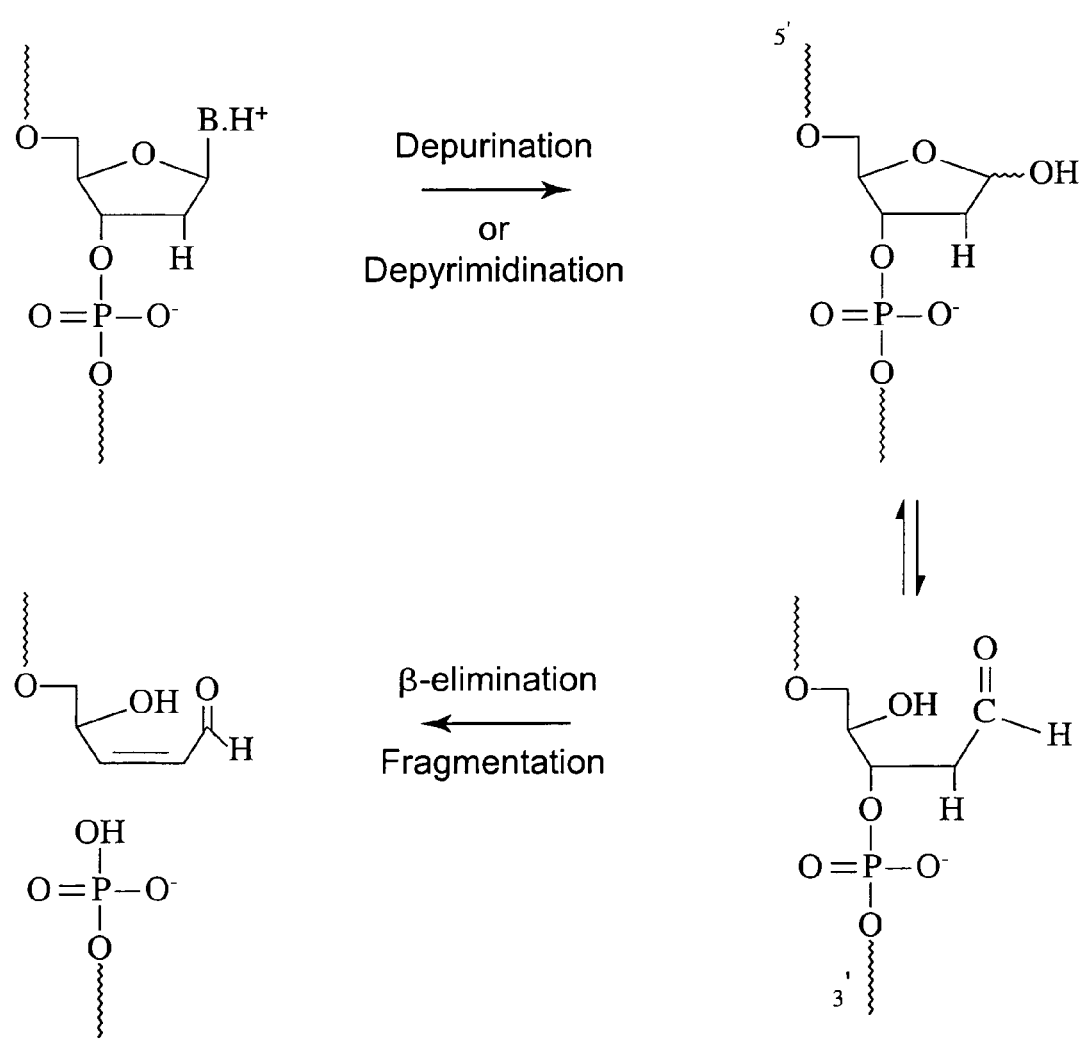

FIG. 7 represents the fragmentation mechanism in acidic medium by the formation of an abasic site.

Figure 8:
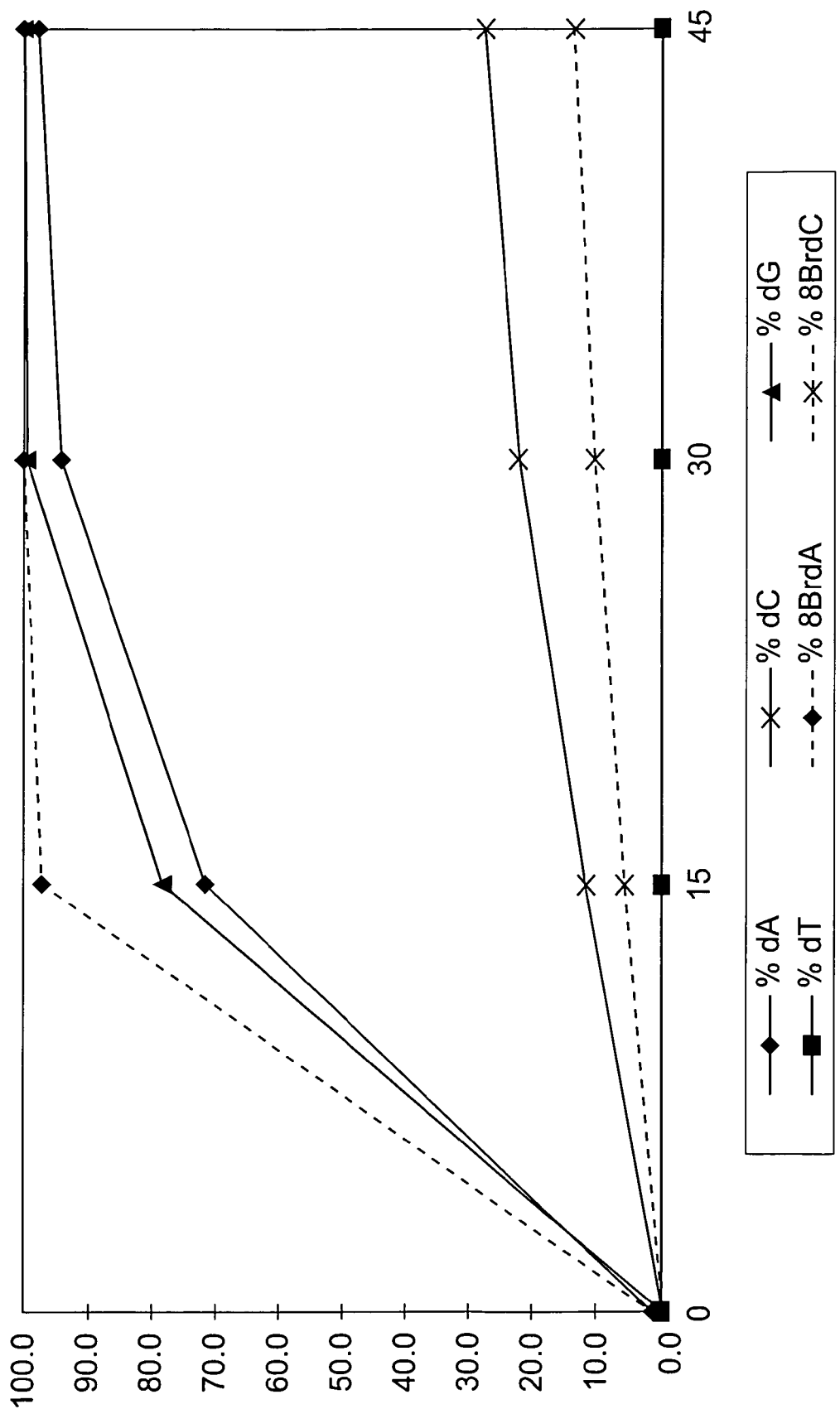

FIG. 8 shows, according to Example 8.1, the kinetics of degradation at acidic pH for various modified nucleosides (8-bromo-2'-deoxyadenosine (8-BrdA) and 5-bromo-2'-deoxyoxycytidine (5-BrdC) as well as the four natural nucleosides (dA, dC, dG and dT). The results are repre sented in the form of percentage hydrolysis of the starting nucleoside (on the y-axis) in relation to the reaction time in minutes (x-axis).

Figure 9:
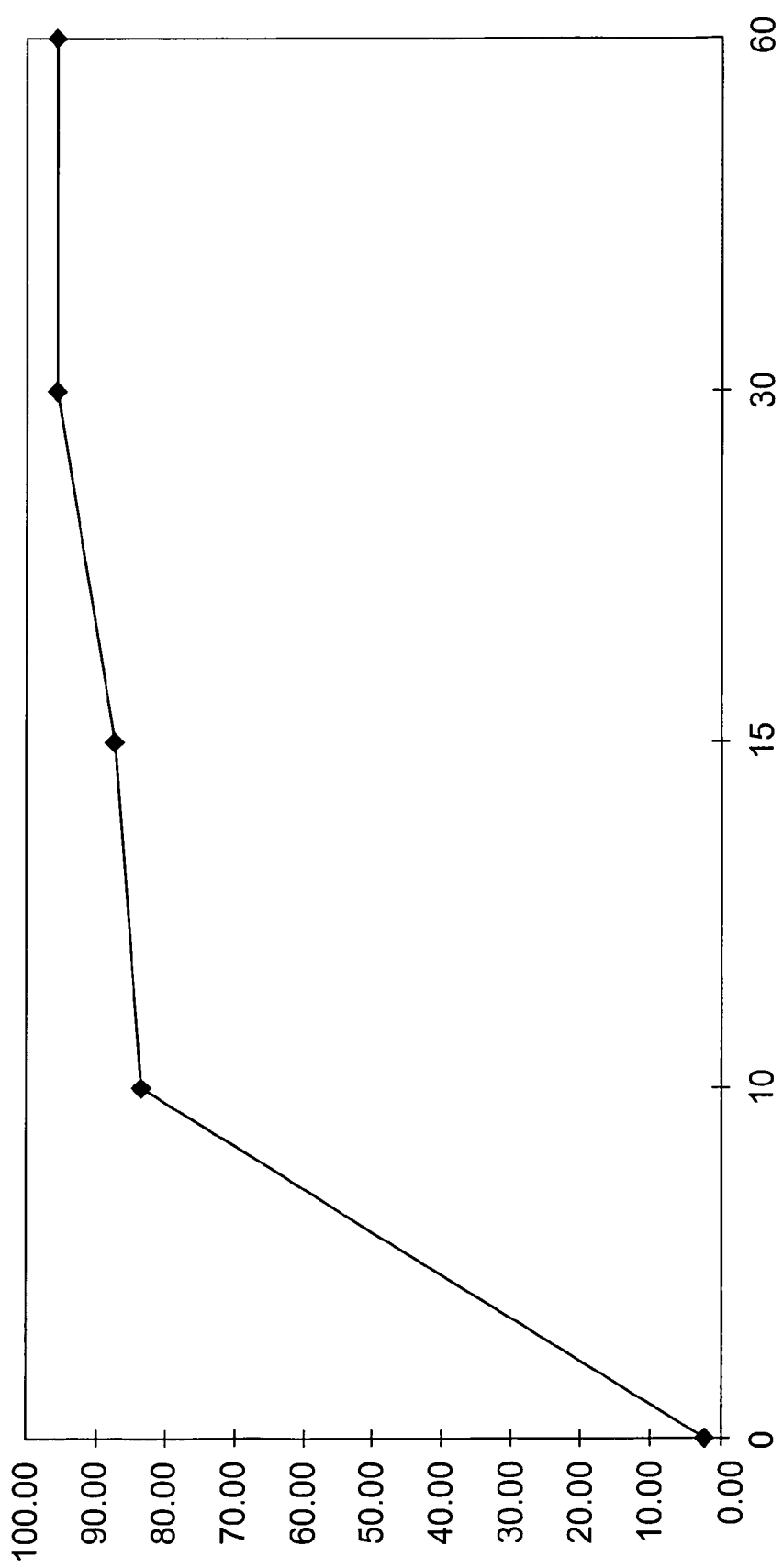

FIG. 9 represents, according to Example 11.2, the kinetics of labeling as a function of time at a temperature of 60° C. with the PDAM reagent on a synthetic ODN 5'-phosphate. The results are represented in the form of percentage labeling in relation to the reaction time expressed in minutes (on the x-axis).

Figure 10:
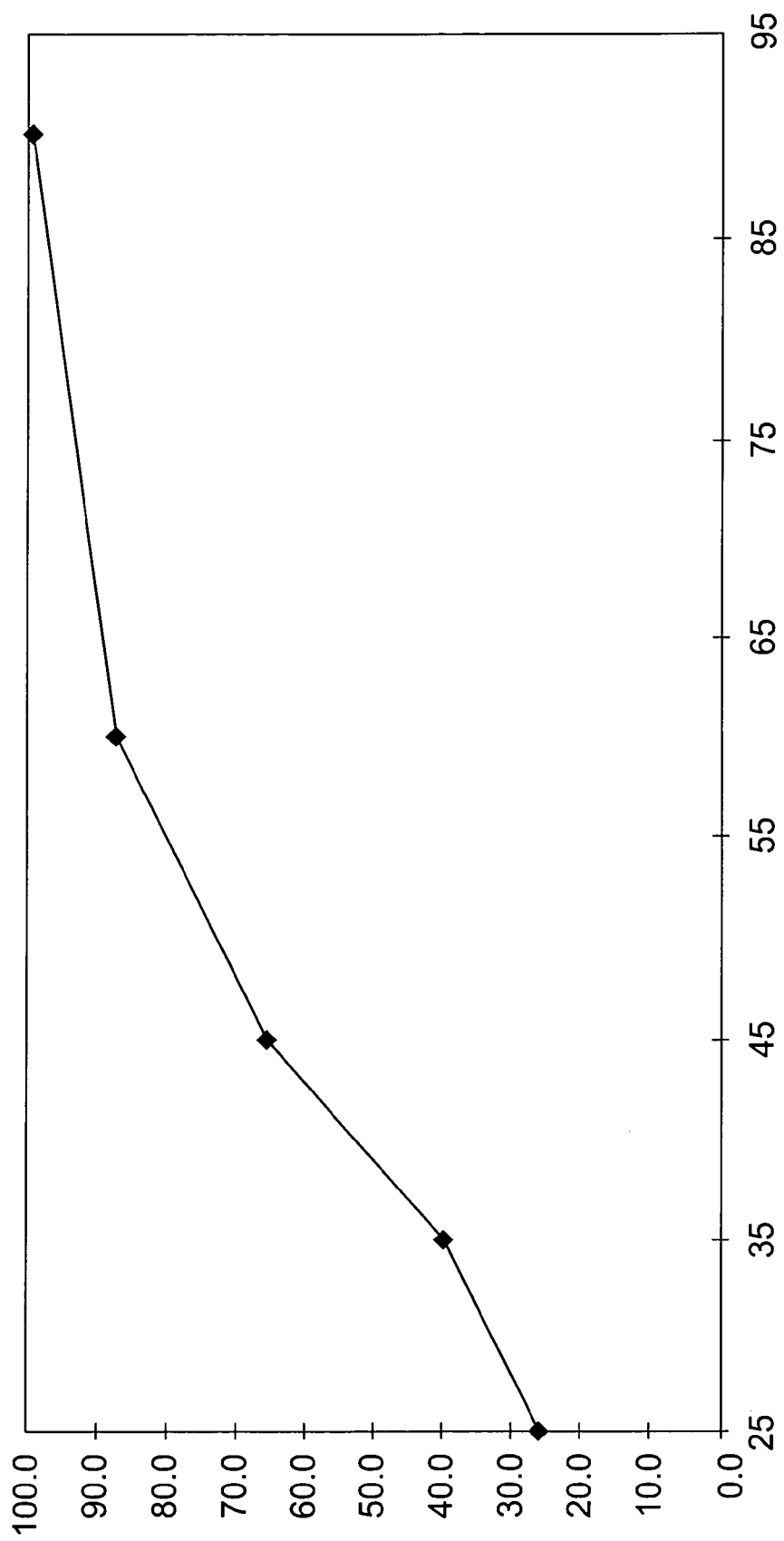

FIG. 10 represents, according to Example 11.3, the percentage labeling as a function of the reaction temperature. The results are presented in FIG. 10 with, on the y-axis, the percentage labeling and, on the x-axis, the reaction temperature in ° C.

Figure 11:
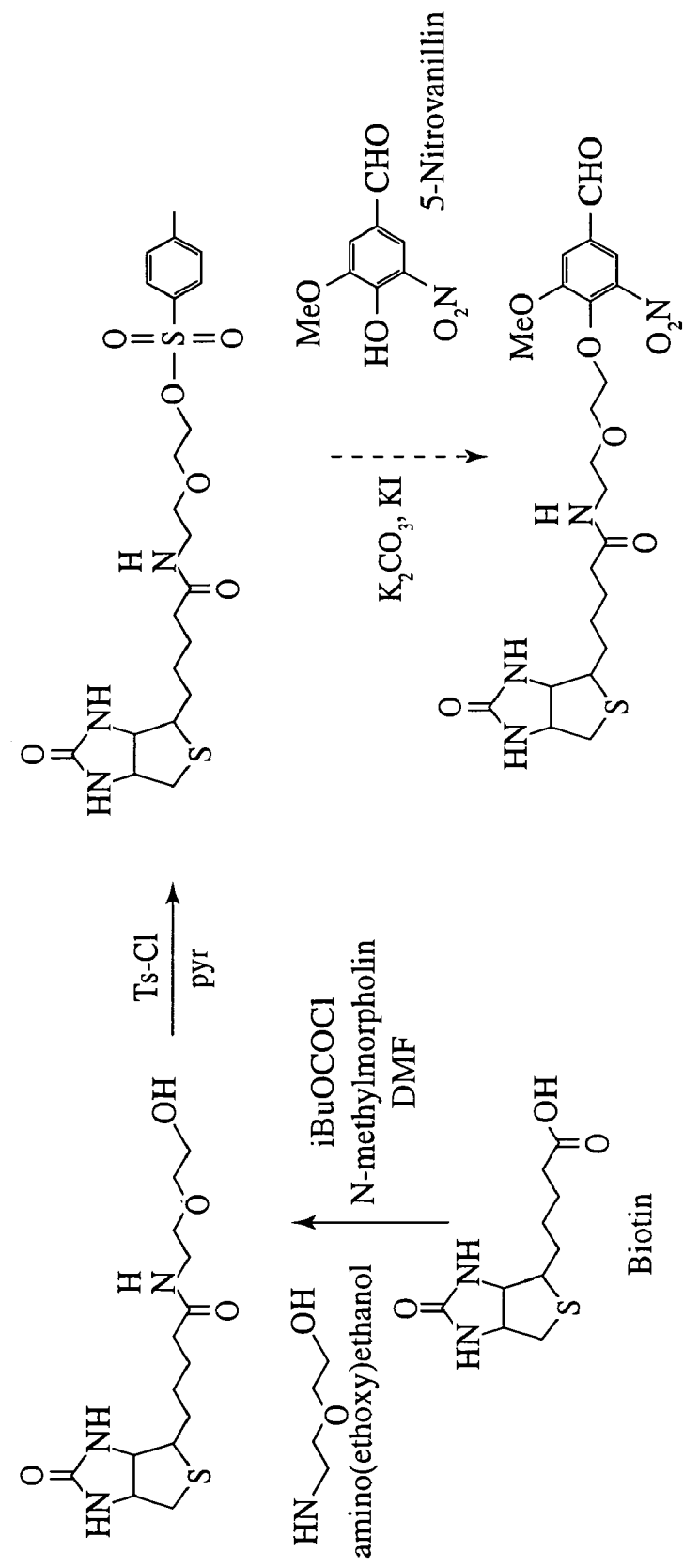

FIG. 11 represents a route of synthesis for a reagent according to formula 4' using the commercial reagent 5-Nitrovanillin. The aldehyde functional group is the precursor of the diazomethyl functional group.

DESCRIPTION OF THE PREFERRED EMBODIMENTS

EXAMPLE 1

Synthesis of Reagents with Biotin

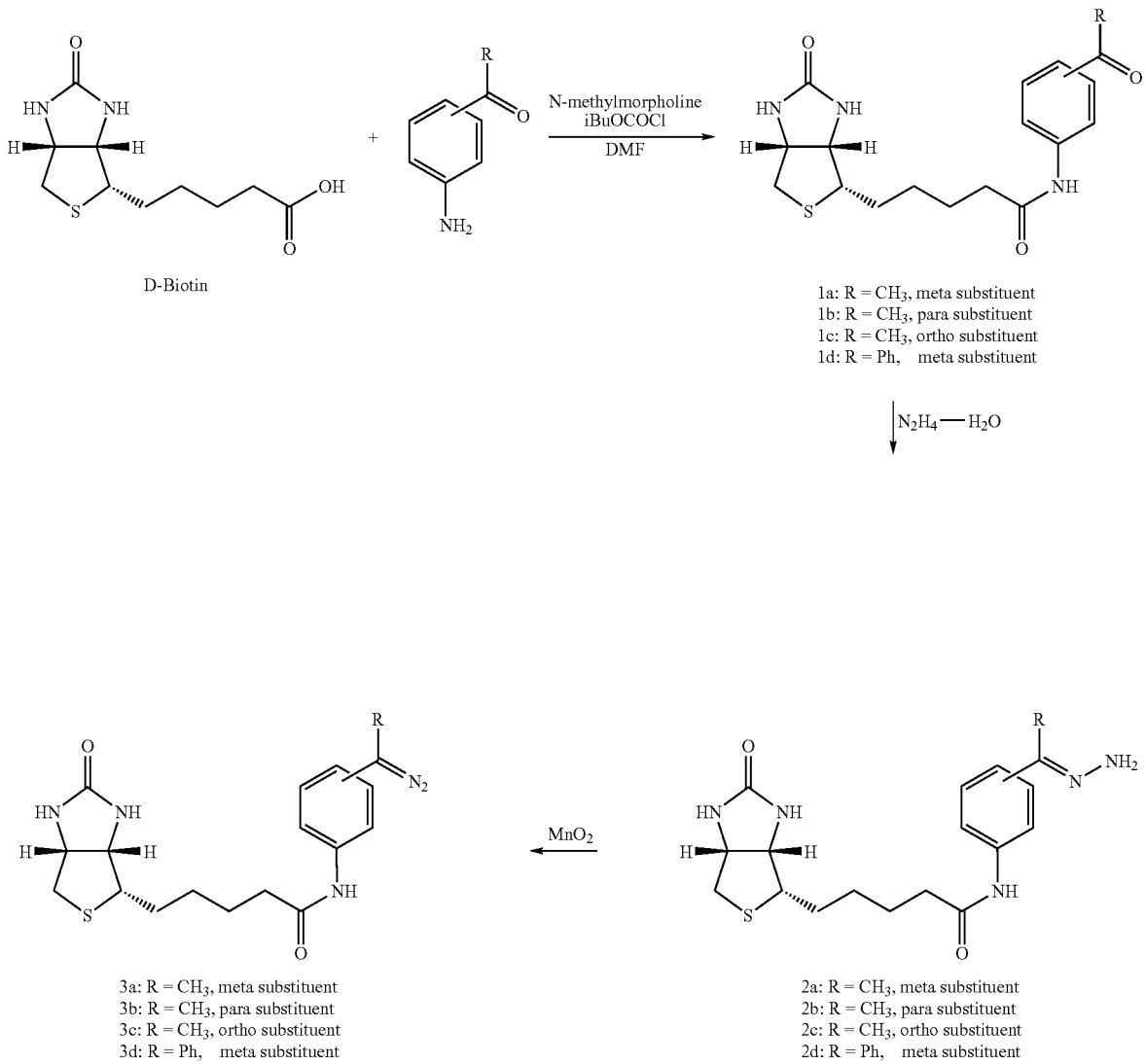

EXAMPLE 1.1

Synthesis of Meta-BioPMDAM:

Compound biotin meta-acetophenone 1a:

The D-biotin (1.0 gram (g), 4.1 millimoles (mmol) is solubilized in 45 milliliters (ml) of anhydrous DMF in the hot state. The mixture is cooled to 0° C. under argon, and then N-methylmorpholine (590 microliters (µl), 5.33 mmol) and isobutyl chloroformate (840 µl, 6.60 mmol) are successively added. The mixture is kept stirred for 30 minutes (min), and then 3-aminoacetophenone (824 mg, 6.10 mmol) and N-methylmorpholine (480 µl, 4.35 mmol) in 10 ml of DMF are added. The solution is maintained stirred at 0° C. for 2 hours (h), and then evaporated to dryness. The residue is taken up in 3 ml of MeOH, and then 50 ml of water are added. The precipitate obtained is filtered, washed with water, $CH_2Cl_2$ and ether to give 1.2 g (80%) of crude product 1a. Recrystallization from the MeOH—$H_2O$ pair gives 1a (1.01 g, 70%) in the form of a white powder.

m.p. 145° C.—IR (KBr): 3280, 2931, 2857, 1691, 1590, 1540, 1487, 1434, 1298, 1266 cm$^{-1}$.—$^1$H NMR (300 MHz, DMSO-d$_6$) δ=1.3–1.7 (m, 6H); 2.33 (t, J=8 Hz, 2H); 2.55 (s, 3H); 2.58; (d, J=12 Hz, 1H); 2.83 (dd, J=12 and 5 Hz, 1H); 3.13 (m, 1H); 4.15 (m, 1H); 4.31 (m, 1H); 6.34 (s, 1H); 6.41 (s, 1H); 7.44 (t, J=8 Hz, 1H); 7.64 (d, J=8 Hz, 1H); 7.85 (d, J=8 Hz, 1H); 8.17 (s, 1H); 10.05 (s, 1H).—MS (FAB/glycerol), m/z: 362 [M+H]$^+$.

Compound meta-hydrazone 2a:

A solution of 1a (500 mg, 1.38 mmol) and of hydrazine monohydrate (200 µl, 4.15 mmol) in absolute ethanol (8 ml) is heated under reflux for 2 h. After cooling to room temperature, the white precipitate is filtered, washed with water, and then with ether and dried. 385 mg (74%) of product 2a are thus obtained in the form of a white powder.

m.p. 185° C.—IR (KBr): 3298, 2931, 2857, 1698, 1665, 1626, 1541, 1494, 1470, 1446, 1330, 1265 cm$^{-1}$.—$^1$H NMR (300 MHz, DMSO-d$_6$) δ=1.3–1.7 (m, 6H); 1.98 (s, 3H); 2.26 (t, J=8 Hz, 2H); 2.56 (d, J=12 Hz, 1H); 2.81 (dd, J=12 and 5 Hz, 1H); 3.11 (m, 1H); 4.13 (m, 1H); 4.29 (m, 1H); 6.39 (s, 3H); 6.42 (s, 1H); 7.22 (m, 2H); 7.50 (d, J=8 Hz, 1H); 7.84 (s, 1H); 9.82 (s, 1H).—MS (FAB/glycerol), m/z: 376 [M+H]$^+$.

Compound meta-diazomethane 3a:

2a (180 mg, 0.48 mmol) is solubilized in 2 ml of DMF. $MnO_2$ (340 mg, 3.9 mmol) is then added. After stirring for 30 minutes at room temperature, the mixture is filtered through a sintered funnel containing celite (thickness: 0.5 cm) and 3 Å powdered molecular sieves (0.5 cm). The reaction mixture is concentrated to a volume of about 0.5 ml, and then 5 ml of ether are added. The resulting precipitate is filtered, washed with water and then dried. Compound 3a (170 mg, 95%) is obtained in the form of a pink powder.

m.p. 160° C.—IR (KBr): 3278, 2935, 2859, 2038, 1704, 1666, 1605, 1577, 1536, 1458, 1430, 1263 cm$^{-1}$.—$^1$H NMR (300 MHz) δ=1.3–1.7 (m, 6H); 2.11 (s, 3H); 2.28 (t, J=8 Hz, 2H); 2.57 (d, J=12 Hz, 1H); 2.81 (dd, J=12 and 5 Hz, 1H); 3.11 (m, 1H); 4.13 (m, 1H); 4.29 (m, 1H); 6.33 (s, 1H); 6.41 (s, 1H); 6.60 (m, 1H); 7.25 (m, 3H); 9.84 (s, 1H).

EXAMPLE 1.2

Synthesis of Para-BioPMDAM

Compound biotin para-acetophenone 1b:

The D-biotin (1 g, 4.1 mmol) is solubilized in 45 ml of anhydrous DMF in the hot state. The mixture is cooled to 0° C. under argon, and then N-methylmorpholine (590 µl, 5.33 mmol) and isobutyl chloroformate (840 µl, 6.60 mmol) are successively added. The mixture is kept stirred for 30 min, and then 4-aminoacetophenone (824 mg, 6.10 mmol) is added. The solution is maintained stirred at 0° C. for 2 h, and then evaporated to dryness. The residue is taken up in 50 ml of water. The precipitate obtained is filtered, washed with water and then with 50 ml of MeOH in the hot state. The white precipitate is dissolved in DMF while heating and then the solution obtained is filtered and washed to with MnOH. The filtrate is recovered and evaporated to dryness to give 888 mg of 1b (2.46 mmol, 60%).

m.p. 260° C.—IR (KBr): 3260, 2930, 2358, 1706, 1673, 1610, 1526, 1401, 1380, 1322, 1257, 1150 cm$^{-1}$.—$^1$H NMR (200 MHz, DMSO-d$_6$) δ=8.82 (s, 1H, NH—CO); 7.57 (d, 2H, J=9 Hz, Ar—H); 6.83 (d, 2H, J=9 Hz, Ar—H); 6.40 (broad s, 1H, NH—CO—NH); 6.32 (broad s, 1H, NH—CO—NH); 4.28 (m, 1H, $CH_2$—CH—NH); 4.12 (m, 1H, CH—CH—NH); 3.11 (m, 1H, CH—S); 2.80 and 2.55 (system ABX, 2H, $^2J_{AB}$=5 Hz, $^3J_{AX}$=12 Hz, $^3J_{BX}$=0 Hz, $CH_2$—S); 2.35 (t, 2H, J=8 Hz, $CH_2$—CO); 2.10 (s, 3H, $CH_3$); 1.60–1.34 (m, 6H, $(CH_2)_3$).

Compound para-hydrazone 2b:

Compound 1b (870 mg, 2.4 mmol) is dissolved in the hot state in ethanol (99%, 8 ml) and then hydrazine monohydrate (995 µl, 19.5 mmol) is added. The solution is heated under reflux for 3 h. The white precipitate obtained is filtered, and washed with ice-cold water. 820 mg (90%) of product 2b are thus obtained in the form of a white powder.

m.p. 305° C.—IR (KBr): 3281, 3183, 2930, 2857, 1698, 1658, 1593, 1521, 1459, 1401, 1325, 1263, 1187 cm$^{-1}$.—$^1$H NMR (200 MHz, DMSO-d$_6$) δ=9.68 (s, 1H, NH—CO); 7.52 (s, 4H, J=9 Hz, Ar—H); 6.43 (broad s, 1H, NH—CO—NH); 6.35 (broad s, 1H, NH—CO—NH); 6.21 (s, 2H, $NH_2$); 4.29 (m, 1H, $CH_2$—CH—NH); 4.12 (m, 1H, CH—CH—NH); 3.12 (m, 1H, CH—S); 2.81 and 2.56 (system ABX, 2H, $^2J_{AB}$=5 Hz, $^3J_{AX}$=12 Hz, $^3J_{BX}$=0 Hz, $CH_2$—S); 2.32 (t, 2H, J=8 Hz, $CH_2$—CO); 1.97 (s, 3H, $CH_3$); 1.63–1.36 (m, 6H, $(CH_2)_3$).

Compound para-diazomethane 3b:

2b (200 mg, 0.53 mmol) is solubilized in 10 ml of DMF. 800 mg of $MnO_2$ are then added. After stirring for 10 minutes, the mixture is filtered through a Celite (0.5 cm)-molecular sieve (0.5 cm in powdered form) mixed layer. The reaction mixture is evaporated to dryness and then washed with ether and dried. Compound 3b (190 mg, 96%) is obtained in the form of a pink powder.

m.p. 180° C. (dec.).—IR (KBr): 3257, 2930, 2857, 2032, 1698, 1597, 1524, 1510, 1455, 1404, 1307, 1259, 1180 cm$^{-1}$.—$^1$H NMR (200 MHz, DMSO-d$_6$) δ=10.18 (s, 1H, NH—CO); 7.88 (d, 2H, J=6 Hz, Ar—H); 7.7 (d, 2H, J=6 Hz, Ar—H); 6.41 (broad s, 1H, NH—CO—NH); 6.34 (broad s, 1H, NH—CO—NH); 4.28 (m, 1H, $CH_2$—CH—NH); 4.12 (m, 1H, CH—CH—NH); 3.11 (m, 1H, CH—S); 2.80 and 2.55 (system ABX, 2H, $^2J_{AB}$=5 Hz, $^3J_{AX}$=12 Hz, $^3J_{BX}$=0 Hz, $CH_2$—S); 2.35 (t, 2H, J=8 Hz, $CH_2$—CO); 2.10 (s, 3H, $CH_3$); 1.60–1.34 (m, 6H, $(CH_2)_3$).

EXAMPLE 1.3

Synthesis of ortho-BioPMDAM

Compound biotin ortho-acetophenone 1c:

The D-biotin (1 g, 4.1 mmol) is solubilized in 45 ml of anhydrous DMF in the hot state. The mixture is cooled to 0° C. under argon, and then N-methylmorpholine (590 µl, 5.33 mmol) and isobutyl chloroformate (840 µl, 6.60 mmol) are successively added. The mixture is kept stirred for 30 min, and then 2-aminoacetophenone (824 mg, 6.10 mmol) is added. The solution is maintained stirred at room temperature for 3 h 30 min, and then evaporated to dryness. The residue is taken up in 50 ml of water. The precipitate obtained is filtered, washed with water and then with 50 ml of MeOH in the hot state. The precipitate obtained is filtered and washed with water. Recrystallization is carried out by dissolving the product in MeOH in the hot state and reprecipitating by addition of water. The precipitate is filtered, washed with water, and then with ether to give 1.1 g (2.95 mmol, 72%) of crude product 1c.

m.p. 150° C.—IR (KBr): 3248, 2930, 2857, 2359, 1691, 1669, 1651, 1582, 1528, 1448, 1354, 1310, 1245, 1161 cm$^{-1}$.—$^1$H NMR (200 MHz, DMSO-$d_6$) δ=11.24 (s, 1H) NH—CO); 8.33 (d, 1H, J=8.5 Hz, Ar—H); 7.97 (d, 2H, J=8 Hz, Ar—H); 7.57 (t, 1H, J=7 Hz, Ar—H); 7.18 (t, 1H, J=7 Hz, Ar—H); 6.44 (broad s, 1H, NH—CO—NH); 6.35 (broad s, 1H, NH—CO—NH); 4.30 (m, 1H, CH$_2$—CH—NH); 4.14 (m, 1H, CH—CH—NH); 3.12 (m, 1H, CH—S); 2.80 and 2.55 (system ABX, 2H, $^2J_{AB}$=5 Hz, $^3J_{AX}$=12 Hz, $^3J_{BX}$=0 Hz, CH$_2$—S); 2.61 (s, 3H, CH$_3$); 2.37 (t, 2H, J=8 Hz, CH$_2$—CO); 1.62–1.38 (m, 6H, (CH$_2$)$_3$).

Compound ortho-hydrazone 2c:

Compound 1c (500 mg, 1.38 mmol) is dissolved in the hot state in ethanol (99%, 8 ml) and then hydrazine monohydrate (572 µl, 11.1 mmol) is added. The solution is heated under reflux for 50 minutes. The solution is evaporated to dryness. The white precipitate obtained is filtered, washed with water and then dried with ether. 416 mg (11.1 mmol, 80%) of product 2c are thus obtained in the form of a white powder.

m.p. 161° C.—IR (KBr): 3412, 3240, 2930, 2857, 2351, 1706, 1677, 1604, 1590, 1531, 1463, 1444, 1372, 1303, 1270, 1169 cm$^{-1}$.—$^1$H NMR (200 MHz, DMSO-$d_6$) δ=11.97 (s, 1H, NH—CO); 8.35 (d, 1H, J=8 Hz, Ar—H); 7.45 (d, 1H, J=7 Hz, Ar—H); 7.19 (t, 1H, J=7.5 Hz, Ar—H); 7.04 (t, 1H, J=7 Hz, Ar—H); 6.61 (s, 2H, NH$_2$); 6.42 (broad s, 1H, NH—CO—NH); 6.35 (broad s, 1H, NH—CO—NH); 4.32 (m, 1H, CH$_2$—CH—NH); 4.14 (m, 1H, CH—CH—NH); 3.12 (m, 1H, CH—S); 2.81 and 2.56 (system ABX, 2H, $^2J_{AB}$=5 Hz, $^3J_{AX}$=12 Hz, $^3J_{BX}$=0 Hz, CH$_2$—S); 2.31 (t, 2H, J=8 Hz, CH$_2$—CO); 2.09 (s, 3H, CH$_3$); 1.63–1.36 (m, 6H, (CH$_2$)$_3$).

Compound ortho-diazomethane 3c:

2c (200 mg, 0.53 mmol) is solubilized in 10 ml of DMF. 800 mg of MnO$_2$ are then added. After stirring for 15 minutes, the mixture is filtered through a Celite (0.5 cm)-molecular sieve (0.5 cm in powdered form) mixed layer. The reaction mixture is evaporated to dryness and then washed with ether and dried Compound 3c (130 mg, 65%) is obtained in the form of a pink powder.

m.p. 110° C.—IR (KBr): 3248, 2930, 2857, 2367, 2342, 2038, 1699, 1521, 1456 cm$^{-1}$.—$^1$H NMR (200 MHz, DMSO-$d_6$) δ=9.37 (s, 1H, NH—CO); 7.26–7.00 (m, 4H, Ar—H); 6.43 (broad s, 1H, NH—CO—NH); 6.35 (broad s, 1H, NH—CO—NH); 4.30 (m, 1H, CH$_2$—CH—NH); 4.15 (m, 1H, CH—CH—NH); 3.12 (m, 1H, CH—S); 2.82 and 2.54 (system ABX, 2H, $^2J_{AB}$=5 Hz, $^3J_{AX}$=12 Hz, $^3J_{BX}$=0 Hz, CH$_2$—S); 2.24 (t, 2H, J=8 Hz, CH$_2$—CO); 2.12 (s, 3H, CH$_3$); 1.63–1.37 (m, 6H, (CH$_2$)$_3$)

EXAMPLE 1.4

Synthesis of meta-BioDPDAM

Compound meta-benzophenone 1d:

The D-biotin (50 mg, 2.05 mmol) is solubilized in 23 ml of anhydrous DMF in the hot state. The mixture is cooled to 0° C. under argon, and then N-methylmorpholine (295 µl, 2.67 mmol) and isobutyl chloroformate (420 µl, 3.28 mmol) are successively added. The mixture is kept stirred for 30 min, and then 3-aminobenzophenone (605 mg, 3.07 mmol) and N-methylmorpholine (240 µl, 2.17 mmol) in 7 ml of DMF are added. The solution is maintained stirred at 0° C. for 2 h, and then evaporated to dryness. The residue is taken up in 1 ml of MeOH, and then 25 ml of water are added. The precipitate obtained is filtered, washed with water and then with ether to give 810 mg (93%) of crude product 1d. Recrystallization from the MeOH—H$_2$O pair gives 1d (630 mg, 72%) in the form of a white powder.

$^1$H NMR (200 MHz, DMSO-$d_6$) δ=10.10 (s, 1H, NH—CO); 8–7.39 (m, 9H, Ar—H); 6.43 (broad s, 1H, NH—CO—NH); 6.35 (broad s, 1H, NH—CO—NH); 4.27 (m, 1H, CH$_2$—CH—NH); 4.13 (m, 1H, CH—CH—NH); 3.12 (m, 1H, CH—S); 2.84 and 2.55 (system ABX, 2H, $^2J_{AB}$=5 Hz, $^3J_{AX}$=12 Hz, $^3J_{BX}$=0 Hz, CH$_2$—S); 2.31 (t, 2H, J=8 Hz, CH$_2$—CO); 1.59–1.36 (m, 6H, (CH$_2$)$_3$).

Compound meta-hydrazone 2d:

1d (350 mg, 0.83 mmol) is solubilized in 5.5 ml of absolute ethanol and then hydrazine monohydrate (140 µl, 2.48 mmol) is added. The solution is heated under reflux overnight. After evaporation, the product is taken up in 1 ml of ethanol and water. The white precipitate is recrystallized: it is dissolved in a minimum of ethanol in the hot state and water is added until a slight cloudiness appears. After cooling, the precipitate obtained is washed with water and then dried with ether. 264 mg (73%) of product 2d are thus obtained in the form of a white powder.

$^1$H NMR (200 MHz, DMSO-$d_6$) δ=9.99 (s, 1H, NH—CO); 9.80 (s, 2H, NH$_2$); 7.54–6.88 (m, 9H, Ar—H); 6.26 (broad s, 1H, NH—CO—NH); 6.21 (broad s, 1H, NH—CO—NH); 4.28 (m, 1H, CH$_2$—CH—NH); 4.13 (m, 1H, CH—CH—NH); 3.12 (m, 1H, CH—S); 2.78 and 2.59 (system ABX, 2H, $^2J_{AB}$=5 Hz, $^3J_{AX}$=12 Hz, $^3J_{BX}$=0 Hz, CH$_2$—S); 2.27 (t, 2H, J=8 Hz, CH$_2$—CO); 1.57–1.36 (m, 6H, (CH$_2$)$_3$).

Compound meta-diazodiphenyl 3d:

3d (500 mg, 0.53 mmol) is solubilized in 1 ml of THF. 80 mg of activated MnO$_2$ are then added. After stirring for 5 minutes at room temperature, the mixture is filtered through a Celite (0.5 cm)-molecular sieve (0.5 cm in powdered form) mixed layer. The reaction mixture is evaporated to dryness. Compound 3d (47 mg, 100%) is obtained in the form of a violet oil.

$^1$H NMR (200 MHz, DMSO-$d_6$) δ=9.95 (s, 1H, NH—CO); 7.60–6.9 (m, 9H, Ar—H); 6.42 (broad s, 1H, NH—CO—NH); 6.35 (broad s, 1H, NH—CO—NH); 4.28 (m, 1H, CH$_2$—CH—NH); 4.14 (m, 1H, CH—CH—NH);

3.12 (m, 1H, CH—S); 2.83 and 2.59 (system ABX, 2H, $^2J_{AB}$=5 Hz, $^3J_{AX}$=12 Hz, $^3J_{BX}$=0 Hz, CH$_2$—S); 2.27 (t, 2H, J=8 Hz, CH$_2$—CO); 1.58–1.35 (m, 6H, (CH$_2$)$_3$).
EXAMPLE 2
Reagent for Labeling with Cy5:Cy5-PMDAM
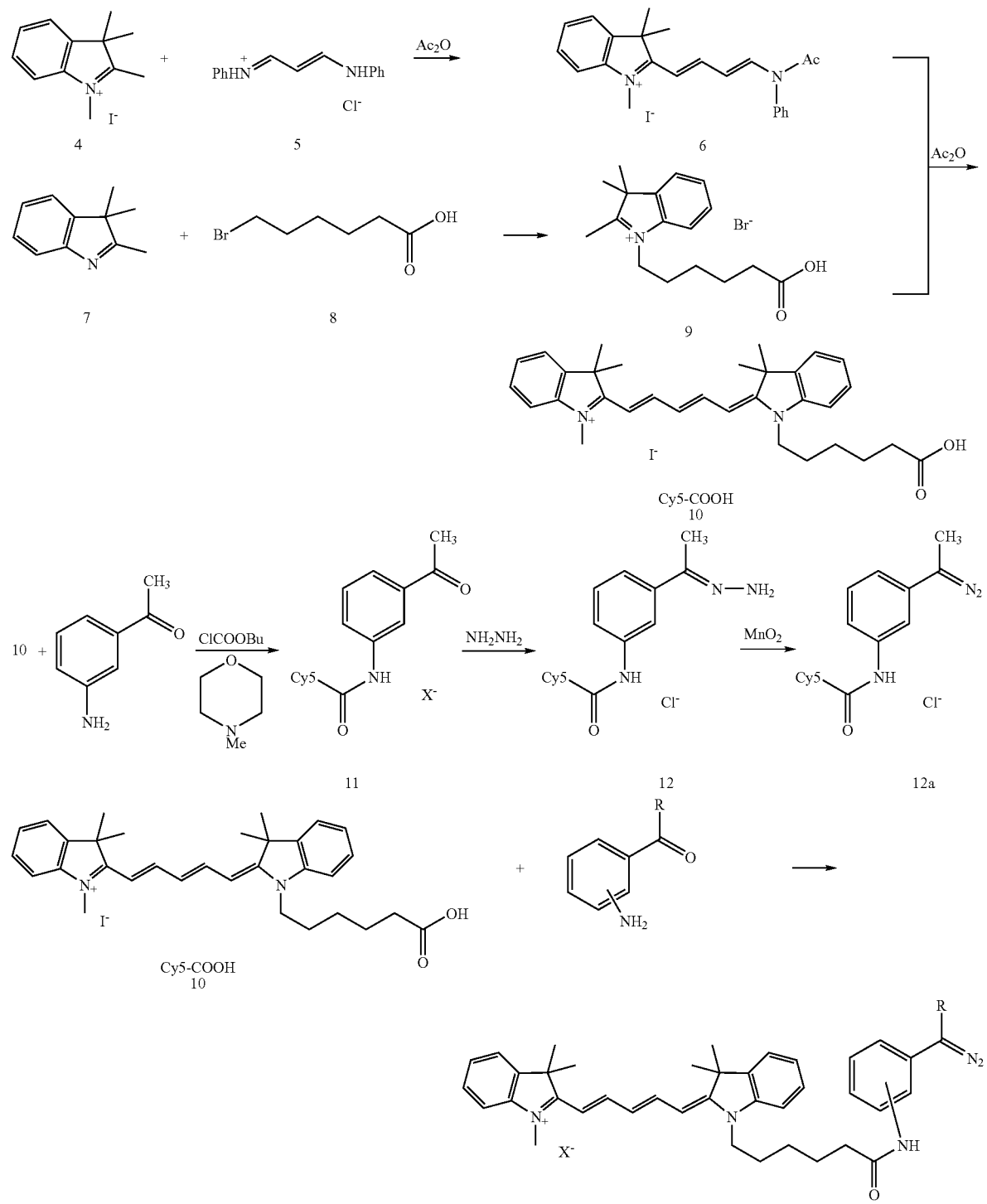

Compound 2-[4-(N-acetyl-N-phenylamino)buta-1,3-dienyl]-1,2,3,3-tetramethyl[3H]indolium Iodide 6:

The mixture of malonaldehydebis(phenylimine) monohydrochloride 5 (18.3 g, 70.0 mmol), NaOAc (9.0 g, 110 mmol) and 1,2,3,3-tetramethyl[3H]indolium iodide 4 (4.25 g; 14.1 mmol) in acetic anhydride (75 ml) is heated at 110° C. for 20 min. After cooling, ether (350 ml) is added and the brown solid which precipitates is filtered, and washed with ether (3×100 ml). The solid is redissolved in 150 ml of $CH_2Cl_2$, filtered (elimination of the inorganic salts) and then evaporated to give a brown solid (6.0 g, 90%).

$^1$H NMR (CDCl$_3$): δ=8.64 (d, 1H, J=12 Hz, 1-H); 8.14 (t, 1H, J=16, 12 Hz, 3-H); 7.63–7.19 (m, 9H); 6.90 (d, 1H, J=15 Hz, 4-H); 5.82 (t, 1H, J=12, 13 Hz, 2-H); 4.06 (s, 3H, NCH$_3$); 2.16 (s, 3H, —COCH$_3$); 1.74 (s, 6H, CH$_3$).

Compound 1-(5-carboxypentyl)-2,3,3-trimethyl[3H]indolium Bromide 9:

2,3,3-Trimethylindole 7 (10.0 g, 62.8 mmol) and 6-bromohexanoic acid 8 (12.3 g, 62.8 mmol) are mixed without solvent and heated at 110° C. for 12 h under argon. The violet-red pasty reaction mixture is washed with ethyl acetate (2×60 ml, the paste is triturated with the spatula and the supernatant is decanted off), and then with acetone (50 ml, the paste solidifies). The pink solid is filtered and then dried under vacuum (16.0 g; 73%).

Compound Cy5COOH 10:

The mixture of the iodide 6 (6.0 g, 12.7 mmol), bromide 9 (4.5 g, 12.7 mmol) and NaOAc (2.6 g, 32 mmol) in acetic anhydride (35 ml) is heated at 110° C. for 20 min. After cooling, ether (150 ml) is added and the precipitate is filtered and washed with ether (3×50 ml). The solid is dissolved in 100 ml of $CH_2Cl_2$, filtered and purified by chromatography on an $SiO_2$ column (eluent: MeOH 5–10%/$CH_2Cl_2$). 3.4 g (44%) are obtained.

$^1$H NMR (CDCl$_3$): δ=8.03 (t, 2H, J=10, 11 Hz, 2-H, 4-H); 7.38–6.91 (m, 9H, Ar—H, 3-H); 6.41 (d, 1H, J=14 Hz, 1-H); 6.31 (d, 1H, J=13 Hz, 5-H); 4.07 (t, 2H, J=7, 7 Hz, α-CH$_2$); 3.68 (s, 3H, NCH$_3$); 2.47 (t, 2H, J=7, 7 Hz, ε-CH$_2$); 1.71 (m, 18H, CH$_3$, β,γ and δ-CH$_2$)—.

Compound for coupling 3-aminoacetophenone with Cy5COOH 10 (product 11):

N-Methylmorpholine (360 µl, 3.2 mmol) is added to a solution of Cy5COOH 10 (1.19 g, 1.9 mmol) in 12 ml of $CH_2Cl_2$. The solution is cooled with an ice bath, and then isobutyl chloroformate (480 µl, 3.7 mmol) is added. After stirring for 5 min, 3-aminoacetophenone (488 mg, 3.6 mmol) is added. The mixture is stirred at room temperature for 3 h. On adding 250 ml of ether, a pasty solid is obtained. After stirring, the solid is allowed to stand at the bottom of the round-bottomed flask and the supernatant is decanted off. 50 ml of ether are again added and the medium is triturated with a spatula to give a solid. The latter is filtered, washed with water, with ether, and then dried under vacuum. The product (iodide) is then dissolved in ethanol, passed over an amberlite IRA900 (Cl$^-$; 15 g) column. The ethanolic solution recovered is evaporated to dryness and then passed over an $SiO_2$ column. 0.93 g (77%) of blue solid is obtained.

Compound Cy5-hydrazone 12:

There is added to a solution of acetophenone 11 (0.93 g, 1.46 mmol) in 5 ml of absolute ethanol hydrazine monohydrate (180 µl, 3.1 mmol) which is stirred at room temperature for 7 h. 50 ml of ether are added and the precipitate is filtered and washed with ether. The crude product is dissolved in 50 ml of $CH_2Cl_2$, the solution is filtered and then concentrated to 10 ml. The product is precipitated by adding 100 ml of ether, filtered, washed with ether and dried under vacuum. 540 mg of product 12 (57%) are obtained.

Compound Cy5PMDAM 12a:

300 mg of $MnO_2$ are added to a solution of 100 mg of hydrazone 12 in 2 ml of DMF, and the mixture is vigorously stirred for 10 min. The suspension is filtered through a layer of celite and washed with DMF (3×500 µl). 50 ml of ether are added and the oil which sediments is triturated with a spatula and the supernatant is decanted off. The washing operation is repeated three times with 25 ml of ether and the solid thus obtained is filtered, and dried. 65 mg (65%) of product 12a are obtained. The purity of the product is about 80–85% ($^1$H NMR).

EXAMPLE 3

Other Reagents Synthesized

EXAMPLE 3.1

Synthesis of Para-Nitrophenyldiazomethane (NPDAM)

4-Nitrobenzaldehyde hydrazone is commercially available (reference 28,118-2, Aldrich, France).

Work is therefore carried out on 600 mg (3.64 mmol) of this product which is dissolved in 9 ml of THF. The solution is kept stirred for 5 minutes and then 1.26 g (4 equivalents, 14.56 mmol) of $MnO_2$ are added with care. The mixture is kept stirred for 10 minutes, and then filtered. The filtrate recovered is evaporated to dryness. After washing with pentane, the compound para-nitrophenyldiazomethane is obtained in the form of a bright orange-colored powder with a yield of 79% (468 mg, 2.87 mmol).

m.p. 80–82° C.—$^1$H NMR (300 MHz, DMSO-d$_6$) δ=8.11 (d, 2H, J=9 Hz, Ar—H$_3$); 7.18 (d, 2H, J=9 Hz, Ar—H$_2$); 6.06 (s, 1H, CH$_1$—N$_2$).

EXAMPLE 3.2

Synthesis of Phenylmethyldiazomethane (PMDAM)

Acetopheneone hydrazone: acetophenone (2.0 g, 16 mmol) is diluted in 16 ml of absolute ethanol and then hydrazine (2.3 ml, 48 mmol) is added. The mixture is heated to reflux temperature. After 2 h, the solvent is evaporated and the residue is taken up in ether (150 ml). The medium is washed with water (100 ml). After drying over Na$_2$SO$_4$, the ether is evaporated off. A pale yellow oil (1.5 g, 11 mmol, 69%) is obtained.

Phenylmethyldiazomethane (PMDAM): hydrazone (150 mg, 1.1 mmol) is dissolved in 3 ml of THF. MnO$_2$ (480 mg, 5.5 mmol) is added. The medium is stirred for 30 min at room temperature. The medium becomes red in color. It is filtered and the solvent is evaporated off. A red oil (145 mg, 100%) is obtained. This reagent is used without purification.

EXAMPLE 3.3

Synthesis of Diphenyldiazomethane (DPDAM)

Benzophenone hydrazone is of commercial origin (reference B 960-2 Aldrich, France).

Work is therefore carried out on 196 mg (1.0 mmol) which are dissolved in 5 ml of THF. 435 mg (5 eq, 5.0 mmol) of MnO$_2$ are added, the mixture is kept stirred for 10 minutes, and then filtered. The filtrate recovered is evaporated to dryness. 193 mg (0.99 mmol) are obtained. This reagent is used without purification.

EXAMPLE 3.4

Synthesis of NVDAM

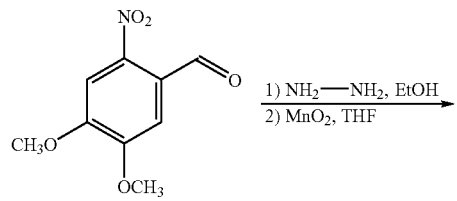

The synthesis is carried out according to the protocol described above, from 6-nitroveratraldehyde (Aldrich, reference 27.960-9).

EXAMPLE 4

Synthesis of the Biotinylated Derivative from NPDAM

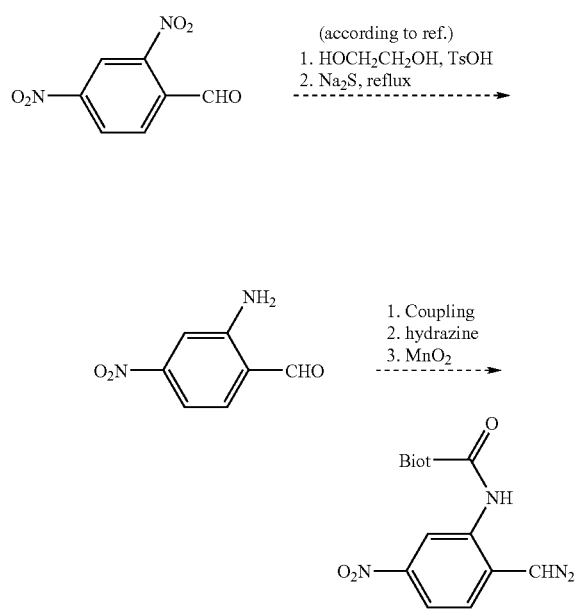

M. E. Wall et al., J. Med. Chem, 1993, 36, 2689.

The 2-amino-4-nitrobenzaldehyde derivative is prepared according to the method of ME Wall et al. referenced above.

The preparation of the diazomethane NPDAM is identical to that described in Example 3.1 above.

EXAMPLE 5

Preparation of the DNA Nucleic Acids

The DNA amplicons are generated by PCR from a 16S *Mycobacterium tuberculosis* genomic DNA target ($10^{+4}$ copies as starting targets) using the Fast Start kit from Roche, 0.2 mM of each deoxyribonucleotide (d-ATP, d-CTP, d-GTP, d-TTP), 0.3 µM of primers and 0.4 µl of enzyme.

The PCR parameters are as follows:
−95° C.: 4 min and then 35 cycles (95° C.:30 sec; 55° C.:30 sec; 72° C.:30 sec) and then 4° C. The amplicons are qualitatively analyzed by agarose gel electrophoresis (1.5%, TBE 0.5×). The volume deposited is 5 µl and the migration takes place for 20 min at 100 volts (V). The visualization of the PCR products is carried out under a UV lamp after staining with ethidium bromide.

The conditions for the culture, the extraction of the Mycobacteria and the amplification primers are given in patent application WO-A-99/65926.

EXAMPLE 6

Reactivity of the Labeling Reagents on Model Nucleotides

The synthesis of the labeling reagents is described in Examples 1 to 4. The PDAM described in the present invention is commercially available (reference P1405, Molecular Probes, Eugene, Oreg.).

EXAMPLE 6.1

Labeling of the Monomers UMP 3'-phosphate

The reactivity of the labeling reagents carrying a diazomethyl functional group was studied in order to control the specificity of the reaction.

A protocol was developed which consists in studying this reactivity by capillary electrophoresis on a model compound 3'-UMP (Uridine 3'-monophosphate, reference U1126 Sigma) under the following standard conditions:

3'-UMP 0.04 mM; $H_3BO_3$ 2.0 mM; 2.0 mM Marker [added with an appropriate organic solvent (THF, AcOEt or DMSO)];

solvents $H_2O$—$CH_3CN$—organic solvent (ratio: 1/3/1).

This solution is divided into ten fractions of 250 µl which are heated to 60° C. After a defined period, each fraction istreated with 250 µl of dichloromethane. After stirring, the organic phase (bottom phase) is removed. This operation is repeated two more times. After centrifugation (5 min, 5000 revolutions per minute (rpm)), the aqueous phase is analyzed by capillary electrophoresis. The capillary electrophoresis (CE) conditions are as follows: CE analysis was carried out by the Beckman P/ACE 5000 apparatus. An untreated fused silica capillary (75 µm×50 cm) was used. The applied voltage is 30 kV (normal polarity) and the temperature of the capillary was maintained at 23° C. The electrophoretograms were recorded at 254 nm. The borate buffer solution (0.1 M, pH 8.3) was prepared from boric acid by adjusting the pH with an NaOH solution and filtered through a 0.2 µm filter. The samples were injected under pressure (0.5 psi, 5 sec). Each analysis is preceded by the regeneration of the capillary by successive passages of an NaOH solution (0.1 M, 2 min), water (2 min) and borate buffer (2 min) under pressure (20 psi).

The reaction is carried out by varying the reaction time between 0 and 4 hours as indicated in each figure and the results are presented for each reagent tested in FIGS. 2A to 2I with the reagent concentration used.

The reaction time is indicated on each electrophoretogram.

With all the reagents tested, the exclusive formation of a monoalkylated product is obtained, which proves the specificity of the reaction.

The reactivity, that is to say the half-reaction time of the reagent with 3'-UMP, may thus be calculated by comparing the height of the peaks, and the results are presented in the table below (standard conditions described above):

TABLE 1

Reactivity (half-reaction time) of the reagents

| Chemical formulae and names | 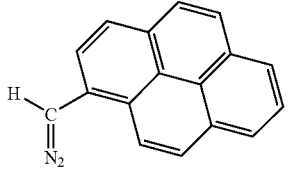 PDAM | 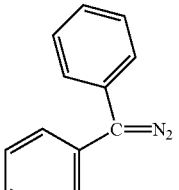 DPDAM | 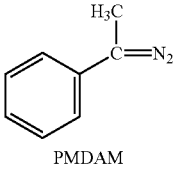 PMDAM | 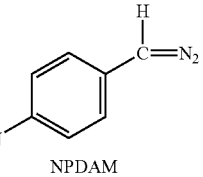 NPDAM |
|---|---|---|---|---|
| Reactivity | 5 min | 20 h | 30 min | 4 h |
| Chemical formulae and names | 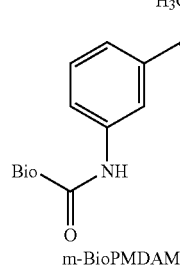 BioDPDAM | 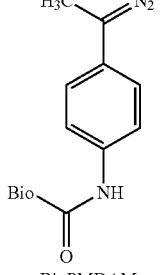 m-BioPMDAM | 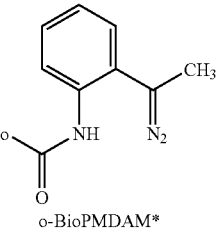 p-BioPMDAM |  o-BioPMDAM* |
| Reactivity | 10 h | 15 min | 5 min | 1 min |

*With o-BioPMDAM, the reactivity is estimated because under the conditions of a 2 mM concentration of labeling reagent, the reaction is complete in less than 5 min. FIG. 2I therefore uses a concentration of 0.2 mM.

It can be noted nevertheless that, since the reaction is very specific and does not lead to by-products for all the reagents tested, it is possible to increase the concentration of the labeling reagent with no consequence from the selectivity point of view on the labeling.

Thus, for the DPDAM reagent, if the concentration is increased to 20 mM (see FIG. 2C), the reactivity (half-reaction time) is 2 hours. The same result is obtained with BioDPDAM (FIG. 2F) where the reactivity is 45 min at a concentration of 30 mM.

EXAMPLE 6.2

Test of Various Nucleotide 3'-monophosphates

In order to avoid any error of interpretation, an additional study on the meta-BioPMDAM marker, taken as a significant example, was carried out with the other nucleotide 3'-monophosphates.

The nucleotides tested are as follows: 3'-AMP (reference 85,194-9 Aldrich), 3'-GMP (reference 151214, ICN), 3'-CMP (reference C1133, Sigma), 3'-TMP (deoxyribo series) (reference T1008, Sigma). The electrophoretograms obtained with the various nucleotides are represented in FIGS. 3A to 3D. The reaction times indicated in FIG. 3A are identical for FIGS. 3B to 3D.

Regardless of the starting nucleotide (ribo or deoxyribo series), the exclusive and complete formation of the alkylated product is observed in 130 min at 60° C. It is important to note that in the case of guanine (the most reactive base with the customary alkylating reagents), only the product alkylated with phosphate is observed, proving the very high selectivity of the reaction.

This study also makes it possible to verify that the rate of the reaction does not depend on the nature of the nucleotide as substrate.

EXAMPLE 6.3

Study of a Dinucleotide

The alkylation of the dinucleotide ApUp (reference A4298, Sigma) was carried out with meta-BioPMDAM in order to verify the selectivity of the reaction toward the terminal phosphate relative to the internucleotide phosphate. The monitoring of the reaction by electrophoresis is represented in FIG. 4. The conditions are the standard conditions of Example 6.1 already described.

The exclusive formation of a single product is observed, showing good selectivity of the meta-BioPMDAM reagent toward the terminal phosphate relative to the internucleotide phosphate.

EXAMPLE 6.4

Characterization of the Adducts with the Four (4) Nucleotide 3'-monophosphates

To ensure that the products obtained indeed resulted from an alkylation with the phosphate, the synthesis of the adducts of the monophosphates 3'-UMP, 3'-CMP, 3'-GMP and 3'-AMP with the meta-BioPMDAM reagent was carried out. The alkylation reaction is carried out on the preparative scale as indicated below. The adducts, obtained with yields of the order of 70%, are purified and then studied by proton or phosphorus NMR.

Preparation Protocol:

3'-UMP (in disodium salt form, 9.3 mg, 21.1 μmol) is dissolved in 2 ml of a 0.1 M aqueous $H_3BO_3$ solution, and then 2 ml of $CH_3CN$, 6 ml of MeOH and then the meta-BioPMDAM reagent (75 mg; 0.20 mmol) are successively added. The reaction is carried out for 2.5 h at room temperature. It is monitored by capillary electrophoresis. 3 ml of water are added, and then the excess reagent is removed by extraction with $CH_2Cl_2$. The aqueous phase is evaporated off. The residue is dissolved in a small quantity of water and purified by passing over a reversed phase silica gel column (Lichroprep RP-18, Merck; elution MeOH/$H_2O$ (20/80)). 10 g (69%) of the adduct of 3'-UMP are obtained.

The proton NMR spectra obtained for the adducts of 3' NMP (N=G, U, C, A) are presented in FIG. 5A to 5D. The identification of the adducts was carried out by two-dimensional $^1H/^1H$ NMR experiments (COSY). Two diastereoisomers for each of these adducts in a 1/1 ratio are present.

Only one peak is present for the phosphorus NMR around 0 ppm (300 MHz, $D_2O$).

These experiments demonstrate that the reaction is indeed specific, that only one adduct is observed and that the labeling indeed takes place on the phosphorus. There is no alkylation side reaction on the bases. The products of labeling are therefore particularly suitable for a hybridization step.

EXAMPLE 7

Study of Temperature Stability

All the diazomethane derivatives described in Table 1 of Example 6.1 above are preserved in the solid state in a freezer at −20° C. for at least 3 months and no loss of reactivity is observed.

The stability at room temperature on the bench was determined by $^1H$ NMR for the two reagents NPDAM and meta-BioPMDAM. We observed no decomposition on leaving NPDAM for one month on the bench with no special precaution. We observed about 50% decomposition on leaving meta-BioPMDAM on the bench for twenty-five (25) days.

The stability of the labeling reagent to temperature is an essential characteristic. Indeed, the final destination of such a reagent for an industrial application is a labeling kit. A reagent which is not stable at least for fifteen (15) days at −20° C., preferably 1 month, is unmarketable. Even if means of storage and of dispatch exist down to −110° C., a relationship exists between the stability at −110° C. and at −20° C. and that is why the value of fifteen (15) days at −20° C., preferably (1) month at −20° C., is an industrial minimum. Beyond −110° C., laboratories do not have the required items of equipment (freezer) for storing these reagents from the point of view of the user and of the manufacturer and there is no simple means of the dry ice type for shipping them from the point of view of the manufacturer.

As regards the stability at room temperature, a stability of a few hours, preferably one (1) day, is sufficient to allow the user to carry out the labeling.

EXAMPLE 8

Study of the Fragmentation of DNA

EXAMPLE 8.1

Hydrolysis of Various Nucleosides in Acidic Medium

The aim of the study is to demonstrate the difference in terms of stability to acidic pH between the natural nucleosides, the modified nucleosides as well as the purine and pyrimidine type nucleosides. This study will also allow us to better control the fragmentation of the DNA by taking into account its base composition.

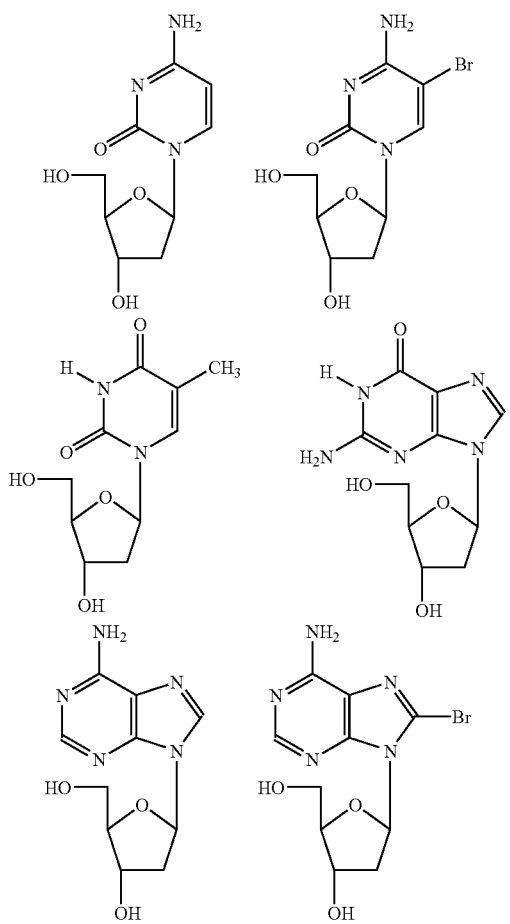

Two modified nucleosides, 8-bromo-2'-deoxyadenosine (8-BrdA) and 5-bromo-2'-deoxycytidine (5-BrdC) as well as the four (4) natural nucleosides (dA, dC, dG and dT) were used in this study.

50 nanomol (nmol) of each nucleoside are incubated in 50 mM sodium formate pH 3 at 95° C. The incubation times vary from 0 to 45 min. After drying under vacuum and taking up in 20 µl of pure water, the samples (10 mmol) are then analyzed by reversed-phase HPLC. The results are given in the form of percentage hydrolysis of the starting nucleoside (on the y-axis) in relation to the incubation time in minutes (x-axis), see FIG. 8.

The curves of FIG. 8 show that the modification of adenine at the 8-position with a bromine atom renders this nucleoside less stable than the natural nucleoside. Moreover, the results show that under the conditions used, depurination is far greater than depyrimidination.

This study shows that the fragmentation of DNA by depurination or depyrimidination can be controlled by optimizing the hydrolysis conditions or by incorporating either modified bases which are less stable than the natural bases or bases which can be modified and hydrolyzed after their incorporation.

EXAMPLE 8.2

Fragmentation of Double-Stranded DNA Incorporating a Modified Nucleotide or Otherwise Three PCR amplifications were carried out in parallel starting with 16S *Mycobacterium tuberculosis* genomic DNA target ($10^{+4}$ initial copies) using the Fast Start kit from Roche, 0.2 mM of each deoxyribonucleotide (d-ATP, d-CTP, d-GTP, d-TTP), 0.3 µM of primers and 0.4 µL of enzyme.

The PCR parameters are those of Example 5.

In the first case, the protocol is used as such: in the case of so-called natural PCR.

In the second case, the protocol is modified in order to obtain a PCR at 30% of 8Br-dATP. This is achieved by introducing 0.2 mM d-CTP, d-GTP and d-TTP. 0.14 mM d-ATP and 0.06 mM 8-BrdATP are also introduced. (8-BrdATP is of commercial origin (reference N-2005-1, TriLink Biotechnologies, San Diego Calif.).)

In the third case, the protocol is modified in order to obtain a PCR at 50% of 8-BrdATP This is achieved by introducing 0.2 mM d-CTP, d-GTP and d-TTP. 0.1 mM of d-ATP and 0.1 mM of 8-BrdATP are also introduced.

The study of the sole fragmentation of these amplicons was carried out under the conditions described above: 50 mM sodium formate pH 3 at 95° C.

The analysis was carried out on a denaturing polyacrylamide gel (8% polyacrylamide, 7 M urea, 1× TBE) using ethidium bromide staining.

After incubating for 15 min at 95° C. in 50 mM sodium formate pH 3, no difference is visible between the three (3) targets. In all cases, we observed complete fragmentation of the PCR amplicons.

The depurination of the PCR amplicons was also carried out at different pH values and at different temperatures and incubation times. Gel analysis, under the above conditions, shows that at pH 3 the fragmentation is complete after only 10 min of incubation at 95° C. At this pH, the fragmentation is also complete at 60° C. after 30 min of incubation.

At pH 4, 30 min of incubation are necessary to obtain complete fragmentation of the DNA amplicons even at 95° C. This result is very important and shows that the abasic site generated at acidic pH is unstable and therefore leads to the fragmentation of the DNA chain without any other particular treatment.

EXAMPLE 9

Labeling and Fragmentation of DNA with the Meta-BioPMDAM Derivative (3a) in Two Steps:

The meta-bioPMDAM derivative (3a) was obtained according to the reaction scheme described in Example 1.1.

The DNA amplicons were prepared by PCR amplification according to the protocol described in Example 5.

Labeling

There are added to 10 µl of PCR, 38 µl of pure water (SIGMA), 50 µl of sodium formate (100 mM in pure water) and the mixture is incubated for 30 minutes at 60° C. Then, 2 µl of meta-bioPMDAM (100 mM DMSO) are added thereafter. The solution was vortexed, and then incubated for an additional 15 min at 60° C.

The trials are carried out in duplicate in order to be able to analyze the fragmentation of the DNA on gel and the labeling efficiency by hybridization and reading of the DNA chip.

Purification

The purification is carried out on QIAQUICK™ columns (Nucleotide Removal kit, Qiagen, Hilden, Germany). The purification protocol used is that recommended by the supplier.

After purification, the eluate is transferred into a clean tube containing 400 µl of hybridization buffer (1.75 ml 20×SSPE; 2.9 ml 5M Betaine; 290 µl 0.1M DTAB; 10 µl Antifoam 30%). The references for these substances are:

Betaine reference B-2754 Sigma, and

DTAB reference D-5047 Sigma.

The solution is vortexed and incubated for 10 min at 95° C. in order to separate the DNA strands which are not separated during the labeling step during the fragmentation (denaturation step). The tube is then immersed in a water-ice mixture at 0° C. before hybridization onto a DNA chip.

Hybridization onto a DNA Chip

After the labeling step during fragmentation, the fragments obtained are hybridized onto the DNA chips designed for analyzing the 213–415 region of the "Genbank" M20940 sequence of the *Mycobacterium tuberculosis* 16S RNA. This DNA chip is described in A. Troesch et al., J. Clin. Microbiol., 37(1), p. 49–55, 1999.

The hybridization steps were carried out on fluidic stations (Affymetrix, Santa Clara, Calif.) using the hybridization protocol and the buffers described in A. Troesch et al., J. Clin. Microblol., 37(1), p. 49–55, 1999. An additional step is necessary to reveal the biotin (indirect detection).

The hybridization is revealed by the coupling of streptavidin labeled with phycoerythrin (PE) which interacts with the biotin of the meta-BioPMDAM under the following conditions: 300 µl of pure water; 300 µl of 100 mM Tris buffer pH 7/1MNaCl/0.05% Tween/0.005% Antifoam; 6 µl of BSA (50 mg/ml); 6 µl of streptavidin-PE (300 µg/ml). The references for these substances are:

Streptavidin-Phycoerythrin: reference R0438, Dako, Denmark,

Streptavidin-CY5: reference C0050 Dako Denmark,

Antifoam reference M5-575, Ultra Additives Inc., and

Tween reference P-7949, Sigma.

Reading of the DNA Chip:

The reading of the fluorescence emitted at the surface of the DNA chip after labeling and hybridization as well as the generation of data in terms of signal intensity and the percentage homology are performed by reading systems and the software provided by Affymetrix (GeneChip® Instrument System and GeneChip® Information System, Santa Clara Calif.).

The reading system provides signal and background noise intensities expressed in rfu (relative fluorescence unit). The percentage homology is given relative to a reference sequence which, in this case, is the *Mycobacterium tuberculosis* sequence.

The results in terms of mean intensity of the signal (I), of the background noise (B) and of the percentage homology (%) are given in Table 2 below.

In general, it is considered that a percentage homology greater than 90% is a satisfactory result although a result greater than 95% is generally sought. Above 95%, the values are no longer indicated because they are not significant in the case of the Mycobacteria DNA chip. A high intensity with a low background noise is the second result sought in the examples which follow. In all the results, the background noise B is deduced from the mean intensity I.

Analysis on Polyacrylamide Gel

The samples intended to be analyzed on gel are dried under vacuum, taken up in 10 µl of pure water and 10 µl of 2× blue formamide.

The migration is performed on an 8% acrylamide gel, in 1×TBE, for 1 hour at 150 V.

Acid pH was used for the fragmentation of the DNA. Indeed, at this pH, the depurination phenomenon generates very unstable abasic sites leading to a practically immediate fragmentation of the DNA sequences at high temperature. This type of fragmentation produces DNA-5' phosphate fragments.

Gel analysis shows that the incubation of the PCR amplicons at 60° C. for 30 min in solution in formate buffer (50 mM, pH 3) leads to a complete fragmentation of these amplicons. This allowed us to evaluate the labeling during the fragmentation of the DNA amplicons in the presence of the meta-bioPMDAM marker.

The labeling results during the fragmentation of the DNA amplicons in terms of percentage homology, intensity of the signals and background noise are given in Table 2 below.

TABLE 2

Labeling and fragmentation of the DNA amplicons in terms of homology, intensity of the signals (I) and background noise (B)

| Conditions for labeling of the PCR amplicons | Homology (%) | I (rfu) | B (rfu) | I/B |
|---|---|---|---|---|
| Buffer: formate pH 3, 50 mM Marker: 2 mM meta-bioPMDAM Incubation: 30 min at 60° C. | >95 | 4456 | 593 | 7.5 |

This example shows that the derivatives of the invention can be used for labeling the DNA fragments produced by enzymatic amplification in a two-step protocol. They can also be used for labeling nonamplified natural DNA.

EXAMPLE 10

Labeling of DNA with the Cy5-PMDAM Derivative (12a)

The labeling of DNA with this new marker carrying the diazomethyl functional group was evaluated using a synthetic DNA fragment.

(12a)

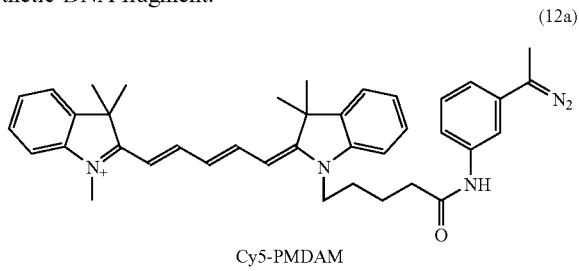

Cy5-PMDAM

The labeling reagent Cy5-PMDAM (12a) is prepared according to the protocol described in Example 2.

A twenty (20) mer oligodeoxyribonucleotide (ODN) is prepared according to the so-called phosphoramidite method. A phosphate is introduced at the 5' end by a standard phosphorylation reagent compatible with the phosphoramidite chemistry. The sequence of this ODN consists of all the natural bases of the DNA (sequence of the ODN: 5'-CT-GAACGGTAGCATCTTGAC-3'). This sequence is complementary to capture sequences of a so-called "model" DNA chip synthesized according to the Affymetrix technology. This DNA chip contains capture probes which are identical in terms of sequence and which show a checkered pattern on its surface. The reading of this DNA chip gives information as to the performance of the labeling in terms of intensity but not of result of homology.

Labeling: to 50 picomol (pmol) of this ODN, 10 μl of Cy5-PMDAM (100 mM in DMSO) are added. The final volume is 100 μl. After homogenization, the incubation is carried out at 60° C. for 30 minutes.

Purification and Reading: The purification, in order to remove the excess labeling reagent, is carried out according to Example 9. The reading on the DNA chip is performed according to Example 17.

Results:

The mean of the labeling intensities (I) read on the DNA chip is 16 644 rfu for a background noise (B) of 450 rfu.

This intensity level is very high and shows that the labeling reagent Cy5-PMDAM (12a) is completely compatible with the labeling of the DNA fragments on the phosphate group.

EXAMPLE 11

Labeling and Fragmentation of DNA with the PDAM Reagent

EXAMPLE 11.1

Labeling with 1-Pyrenyldiazomethane (PDAM)

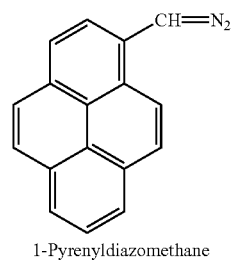

1-Pyrenyldiazomethane

PDAM is obtained from Molecular Probes (Eugene, Oreg.) and solubilized in anhydrous DMSO.

Two ODNs of twenty (20) mers were used as DNA models: one ODN of 20 mer 5'-hydroxyl and the same ODN of 20 mer carrying a phosphate at the 5' end. The sequence of the ODN is described in Example 10. The labeling reaction is carried out in a mixture containing 50% DMSO and 1.5 mM 1-pyrenyldiazomethane (PDAM) at 60° C. for 30 minutes or one hour.

The labeling efficiency was evaluated by thin-layer chromatography (in normal phase) in an isopropanol/ammonia/water 60/10/30 eluent. After 30 minutes, the coupling is complete on the ODN 5'-phosphate. One hour is required to obtain a partial coupling onto the ODN 5'-hydroxyl, that is to say about 50%.

The results of Example 6 are confirmed on a model sequence of 20 bases as regards the very preferential labeling of the reagents carrying a diazomethyl functional group on the terminal phosphate. The labeling on an intranucleotide phosphate is not a damaging inconvenience since it can lead to an increase in sensitivity by introducing more than one marker onto the nucleic acid fragment. This allows the nucleic acid to hybridize with a good sensitivity to the complementary target while preserving a good hybridization specificity.

Persons skilled in the art, by optimization reactions, can thus control the specificity of the labeling by varying, for example, the labeling reagent, the reaction time and the temperature, in order to have exclusive labeling on the terminal phosphate.

EXAMPLE 11.2

Kinetic Study of the Labeling Reaction with PDAM

This study was carried out using the 20 mer ODN 5'-phosphate under the preceding conditions by varying the reaction time. The labeling yields were evaluated by reversed-phase high performance liquid chromatography (HPLC) analysis under the following conditions:

Reversed-phase column Spheri-5 RP-18 5 μm, 220×4.6 mm (Perkin Elmer). The buffers and the gradient used are:

Buffer A: 0.1 M TEAA; Buffer B=50% Buffer A+50% CH$_3$CN, and

Gradient from 10 to 50% of B over 30 min at 1 ml/min at room temperature.

The results are represented in FIG. 9 with, on the x-axis, the reaction time expressed in minutes, and, on the y-axis, the percentage labeling.

The yield is close to 90% after only 10 min of incubation at 60° C.

EXAMPLE 11.3

Effect of the Temperature on the Labeling with PDAM

The labeling was carried out using the 20 mer ODN 5'-phosphate under the preceding conditions by varying the incubation temperature and with an incubation time of 10 min in each case.

The labeling yields were evaluated by reverse-phase HPLC analysis.

The results are presented in FIG. 10 with, on the y-axis, the percentage labeling and, on the x-axis, the reaction temperature in ° C.

It is very important to note that even at room temperature (25° C.), a labeling of the ODN is observed. After 10 min of incubation at 25° C., the labeling yield is about 25%. At temperatures greater than 50° C., yields greater than 80% are obtained.

This shows the efficiency and the flexibility of this chemistry of labeling of DNA with reagents carrying a diazomethyl functional group.

EXAMPLE 12

Labeling and Fragmentation of the DNA Amplicons Obtained by PCR Amplification with the Labeling Reagent Meta-BioPMDAM (3a):

The meta-bioPMDAM derivative (3a) was obtained according to the reaction scheme described in Example 1.1.

The DNA amplicons were prepared by PCR amplification according to the protocol described in Example 5.

EXAMPLE 12.1

Comparison of the Labeling with and Without Fragmentation a. Labeling Under Fragmentation Conditions:

To 10 µl of PCR there are added 50 µl of sodium formate pH 3 (50 mM) and 2 µl of meta-BioPMDAM (100 mM in DMSO). The volume is adjusted to 100 µl. The solution is incubated for 30 min at 60° C.

b. Labeling Without Fragmentation:

To 10 µl of PCR there are added 2 µl of meta-BioPMDAM (100 mM in DMSO). The volume is adjusted to 100 µl. This solution is incubated for 30 min at 60° C.

The rest of the protocol is identical to that of Example 9.

Results

TABLE 3

Comparison of the labeling with and without fragmentation

| Protocol used | Homology (%) | I (rfu) | B (rfu) | I/B |
|---|---|---|---|---|
| a. Labeling under fragmentation conditions | >95 | 3995 | 569 | 7.0 |
| b. Labeling without fragmentation | 94.1 | 500 | 542 | 0.9 |

The results in Table 3 above shows that, without fragmentation, the mean of the intensities obtained is at the same level as the background noise (500 rfu). The labeling during fragmentation gives a much higher intensity level (about 4 000 rfu) and a very good percentage homology. The combination of the two steps therefore indeed represents a significant improvement for the detection of a nucleic acid of length greater than one hundred nucleotides.

EXAMPLE 12.2

Effect of Denaturation Before Hybridization onto a DNA Chip

Two labeling reactions were carried out in parallel in two separate tubes according to the following protocol: to 10 µl of PCR there are added 50 µl of sodium formate buffer pH 3 (50 mM) and 2 µl of meta-bioPMDAM (100 mM in DMSO). The total volume is adjusted to 100 µl and incubated for 30 min at 60° C.

After purification on a column (Example 9), the solution resulting from the first tube is incubated for 10 min at 95° C. (in order to unpair the DNA double strand), and then the tube is immersed in a water-ice mixture at 0° C. until hybridization onto the DNA chip.

The solution resulting from the second tube is hybridized onto the DNA chip without prior denaturation.

The biotinylated fragments hybridized to the capture probes at the surface of the DNA chip are revealed by introducing a streptavidin labeled with phycoerythrin using the conditions described in Example 9.

Results

TABLE 4

Effect of denaturation before hybridization to a DNA chip

| Conditions used | Homology (%) | I (rfu) | B (rfu) | I/B |
|---|---|---|---|---|
| With denaturation | >95 | 22812 | 570 | 40.1 |
| Without denaturation | 93.5 | 4795 | 681 | 7.0 |

The results obtained, presented in Table 4, with the prehybridization denaturation are higher than those obtained without the denaturation step. This shows that the denaturation of the DNA is necessary in order to obtain a good intensity level. Fragmentation via the abasic sites is a means for facilitating the denaturation of a double-stranded DNA and for strengthening the hybridization to the capture probes.

To test other labeling reagents and taking into account the results obtained with the various conditions above, we defined a reference protocol using fragmentation with sodium formate buffer (50 mM, pH 3) and a prehybridization denaturation step.

EXAMPLE 13

Labeling and Fragmentation of the PCR Amplicons with the Biotinylated Reagents in a One-Step Protocol The meta-, ortho- and para-bioPMDAM derivatives were prepared according to the protocol described in Examples 1.1, 1.2 and 1.3. They were solubilized in anhydrous DMSO at a concentration of 100 mM.

The protocol is identical to that of Example 12.2 above (labeling and fragmentation in a single step followed by a prehybridization denaturation step).

Results

TABLE 5

Labeling and fragmentation of the PCR amplicons with the biotinylated reagents in a one-step protocol

| Marker | Homology (%) | I (rfu) | B (rfu) | I/B |
|---|---|---|---|---|
| ortho-bioPMDAM | >95 | 25951 | 820 | 31.6 |
| meta-bioPMDAM | >95 | 22960 | 581 | 39.5 |
| para-bioPMDAM | 94.1 | 43785 | 1205 | 36.3 |

The optimized protocol with fragmentation and labeling in a single step gives excellent results with various labeling reagents containing the reactive diazomethyl functional group, as the results presented in Table 5 show.

EXAMPLE 14

Labeling and Fragmentation of DNA with BioDPDAM

The DNA amplicons were prepared by PCR amplification according to the protocol described in Example 5.

The synthesis of the labeling reagent is described in Example 1.

The protocol is identical to that of Example 12.2 including the denaturation at 95° C. before the hybridization step.

Results

TABLE 6

Labeling and fragmentation of DNA with BioDPDAM

| Marker used | Homology (%) | I (rfu) | B (rfu) | I/B |
|---|---|---|---|---|
| BioDPDAM | 93.0 | 32359 | 3610 | 9.1 |

This result, described in Table 6, shows that substitutions as important as the phenyl group may be used to optimize the reactivity of the labeling reagents carrying a diazomethane functional group.

EXAMPLE 15

Labeling and Fragmentation of DNA with 5-(bromomethyl)fluorescein

The DNA amplicons were prepared by PCR amplification according to the protocol described in Example 5.

To 10 µl of PCR there are added 50 µl of sodium formate pH 3 (100 mM) and 2 µl of 5-(bromomethyl)fluorescein (Molecular probes, Eugene, Oreg.) (100 mM in DMSO). The volume is adjusted to 100 µl. The solution is incubated for 30 min at 60° C.

The purification conditions are in accordance with those of Example 9. A denaturation step is carried out as described in Example 12.2.

The other conditions for hybridization and reading are identical to those described in the article by A. Troesch et al., J. Clin. Microbiol., 37(1), p. 49–55, 1999. The fluorescein is directly detectable on the reader.

TABLE 7

Labeling and fragmentation of DNA with 5-(bromomethyl) fluorescein

| Protocol used | Homology (%) | I (rfu) | B (rfu) | I/B |
|---|---|---|---|---|
| Labeling during the fragmentation of the PCR amplicons with 5-(bromomethyl) fluorescein | >95 | 855 | 183 | 4.7 |

This result from Table 7 shows that the fragmentation of DNA by the creation of abasic sites is completely compatible with a labeling reagent carrying a reactive alkyl halide functional group. This protocol is carried out in one step (fragmentation and labeling) but with intensities that are lower than with markers carrying a diazomethyl functional group.

EXAMPLE 16

Labeling and Fragmentation of the DNA Amplicons in the Presence of Another Chemical Fragmentation Agent Derived from Phenanthroline DNA amplicons were prepared by PCR amplification according to the protocol described in Example 5. Two types of conditions are used Conditions a:

To 10 µl of PCR there are added 20 µl of phenanthroline-$FeSO_4$ (25 mM) and 2 µl of meta-BioPMDAM (100 mM in DMSO). The total volume is adjusted to 100 µl. The mixture is incubated for 60 min at 95° C.

Conditions b:

To 10 µl of PCR there are added 50 µl of sodium formate buffer pH 3 (100 mM in pure water) and 2 µl of meta-BioPMDAM (100 mM in DMSO). The total volume is adjusted to 100 µl. The mixture is incubated for 60 min at 95° C.

The other conditions for the protocol are identical to those of Example 9.

TABLE 8

Labeling and fragmentation of the DNA amplicons in the presence of phenanthroline

| Conditions | Homology (%) | I (rfu) | B (rfu) | I/B |
|---|---|---|---|---|
| Phenanthroline $FeSO_4$ (5 mM) meta-bioPMDAM (2 mM) 60 min at 95° C. | >95 | 2236 | 500 | 4.5 |
| Formate buffer (50 mM) pH 3 meta-bioPMDAM (2 mM) 60 min at 95° C. | >95 | 6786 | 565 | 12.0 |

The two fragmentation conditions allow a satisfactory result as shown in Table 8.

The best result is obtained with conditions (b) using the fragmentation at acid pH.

EXAMPLE 17

Fragmentation of the PCR Amplicons Labeled by Incorporation of d-UTP-fluorescein Incorporation of the Labeled Nucleotide A PCR amplification was carried out according to the following protocol in order to generate PCR amplicons labeled with fluorescein (labeling on the bases).

Starting with 16S *Mycobacterium tuberculosis* genomic DNA target ($10^{+4}$ copies) using the Fast Start kit from Roche, 0.2 mM of the deoxyribonucleotides d-ATP, d-CTP and d-GTP as well as 0.14 mM d-TTP and 0.06 mM dUTP-12-fluorescein, 0.3 µM of primers and 0.4 µl of enzyme. The percentage of labeled nucleotide relative to its natural homolog dUTP is 30%. It is this ratio which is generally used in the reactions for labeling amplicons by incorporation of labeled nucleotides.

The dUTP-12-fluorescein is commercially available from Roche Diagnostics reference 1373242, Mannheim, Germany).

The parameters for the PCR are those of Example 5.

a. Fragmentation of the PCR Amplicons Labeled with 30% of d-UTP-Fluorescein:

To 10 µl of PCR there are added 50 µl of sodium formate buffer pH 3 (50 mM). The volume is adjusted to 100 µl. The solution is then incubated for 30 min at 60° C.

b. Labeling During the Fragmentation of the PCR Amplicons Containing 30% of d-UTP-Fluorescein:

To 10 µl of PCR there are added 50 µl of sodium formate buffer pH 3 (50 mM) and 2 µl of meta-BiOPMDAM (100 mM in DMSO). The volume is adjusted to 100 µl. The solution is then incubated for 30 min at 60° C. This trial corresponds to a reference protocol which makes it possible to compare the various labeling strategies by dispensing with the variability due to the amplification step.

A purification step on a column and a denaturation step at 95° C. are carried out in all cases as in Example 9.

Protocol (a1):

The nucleic acids obtained by fragmentation of the amplicons labeled with d-UTP-fluorescein (conditions a)) are hybridized onto a DNA chip and detected in a first instance by direct reading of the fluorescent signals emitted by the fluorescein as described in Example 15.

Protocol (a2):

A signal amplification step was used to improve the labeling sensitivity. The amplification of the signal was carried out by introducing, during the hybridization step, a biotinylated anti-fluorescein antibody (reference 216-065-084, Jackson ImmunoResearch) and then a streptavidin labeled with phycoerythrin using the following successive conditions:

300 µl of pure water,

300 µl of 100 mM Tris buffer pH 7/1M NaCl/0.05% Tween/ 0.005% Antifoam, 2.4 µl of BSA (50 mg/ml), 1.2 µl of biotinylated anti-fluorescein antibody (1 mg/ml), 300 µl of pure water, and 300 µl of 100 mM Tris buffer pH 7/1M NaCl/0.05% Tween/ 0.005% Antifoam; 6 µl of BSA (50 mg/ml); 6 µl of streptavidin-PE (300 µg/ml).

In this protocol, the fluorescein acts as a hapten (tracer indirectly detectable with a labeled antibody) and not as a fluorophore.

Protocol (b):

The biotinylated fragments (condition b) hybridized onto a DNA chip are revealed by introducing a streptavidin labeled with phycoerythrin using the following conditions:

300 µl of pure water, and

300 µl of 100 mM Tris buffer pH 7/1M NaCl/0.05% Tween/ 0.005% Antifoam; 6 µl of BSA (50 mg/ml); 6 µl of labeled streptavidin-PE (300 µg/ml).

The reading of the fluorescence emitted at the surface of the DNA chip after labeling and hybridization as well as the generation of data in terms of signal intensity and the percentage homology are carried out by the reading systems and the software provided by Affymetrix. In this regard, it is important to note that the reading system used contains two filters which make it possible to directly detect:

fluorescein in the case where the amplicons are labeled with
  d-UTP-fluorescein alone, according to protocol a1, or
  alternatively phycoerythrin in the case where the amplicons are labeled:
  with d-UTP-fluorescein with amplification of the signal, according to protocol a2, or
  with meta-bioPMDAM during their fragmentation, according to protocol b.

In the two cases in which visualization was carried out using phycoerythrin, the use of a filter makes it possible to dispense with the signal generated by fluorescein and it is indeed the phycoerythrin signal which is detected.

Results

TABLE 9

Fragmentation of the PCR amplicons labeled by incorporation of d-UTP-fluorescein

| Protocol used | Marker detected | Homology (%) | I (rfu) | B (rfu) | I/B |
|---|---|---|---|---|---|
| a1. Fragmentation of the PCR amplicons labeled with d-UTP-fluorescein | Flu* | 81.6 | 595 | 342 | 1.7 |
| a2. Fragmentation of the PCR amplicons labeled with d-UTP-fluorescein with amplification of the signal | PE* | >95 | 22107 | 3461 | 6.4 |
| b. Fragmentation and labeling on the same PCR amplicons modified by d-UTP-fluorescein and labeled by meta-BioPMDAM | PE* | >95 | 21700 | 1503 | 14.4 |

*Flu = Fluorescein and PE = Phycoerythrin

The above results of Table 9 show that the chemical fragmentation using the creation of an abasic site is compatible with the enzymatic labeling of the DNA amplicons and that the labeling may take place before the fragmentation.

The intensity levels as well as the percentage homology which are obtained with this protocol for enzymatic incorporation of the fluorophore are low compared with those obtained with the labeling during fragmentation using the labeling reagent with a diazomethyl functional group such as meta-bioPMDAM (conditions (b)).

To reach the intensity level obtained with the meta-bioPMDAM derivative, a step for amplification of the signal is necessary (conditions a2). This indeed shows the efficiency of the diazomethyl reactive functional group relative to the traditional incorporation of modified base such as d-UTP fluorescein (reference protocol (b)).

EXAMPLE 18

Fragmentation of Double-Stranded DNA by Sonication

DNA amplicons were obtained using the protocol described in Example 5. These amplicons were fragmented by sonication in the presence and in the absence of the marker.

a. Labeling of the PCR Amplicons During Sonication:

To 10 µl of PCR reaction there are added 2 µl of meta-BiOPMDAM (100 mM in DMSO). The volume is adjusted to 100 μl with pure water. The pH is adjusted to 6.5. The mixture is incubated for 30 min at 60° C. in a bath of an ultrasound vessel (frequency 35 kHz, model T460-H, Bioblock, France).

b. Labeling During Chemical Fragmentation of the PCR Amplicons (Single-Step Reference Protocol):

To 10 μl of PCR reaction there are added 50 μl of sodium formate pH 3 (50 mM) and 2 μl of meta-BioPMDAM (100 mM in DMSO). The volume is adjusted to 100 μl. The solution is incubated for 30 min at 60° C.

The trials are carried out in duplicate so as to be able to analyze the fragmentation of the DNA on a gel and the efficiency of labeling by hybridization and reading of the DNA chip as described above (Example 9 on phycoerythrin detection).

Analysis on a Gel

The analysis was carried out on a denaturing polyacrylamide gel (8% polyacrylamide, 7 M urea, 1× TBE) using ethidium bromide staining.

Gel analysis shows that the DNA amplicons are fragmented by sonication at 60° C.

Results

TABLE 10

| Fragmentation of double-stranded DNA by sonication | | | | |
|---|---|---|---|---|
| Conditions | Homology | I (rfu) | B (rfu) | I/B |
| a. Labeling during fragmentation by sonication | 93.8 | 2271 | 631 | 3.6 |
| b. Labeling during chemical fragmentation (reference conditions) | >95 | 19639 | 1459 | 13.5 |

The results in Table 10 of labeling during sonication (conditions a) are satisfactory. This shows that physical fragmentation by sonication of the DNA targets is compatible with the chemistry of labeling with labeling reagents carrying a diazomethyl functional group.

The weak labeling results in this case are certainly due to the fact that the marker becomes degraded under the effect of the ultrasound. The results with fragmentation by creation of an abasic site by the action of acidic pH are better.

EXAMPLE 19

Labeling, Fragmentation and Denaturation of DNA in a Single Step

The DNA amplicons were prepared by PCR amplification according to the protocol described in Example 5.

Two labeling reactions were carried out:

a. Labeling, Fragmentation and Denaturation at 95° C. in a Single Step:

To 10 μl of PCR there are added 50 μl of sodium formate buffer pH 3 (50 mM) and 2 μl of meta-bioPMDAM marker (100 mM in anhydrous DMSO). The final volume is adjusted to 100 μl. The solution is then incubated for 30 min at 95° C. In this case, the reaction mixture was hybridized onto a DNA chip without any prior denaturation.

b. Labeling and Fragmentation at 60° C.:

To 10 μl of PCR there are added 50 μl of sodium formate buffer pH 3 (50 mM) and 2 μl of meta-bioDPDAM biotin marker (100 mM in anhydrous DMSO). The final volume is adjusted to 100 μl. The solution is then incubated for 30 min at 60° C. The reaction mixture was then purified according to the protocol described previously. In this protocol and before hybridization onto a DNA chip, the fragments were denatured according to the protocol described in Example 12.2.

Results

TABLE 11

| Labeling, fragmentation and denaturation of DNA in a single step | | | | |
|---|---|---|---|---|
| Protocol used | Homology (%) | I (rfu) | B (rfu) | I/B |
| a. Labeling, fragmentation and denaturation at 95° C. | >95 | 5426 | 506 | 10.7 |
| b. Labeling and fragmentation at 60° C. followed by denaturation at 95° C. | >95 | 7015 | 818 | 6.8 |

Example 12.2 demonstrated the importance of the denaturation of the double-stranded DNA for detection sensitivity. These results in Table 11 show that with the fragmentation approach by creation of an abasic site, the labeling, fragmentation and denaturation of DNA can be carried out in a single step, which represents a notable improvement from the point of view of simplicity and time for the user, without affecting detection sensitivity.

EXAMPLE 20

Synthesis of Para-Bio-EG3-PDAM

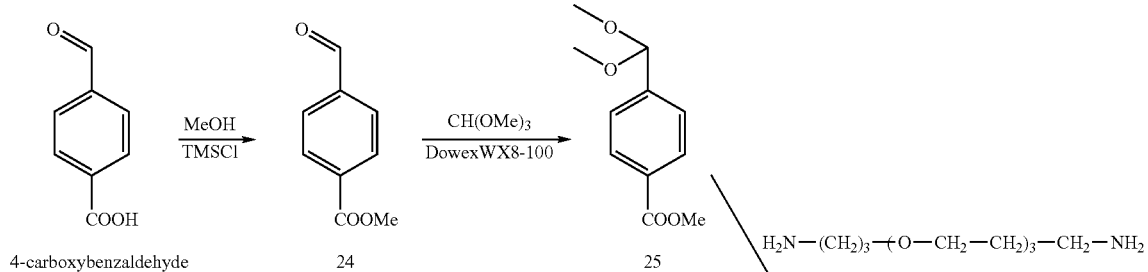

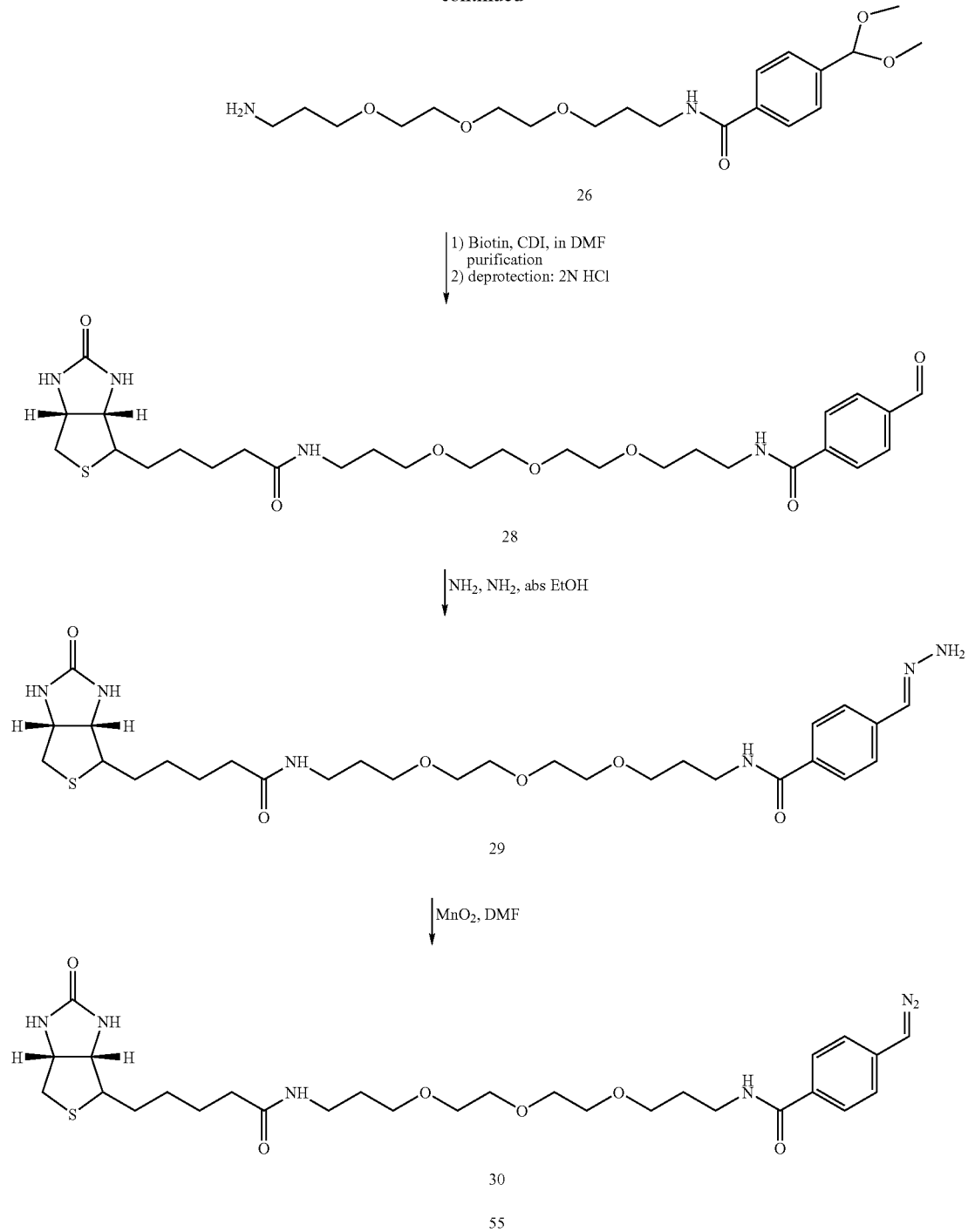

Protection of 4-carboxylbenzaldhyde:

The 4-carboxybenzaldehyde is of commercial origin. It is dissolved (3 g; 20 mmol) in a trimethylsilyl chloride solution (10 g; 92 mmol) in 100 ml of MeOH. The mixture is kept stirred for 40 h at room temperature. After evaporation, a white solid corresponding to 4-methoxycarbonylbenzaldehyde 24 is isolated, characterized by NMR and used as it is for the next reaction.

$^1$H NMR (200 MHz, CDCl$_3$) δ=10.07 (s, 1H, —C$\underline{H}$O); 8.17 (d, 2H, J=8 Hz, Ar—H$_{2,6}$); 7.92 (d, 2H, J=8 Hz, Ar—H$_{3,5}$); 3.93 (s, 3H, CO—O—CH$_3$).

Protection of 4'-methoxycarbonylbenzaldehyde:

The 4-methoxycarbonylbenzaldehyde (3.35 g; 20 mmol) is dissolved with trimethyl orthoformate (4.8 g; 40 mmol) in the presence of Dowex 50WX8-100 (1 g). The mixture is heated under reflux for 2 h, and then filtered and evaporated. After a recrystallization trial, NMR analysis shows that the reaction is not complete and the latter is restarted in 30 ml of MeOH, 30 ml of CH(OMe)$_3$ and 1 g of Dowex 50WX8-100 at room temperature. Filtration and then evaporation are carried out so as to obtain 3.55 g (16.89 mmol, 84%) of product 25.

$^1$H NMR (200 MHz, CDCl$_3$) δ=8.01 (d, 2H, J=8 Hz, Ar—H$_{2,6}$); 7.50 (d, 2H, J=8 Hz, Ar—H$_{3,5}$); 5.41 (s, 1H, CH); 3.93 (s, 3H, —CO—O—CH$_3$); 3.29 (s, 6H, —O—CH$_3$).

Compound 26:

Compound 25 (3.1 g; 14.8 mmol) is solubilized in 16 ml (73 mmol) of 4,7,10-trioxa-1,13-tridecanediamine. The solution obtained is heated at 140–150° C. for 2 h. The mixture is then dissolved in 100 ml of DCM (dichloromethane or CH$_2$Cl$_2$) and washed 6 times with 10 ml of water. The organic phase is dried over MgSO$_4$ and then evaporated until an oil is obtained. This oil is washed with pentane 3 times in succession by decantation, and then a new extraction with DCM and H$_2$O is carried out. After drying over MgSO$_4$ and evaporation, product 26 is isolated with a yield of 63% (9.27 mmol).

$^1$H NMR (200 MHz, CDCl$_3$) δ=7.78 (d, 2H, J=8 Hz, Ar—H$_{2,6}$); 7.46 (d, 2H, J=8 Hz, Ar—H$_{3,5}$); 5.39 (s, 1H, CH); 3.62–3.47 (m, 14H, H$_{7',8',10',11'}$ and H$_{5',13'}$ and H$_{3'}$); 3.29 (s, 6H, —O—CH$_3$); 2.72 (m, 2H, H$_{15'}$) 1.87 (m, 2H, H$_{4'}$); 1.64 (m, 2H, H$_{14'}$); 1.30 (broad s, 2H, NH$_2$).

Biotinylated Compound 27:

Biotin (500 mg; 2.05 mmol) is suspended in 10 ml of DMF then 365 mg (2.25 mmol) of CDI are added. This solution is kept stirred for 30 min at room temperature. Compound 26 (900 mg; 2.26 mmol) is dissolved in 1 ml of DMF, and then added little by little to the preceding solution. The mixture thus obtained is kept stirred for 1 h at room temperature. After evaporation, purification by flash chromatography on a column (column 20 mm in diameter) is carried out with 250 ml of MeOH-DCM 6%, and then with 200 ml of MeOH-DCM 7% and finally 200 ml of MeOH-DCM 8%. The fractions corresponding to product 27 are combined and then evaporated to dryness to give 1.00 g of oil with a yield estimated at 50%.

$^1$H NMR (200 MHz, CDCl$_3$) δ=9.50 (broad s, 1H, NH$_{imidazole}$); 7.80 (d, 2H, J=8 Hz, Ar—H$_{2,6}$); 7.64 (s, 1H, H$_{imidazole}$); 7.46 (d, 2H, J=8 Hz, Ar—H$_{3,5}$ and 1H, NH$_{2'}$); 7.05 (s, 2H, H$_{imidazole}$); 6.76 (t, 1H, NH$_{16'}$), 6.20 (broad s, 1H, NH$_{B1}$); 5.44 (broad s, 1H, NH$_{B3}$); 5.37 (s, 1H, CH); 4.42 (m, 1H, H$_{B6a}$); 4.24 (m, 1H, H$_{B3a}$); 3.59–3.44 (m, 14H, H$_{7',8',10',11'}$ and H$_{5',13'}$ and H$_{3'}$); 3.29 (m, 8H, H$_{15'}$ and 2-O—CH$_3$); 3.07 (m, 1H, H$_{B4}$); 2.84 and 2.66 (system ABX, 2H, $^2J_{AB}$=5 Hz, $^3J_{AX}$=12 Hz, $^3J_{BX}$=0 Hz, H$_{B6}$); 2.13 (t, 2H, J=8 Hz, H$_{B10}$); 1.85 (m, 2H, H$_{4'}$); 1.66 (m, 2H, H$_{14'}$); 1.40–1.37 (m, 6H, H$_{B7, B8, B9}$).

Aldehyde Compound 28:

The acetal 27 is dissolved in 50 ml of chloroform, and then 20 ml of 2N HCl are added. The two-phase mixture is vigorously stirred for 15 min. The organic phase is recovered and dried over anhydrous NaHCO$_3$. It is filtered, evaporated and compound 28 is obtained in the form of a paste (495 mg; 0.855 mmol) with an overall yield of 42% from biotin.

$^1$H NMR (300 MHz, CDCl$_3$) δ=10.05 (s, 1H, CHO); 7.98 (d, 2H, J=8 Hz, Ar—H$_{2,6}$); 7.92 (d, 2H, J=8 Hz, Ar—H$_{3,5}$); 7.58 (t, 1H, NH$_{2'}$); 6.46 (t, 1H, NH$_{16'}$), 6.02 (broad s, 1H, NH$_{B1}$); 5.19 (broad s, 1H, NH$_{B3}$); 4.46 (m, 1H, H$_{B6a}$); 4.27 (m, 1H, H$_{B3a}$); 3.66–3.56 (m, 10H, H$_{7',8',10',11'}$ and H$_{5'}$); 3.50–3.29 (m, 4H, H$_{3',131}$); 3.28 (m, 2H, H$_{15'}$); 2.95 (m, 1H, H$_{B4}$); 2.84 and 2.71 (system ABX, 2H, $^2J_{AB}$=5 Hz, $^3J_{AX}$=12 Hz, $^3J_{BX}$=0 Hz, H$_{B6}$); 2.15 (t, 2H, J=8 Hz, H$_{B10}$); 1.89 (m, 2H, H$_{4'}$); 1.72–1.63 (m, 6H, H$_{14'}$, H$_{B7, B9}$); 1.23 (m, 2H, H$_{B8}$).

Hydrazone Compound 29:

The aldehyde 28 (495 mg; 0.855 mmol) is dissolved in 10 ml of absolute ethanol. Hydrazine (350 μl; 7.20 mmol) is added, and then the reaction mixture is heated under reflux for 1 h. The oil obtained after evaporation is dissolved in abs. EtOH, in order to be evaporated again. A foam is then obtained which is triturated with pentane. The paste corresponding to product 29 (511 mg; 0.862 mmol) is obtained with a yield of 100%.

$^1$H NMR (300 MHz, CDCl$_3$) δ=7.76 (d, 2H, J=8 Hz, Ar—H$_{2,6}$); 7.72 (s, 1H, CH); 7.56 (d, 2H, J=8 Hz, Ar—H$_{3,5}$); 7.34 (t, 1H, NH$_{2'}$); 6.45 (t, 1H, NH$_{16'}$), 5.98 (broad s, 1H, NH$_{B1}$); 5.78 (broad s, 2H, NH$_2$); 5.18 (broad s, 1H, NH$_{B3}$); 4.44 (m, 1H, H$_{B6a}$); 4.26 (m, 1H, H$_{B3a}$); 3.62–3.56 (m, 10H, H$_{7',8',10'',11'}$ and H$_{5'}$); 3.48–3.45 (m, 4H, H$_{3',13'}$); 3.27 (m, 2H, H$_{15'}$); 3.07 (m, 1H, H$_{B4}$); 2.84 and 2.68 (system ABX, 2H, $^2J_{AB}$=5 Hz, $^3J_{AX}$=12 Hz, $^3J_{BX}$=0 Hz, H$_{B6}$); 2.11 (t, 2H, J=8 Hz, H$_{B10}$); 1.86 (m, 2H, H$_{4'}$); 1.72–1.59 (m, 6H, H$_{14'}$, H$_{B7, B9}$); 1.21 (m, 2H, H$_{B8}$).

Diazo Compound 30:

The hydrazone 29 (357 mg; 0.602 mmol) is solubilized in 17.5 ml of DMF. MnO$_2$ (700 mg; 7.7 mmol) is then added. After stirring for 12 min at room temperature, the mixture is filtered on millipore containing celite (thickness: 2 cm) and 3 Å (0.5 cm) powdered molecular sieve. The reaction mixture is evaporated to dryness. The residual oil obtained is washed with ether three times in succession. Compound 30 (290 mg, 0.491 mmol) is obtained in the form of a slightly pink solid with a yield of 82%.

$^1$H NMR (300 MHz, DMSO-d$_6$) δ=8.28 (t, 1H, NH$_{2'}$); 7.77 (d, 2H, J=8 Hz, Ar—H$_{2,6}$); 7.74 (t, 1H, NH$_{16'}$); 7.00 (d, 2H, J=8 Hz, Ar—H$_{3,5}$); 6.38 (broad s, 1H, NH$_{B1}$); 6.32 (broad s, 1H, NH$_{B3}$); 5.80 (s, 1H, CH—N$_2$); 4.27 (m, 1H, H$_{B6a}$); 4.11 (m, 1H, H$_{B3a}$); 3.51–3.44 (m, 10H, H$_{7', 8', 10', 11'}$ and H$_{5'}$); 3.37 (m, 2H, H$_{15'}$); 3.32 (m, 4H, H$_{3',13}$); 3.05 (m, 1H, H$_{B4}$); 2.79 and 2.58 (system ABX, 2H, $^2J_{AB}$=5 Hz, $^3J_{AX}$=12 Hz, $^3J_{BX}$=0 Hz, H$_{B6}$); 2.02 (t, 2H, J=8 Hz, H$_{B10}$); 1.69 (m, 2H, H$_{4'}$); 1.59–1.48 (m, 6H, H$_{14'}$, H$_{B7, B9}$); 1.25 (m, 2H, H$_{B8}$).

The reactivity of compound 30 was tested on uridine 3'-monophosphate and monitored by capillary electrophoresis. The analytical conditions are those of Example 6.1. The results show a half-life period of 45 minutes.

The reagent is stable at −20° C. for at least 1 month.

EXAMPLE 21

Labeling and Fragmentation of DNA Amplicons with the Labeling Reagent Para-Bio-EG3-PDAM The main advantages of this type of molecules, that is to say of PDAM derivatives carrying a polyethylene glycol-based linking arm, are to allow the diazo functional group and the biotin to be kept apart, and to increase the solubility and, in the final analysis, the reactivity of these molecules.

The para-Bio-EG3-PDAM derivative 30 was obtained according to the reaction scheme described in Example 20. The DNA amplicons were prepared by PCR amplification according to the protocol described in Example 5. Two labeling reactions were carried out.

a. Labeling with the Para-Bio-EG3-PDAM Reagent:

To 10 μl of PCR there are added 10 μl of para-Bio-EG3-PDAM (100 mM in DMSO) and 77 μl of DNase/RNase-free water. The solution is homogeneous and has no precipitates. This solution is incubated for 10 min at 95° C., and then 3 μl of 0.1M HCl are added and the solution is incubated for 10 min at 95° C.

The remainder of the protocol is identical to that of Example 8.

b. Labeling with the Meta-BioPMDAM Reagent:

To 10 μl of PCR there are added 10 μl of meta-BioPMDAM (100 mM in DMSO) and 77 μl of DNase/RNase-free water. The synthesis of this product is mentioned in Example 1.1. The solution has a slight precipitate. This solution is incubated for 10 min at 95° C. 3 μl of 0.1M HCl are then added and the solution is incubated for 10 min at 95° C.

The remainder of the protocol is identical to that of Example 8.

Results:

TABLE 12

Comparative study of the labeling and fragmentation of DNA amplicons with para-Bio-EG3-PDAM and meta-BioPMDAM

| Protocol used | Homology (%) | I (rfu) | B (rfu) | I/B |
|---|---|---|---|---|
| a. Labeling with the para-Bio-EG3-PDAM reagent | >95% | 15151 | 621 | 24.4 |
| b. Labeling with the meta-BioPMDAM reagent | >95% | 11226 | 515 | 21.8 |

The signal intensities obtained in this Table 12 are very satisfactory and the percentage homology is high. This result shows that the introduction of a polyethylene glycol arm onto the diazo labeling molecule makes it possible to increase the aqueous phase solubility of the reagent. The test is therefore homogeneous. Furthermore, the increase in solubility makes it possible to increase the reactivity of the marker.

EXAMPLE 22

Synthesis of Other PDAM Derivatives Comprising a Polyethylene Glycol-Based Linking Arm

EXAMPLE 22.1

Synthesis of Meta-Bio-EG3-PMDAM

Synthesis scheme

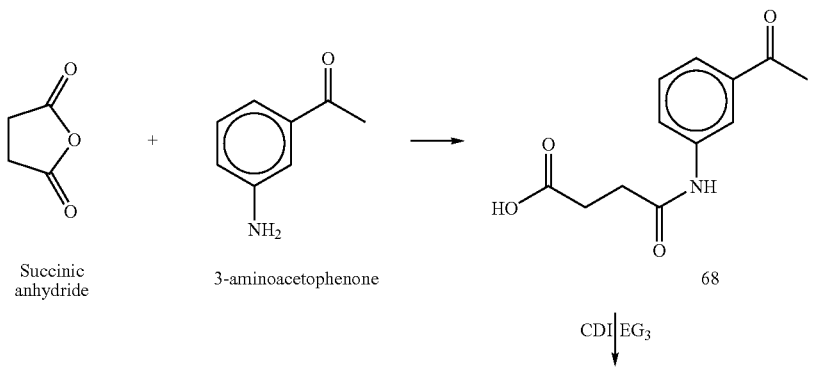

Succinic anhydride    3-aminoacetophenone    68

CDI | EG₃

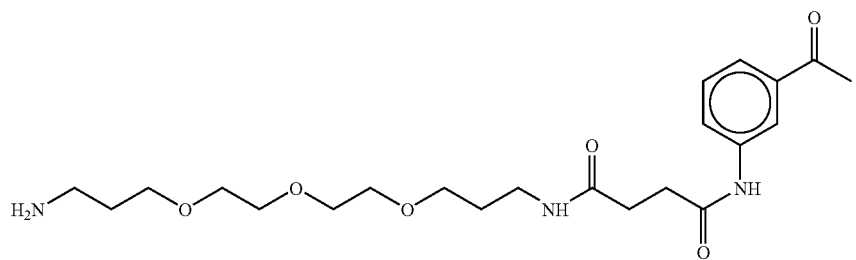

69

CDI | D-biotin

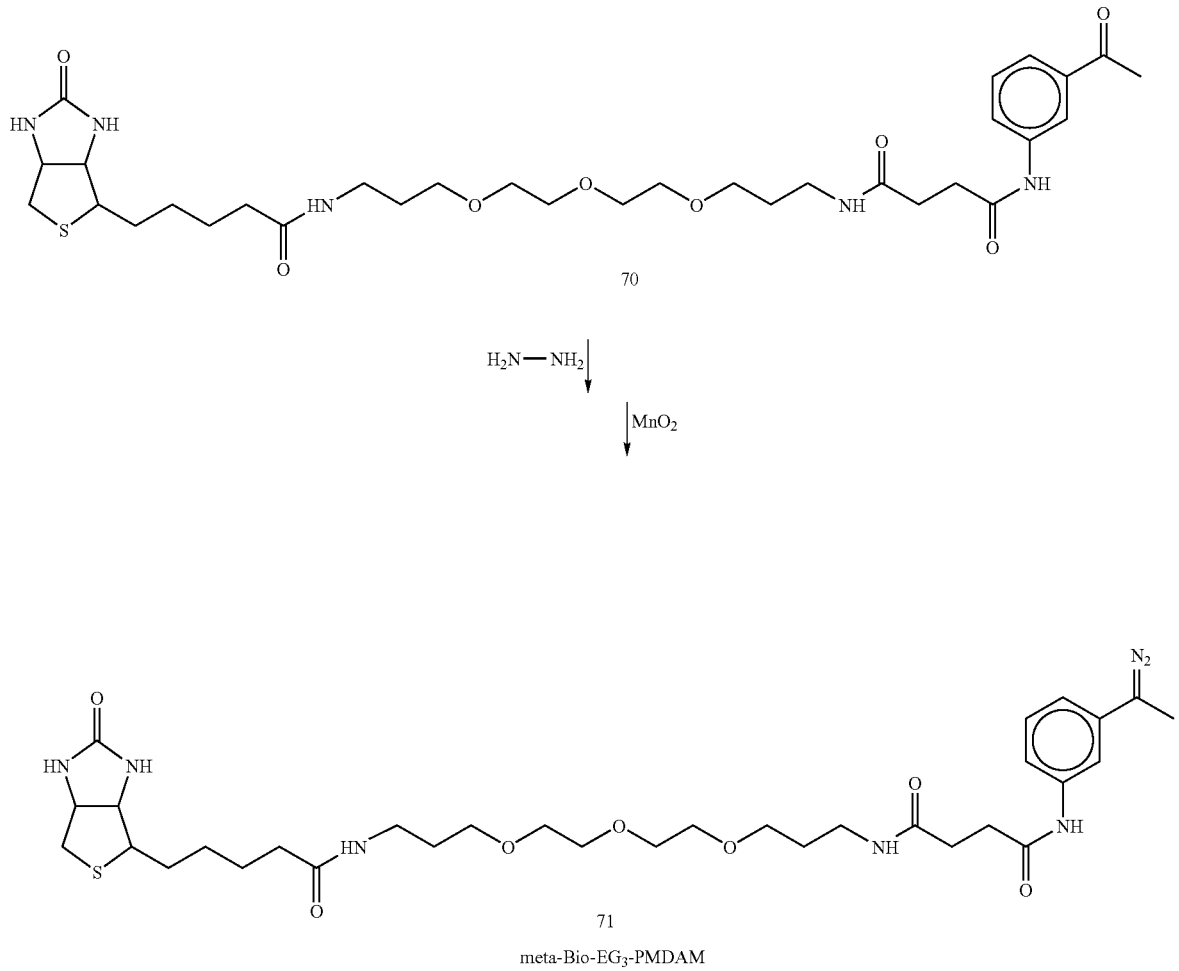

meta-Bio-EG$_3$-PMDAM

Compound 68:

3-Aminoacetophenone (14.5 g, 107 mmol) is solubilized in 50 ml of anhydrous DMF. Succinic anhydride (10.7 g, 107 mmol) is added and the mixture is kept stirred, under argon and at room temperature. After 6 h, the solution is concentrated under vacuum and 50 ml of methanol are added. The precipitate obtained is filtered and washed with methanol and ether. 19.4 g (81%) of product 68 are thus obtained in the form of a powder which is off-white in color.

$^1$H NMR (200 MHz, DMSO-d$_6$) δ=2.5–2.6 (m, 7H); 7.45 (t, 1H); 7.64 (d, 1H); 7.83 (d, 1H); 8.19 (s, 1H); 10.16 (s, 1H); 12.12 (s, 1H).

Compound 69:

5.07 g (22 mmol) of compound 68 are solubilized in 10 ml of anhydrous DMF, under argon. The mixture is placed on ice and 5.00 g (32 mmol) of carbonyldiimidazole are added. After 20 min, 20 ml (94.6 mmol) of 4,7,10-trioxatridecanediamine (EG$_3$) are slowly added. After 3 h of reaction at room temperature, the DMF is evaporated and the residue is taken up in 100 ml of CH$_2$Cl$_2$. Extractions are carried out with saturated NaHCO$_3$ and H$_2$O, after which the organic phase is dried with anhydrous Na$_2$SO$_4$ and the solvent evaporated. 4.34 g (46%) of product 69 are thus obtained.

$^1$H NMR (200 MHz, DMSO-d$_6$): δ=1.59 (m, 2H); 1.87 (m, 2H); 2.16 (s, 3H); 2.40 (m, 2H); 2.55 (m, 2H); 3.08 (m, 2H); 3.45 (m, 16H); 7.30 (t, 1H); 7.42 (d, 1H); 7.70 (d, 1H); 7.83 (t, 1H); 7.97 (s, 1H); 10.00 (s, 1H).

Biotinylated Compound 70:

D-biotin (1.0 g, 4.1 mmol) is solubilized in 10 ml of anhydrous DMF, under argon. The mixture is cooled on ice and carbonyldiimidazole (CDI) (0.665 g, 4.1 mmol) in 10 ml of anhydrous DMF is added. After 15 min, compound 69 (1.8 g, 4.1 mmol) in 2 ml of anhydrous DMF is added. The reaction is allowed to proceed for 3 h at 35° C., and then the DMF is evaporated and the residue is taken up in 100 ml of CH$_2$Cl$_2$. Extractions are carried out with saturated NaHCO$_3$ and H$_2$O, after which the organic phase is dried over anhydrous Na$_2$SO$_4$ and the solvent evaporated. NMR characterization of the product thus obtained shows that a mixture of product 70 and of free EG$_3$ is obtained. Another purification step is carried out before continuing the synthesis.

The final compound, meta-Bio-EG$_3$-PMDAM, is obtained after two synthesis steps according to the scheme described in Example 1.

The advantage of this synthesis is two-fold. On the one hand, product 69 is obtained in only two steps; this product of may be used as a precursor of the diazo with the possibility attaching thereto detectable molecules of a different nature, by means of the terminal amine group. This group also makes it possible to graft compound 69 onto solid supports, with the objective of immobilizing nucleic acids. On the other hand, compound 71 possesses the same reactive center as meta-Bio-PMDAM (our reference molecule), which facilitates the analysis of the advantages linked to the inclusion of the ethylene glycol (EG$_3$) arm.

The reagent is stable at −20° C. for at least 1 month.

EXAMPLE 22.2

Synthesis of meta-Bio-EG4-PMDAM

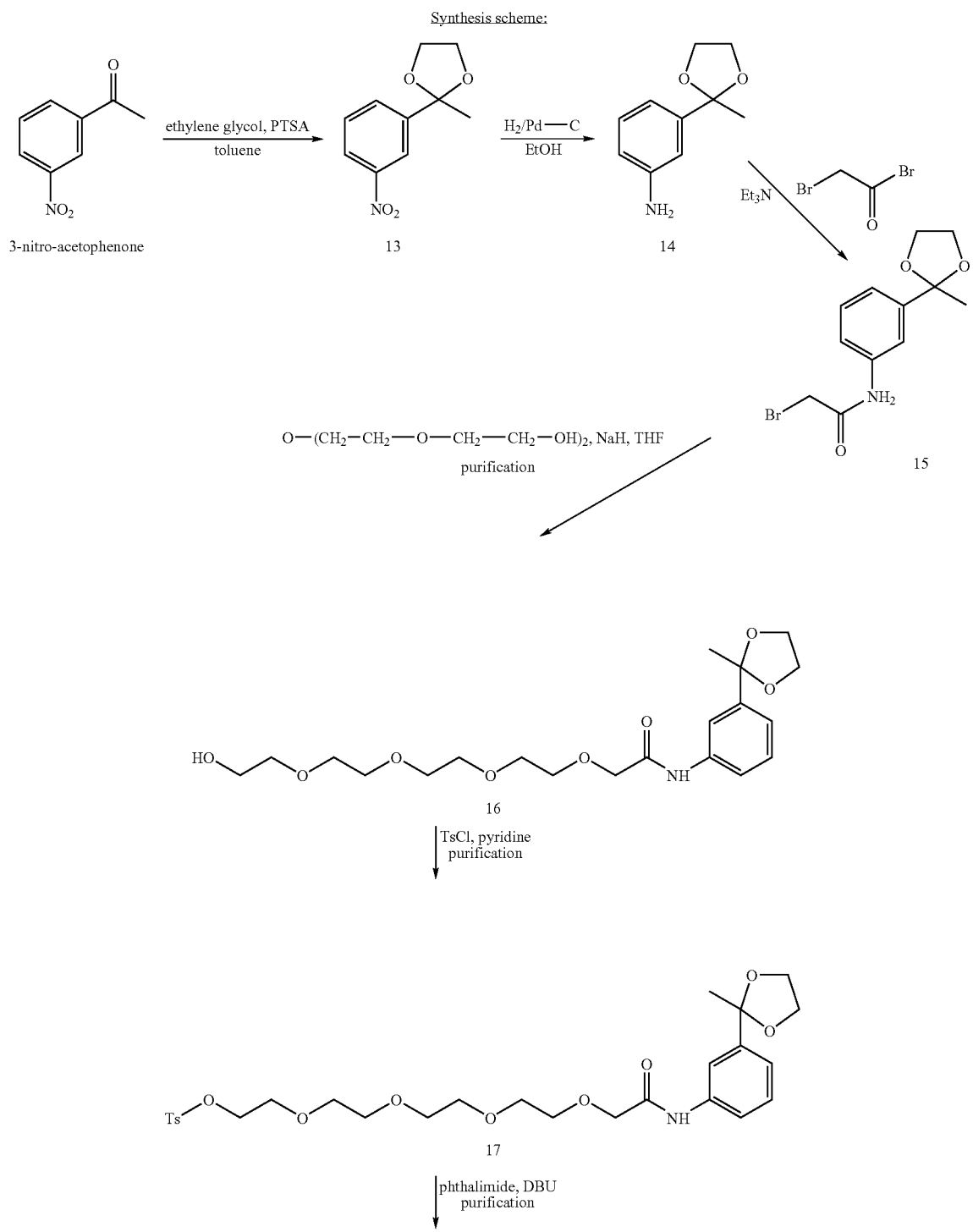

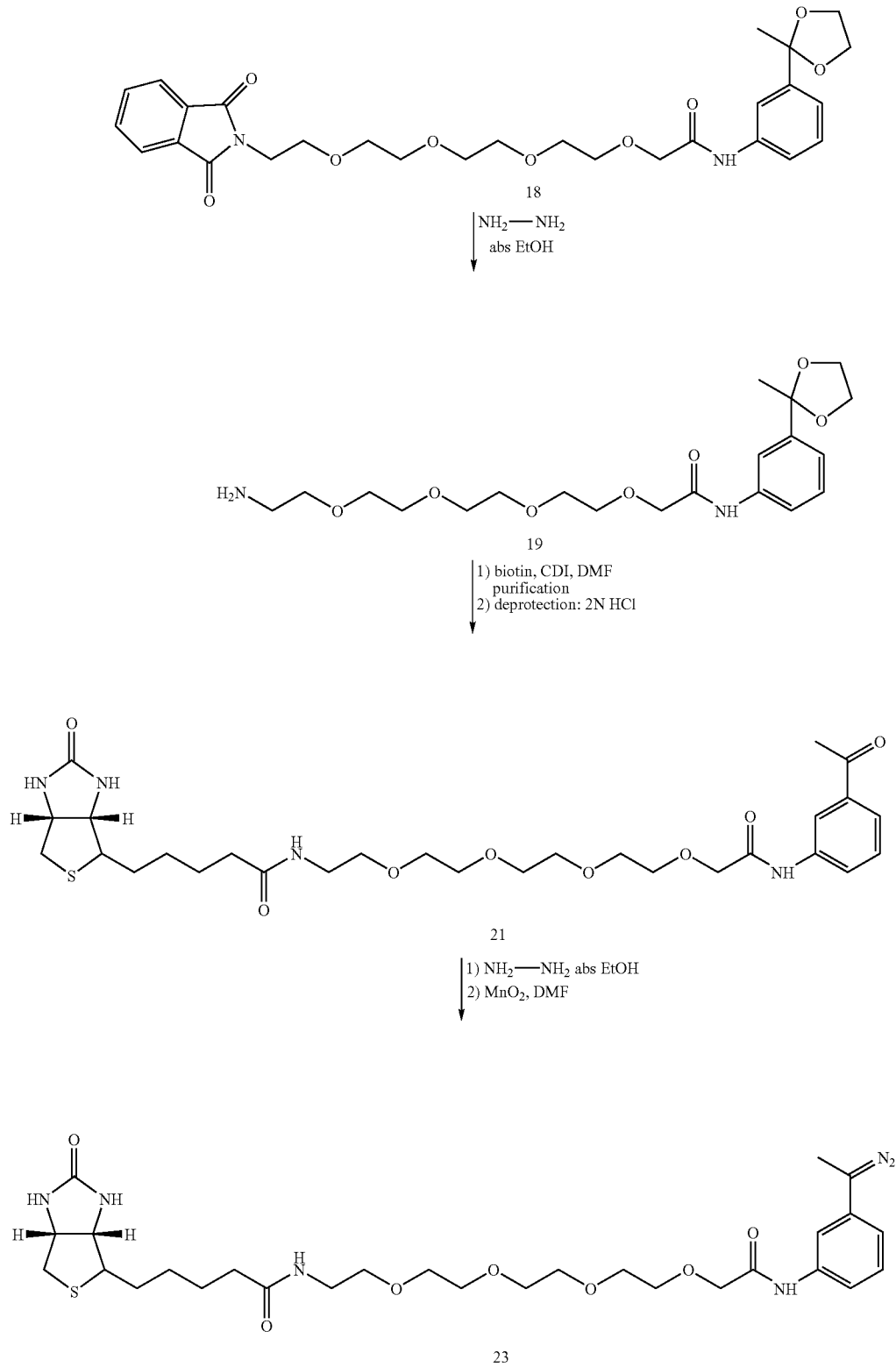

Protection of 3-nitroacetophenone 13:

33 g (0.20 mol) of 3-nitroacetophenone are dissolved in 400 ml of toluene, and then 40 ml (0.717 mol) of ethylene glycol and 600 mg (3.15 mmol) of para-toluenesulfonic acid (PTSA) are added. A Dean Stark system is mounted. The solution is heated for 3 h at 130° C. After having allowed the solution to return to room temperature, 400 ml of ethyl acetate are added, and then the solution is washed with 8 ml of a saturated NaHCO₃ solution. The organic phase is dried over MgSO₄. After evaporation, a pale yellow solid 13 is obtained (39.72 g; 0.190 mol) with a yield of 95%.

$^1$H NMR (200 MHz, CDCl₃) δ=7.11 (t, 1H, J=8 Hz, Ar—H); 6.87–6.78 (m, 2H, Ar—H); 6.59 (dd, 1H, J=6.5 Hz, Ar—H); 4.00 (m, 2H, $H_2C_{acetal}$); 3.79 (m, 2H, $H_2C_{acetal}$); 1.61 (s, 3H, CH₃).

Preparation of the Amine 14:

Compound 13 (39.7 g; 0.190 mol) is dissolved in 500 ml of EtOH, and then 1 g of 10% palladium on carbon is added. The mixture is heated in order to dissolve the whole, and then the solution is allowed to return to room temperature. After having created a vacuum and placed the solution under H₂, it is kept vigorously stirred for 5 h. The solution is then filtered in the hot state and then evaporated. The product 14 is washed with pentane, and isolated in the form of a solid (34 g; 0.189 mol) with a yield of 99%.

$^1$H NMR (200 MHz, CDCl₃) δ=7.14 (t, 1H, J=8 Hz, Ar—H); 6.85 (m, 2H, J=7.5 Hz, Ar—H); 6.79 (s, 1H, Ar—H); 6.59 (dd, 1H, J=6.5 Hz, Ar—H); 4.00 (m, 2H, $H_2C_{acetal}$); 3.77 (m, 2H, $H_2C_{acetal}$); 1.61 (s, 3H, CH₃).

Brominated Compound 15:

The amine 14 (12.3 g; 68.7 mmol) and triethylamine (7 g; 69 mmol) are dissolved in 150 ml of DCM under argon. A solution of 13.8 g (60 mmol) of bromoacetyl bromide dissolved in 150 ml of DCM is added dropwise at −5° C. At the end of the addition, 100 ml of aqueous 1N NaHCO₃ are added. The organic phase is washed twice in succession with aqueous NaHCO₃ and dried over MgSO₄. After evaporation to dryness, 22.6 g of a brown oil are obtained corresponding to compound 15 and used as it is for the next reaction.

$^1$H NMR (200 MHz, CDCl₃) δ=8.29 (broad s, 1H, NH); 7.62 (dt, 1H₄, J=5 Hz, Ar—H); 7.47 (s, 1H, Ar—H₂); 7.38–7.19 (m, 2H, Ar—H_{5,6}); 4.00 (m, 2H, Br—CH₂); 3.75 (m, 4H, $H_2C$—$H_2C_{acetal}$); 1.61 (s, 3H, CH₃).

Alcohol Compound 16:

Sodium hydride (3.3 g; 82.5 mmol) is washed three times with pentane and then suspended in 150 ml of THF, tetraethylene glycol (50 ml; 0.29 mol) is then added at room temperature. The reaction is kept stirred for 15 min, and then the solution is cooled to −5° C.

The addition of compound 15, diluted beforehand in 25 ml of THF, is made dropwise. The mixture is kept stirred for 30 min in order to allow it to return to room temperature. The solution is concentrated to 100 ml and then it is diluted with 500 ml CHCl₃. This organic phase is washed three times in succession with 250 ml of aqueous 1N NaHCO₃, and then it is dried over MgSO₄ before evaporating it. The product is purified by flash chromatography on a silica column (column 65 mm in diameter) with 1.5 l of MeOH-DCM 5%, and then with 500 ml of MeOH-DCM 7%, and finally 500 ml of MeOH-DCM 10%. The fractions corresponding to compound 16 are combined and then evaporated to dryness to give 17.4 g (42.1 mmol) of product, with a yield of 61%.

$^1$H NMR (200 MHz, CDCl₃) δ=8.86 (broad s, 1H, NH); 7.71 (d, 1H, J=7.5 Hz, Ar—H₄); 7.51 (s, 1H, Ar—H₂); 7.29–7.24 (m, 2H, Ar—H_{5,6}); 4.09 (m, 2H, CO—CH₂—O); 3.99 (m, 2H, $H_2C_{acetal}$); 3.72–3.53 (m, 20H, O—CH₂—CH₂—O, $H_2C_{acetal}$ and HO—CH₂); 1.61 (s, 3H, CH₃).

Tosylate Compound 17:

The alcohol 16 (4.13 g; 10.0 mmol) is dissolved in 5 ml of pyridine. 2.0 g (10.5 mmol) of tosyl chloride are then added at room temperature. The mixture is stirred under argon for 10 h. It is diluted with 100 ml of DCM, the organic phase is washed three times with 20 ml of aqueous 1N NaHCO₃, and then it is dried over MgSO₄ before coevaporating it with toluene. Purification by flash chromatography on a column (column 50 mm in diameter) is carried out with 500 ml of MeOH-DCM 2%, and then 500 ml of MeOH-DCM 3%, and finally 500 ml of MeOH-DCM 4%. The fractions corresponding to product 17 are combined and then evaporated to dryness to give 3.68 g (6.48 mmol) of oil with a yield estimated at 65%.

$^1$H NMR (300 MHz, CDCl₃) δ=8.86 (broad s, 1H, NH); 7.76 (d, 4H, J=5.5 Hz, Ar—H_{tosyl}); 7.60 (d, 1H, J=7.5 Hz, Ar—H₄); 7.50 (s, 1H, Ar—H₂); 7.32–7.22 (m, 2H, Ar—H_{5,6}); 4.10 (m, 2H, CO—CH₂—O); 4.00 (m, 2H, $H_2C_{acetal}$); 3.73–3.54 (m, 20H, O—CH₂—CH₂—O, $H_2C_{acetal}$ and HO—CH₂); 2.42 (s, 3H, Ar—CH₃); 1.61 (s, 3H, CH₃).

Phthalimide Compound 18:

The tosylate 17 (3.68 g; 6.48 mmol) is dissolved with 1.52 g (10.0 mmol) of DBU (1,8-diazobicyclo[5.4.0]undecene) and then the phthalimide (1.47 g; 10 mmol) is added. The solution thus obtained is heated at 85–90° C. for 17 h and then evaporated. The product is purified by flash chromatography on a silica column (column 50 mm in diameter) with 1 l of acetone-DCM 15%, and then with 1 l of acetone-DCM 20%. The fractions corresponding to compound 18 are combined and then evaporated to dryness to give 3.15 g (5.8 mmol) of product, with a yield of 90%.

$^1$H NMR (200 MHz, CDCl₃) δ=8.73 (broad s, 1H, NH); 7.79 (m, 2H, Ar—H_{phtha}); 7.99 (m, 2H, Ar—H_{phtha} and Ar—H₄); 7.49 (s, 1H, Ar—H₂); 7.27–7.18 (m, 2H, Ar—H_{5,6}); 4.10 (m, 2H, CO—CH₂—O); 4.00 (m, 2H, $H_2C_{acetal}$); 3.69–3.56 (m, 20H, O—CH₂—CH₂—O, $H_2C_{acetal}$ and N_{phtha}-CH₂); 1.61 (s, 3H, CH₃).

Amine Compound 19:

The product 18 is dissolved in 20 ml of absolute EtOH by heating under reflux at 75–80° C. Hydrazine (1.07 ml; 22.1 mmol) is then added and the reaction is kept stirred for 1 h 15 min. The precipitate obtained is filtered on sintered glass and the ethanolic phase evaporated. The white precipitate is then washed with DCM, and the DCM phase is evaporated. The yellow oil obtained (2.3 g; 5.57 mmol) is directly used for the next reaction, even if it contains imidazole which may be subsequently removed during the step for deprotecting the acetal.

$^1$H NMR (300 MHz, CDCl₃) δ=8.83 (broad s, 1H, NH); 7.69 (d, 1H, J=7.5 Hz, Ar—H₄); 7.51 (s, 1H, Ar—H₂); 7.30–7.19 (m, 2H, Ar—H_{5,6}); 4.10 (m, 2H, CO—CH₂—O); 4.00 (m, 2H, $H_2C_{acetal}$); 3.69–3.56 (m, 20H, O—CH₂—CH₂—O, $H_2C_{acetal}$ and H₂N—CH₂); 1.61 (s, 3H, CH₃).

Biotinylated Compound 20.

D-Biotin (1.05 g; 4.32 mmol) is solubilized in 10 ml of anhydrous DMF. 790 mg (4.87 mmol) of carbonyldiimidazole (CDI) are added under argon. After 10 min of stirring, the amine 19 diluted in 5 ml of DMF is added. The solution is kept stirred for 40 min and then evaporated before being purified by flash chromatography on a column.

For that, a column 50 mm in diameter is used with, as eluent, 500 ml of MeOH-DCM 5%, and then 500 ml of MeOH-DCM 10%, and finally 500 ml of MeOH-DCM 15%. The fractions corresponding to product 20 are combined and then evaporated to dryness to give a yellow oil (1.66 g; 2.6 mmol).

The yellow oil obtained (2.4 g) contains, according to the NMR spectrum, about 30% by weight of imidazole. It is therefore deduced therefrom that the yield of the reaction resulting in product 20 is about 60% relative to the starting biotin.

$^1$H NMR (300 MHz, CDCl$_3$) δ=8.80 (broad s, 1H, NH); 7.66 (m, 3H, Ar—H$_4$ and H$_{imidazole}$); 7.54 (s, 1H, Ar—H$_2$); 7.28–7.24 (m, 2H, Ar—H$_{5,6}$); 7.07 (s, 2H, H$_{imidazole}$), 6.59 (t, 1H, NH$_{15'}$); 6.06 (broad s, 1H, NH$_{B1}$); 5.19 (broad s, 1H, NH$_{B3}$); 4.45 (m, 1H, H$_{B6a}$); 4.27 (m, 1H, H$_{B3a}$); 4.10 (s, 2H, H$_{3'}$); 4.00 (m, 2H, H$_2$C$_{acetal}$); 3.75–3.49 (m, 18H, O—CH$_2$—CH$_2$—O and H$_2$C$_{acetal}$); 3.36 (m, 2H, H$_{14'}$); 3.09 (m, 1H, H$_{B4}$); 2.85 and 2.66 (system ABX, 2H, $^2J_{AB}$=5 Hz, $^3J_{AX}$=12 Hz, $^3J_{BX}$=0 Hz, H$_{B6}$); 2.16 (t, 2H, J=8 Hz, H$_{B10}$); 1.61 (s, 3H, CH$_3$); 1.59–1.3 (m, 6H, H$_{B9, B8, B7}$).

Ketone Compound 21:

The acetal 20 is dissolved in 80 ml of chloroform, and then 30 ml of 2N HCl are added. The mixture is kept vigorously stirred for 45 min. The organic phase is recovered and then dried over anhydrous NaHCO$_3$. After filtration, the solution is evaporated and the oil obtained is washed with pentane to give product 21 (1.48 g; 2.48 mmol) with a yield of 99%.

$^1$H NMR (300 MHz, CDCl$_3$) δ=8.99 (broad s, 1H, NH); 8.07 (s, 1H, Ar—H$_2$); 7.98 (d, 2H, J=8 Hz, Ar—H$_4$); 7.66 (d, 2H, J=8 Hz, Ar—H$_6$); 7.42 (t, 2H, J=8 Hz, Ar—H$_5$); 6.38 (t, 1H, NH$_{15'}$); 5.78 (broad s, 1H, NH$_{B1}$); 4.96 (broad s, 1H, NH$_{B3}$); 4.47 (m, 1H, H$_{B6a}$); 4.29 (m, 1H, H$_{B3a}$); 4.13 (s, 2H, H$_{3'}$); 3.76–3.37 (m, 16H, O—CH$_2$—CH$_2$—O); 3.32 (m, 2H, H$_{14'}$); 3.11 (m, 1H, H$_{B4}$); 2.89 and 2.75 (system ABX, 2H, $^2J_{AB}$=5 Hz, $^3J_{AX}$=12 Hz, $^3J_{BX}$=0 Hz, H$_{B6}$); 2.59 (s, 3H, CH$_3$); 2.16 (t, 2H, J=8 Hz, H$_{B10}$); 1.64–1.40 (m, 6H, H$_{B9, B8, B7}$).

Hydrazone Compound 22:

The ketone 21 is dissolved in 20 ml of absolute EtOH. The mixture is heated under reflux at 75–80° C. Hydrazine (816 µl; 16.81 mmol) is then added and the mixture is kept stirred for 3 h. After filtration, the mixture is evaporated to dryness, the residue is redissolved in ethanol until a sticky white foam is obtained. In a second instance, this foam is dissolved in 50 ml of chloroform and then 20 ml of a saturated NaHCO$_3$ solution are added. The mixture is thoroughly washed and then the organic phase is recovered. It is dried over anhydrous Na$_2$CO$_3$ and after filtration evaporated to dryness to give a new sticky foam. The latter corresponds to product 22 (842 mg; 1.38 mmol) and is obtained with a yield of 66%.

$^1$H NMR (300 MHz, CDCl$_3$) δ=8.81 (broad s, 1H, NH); 8.82 (s, 1H, Ar—H$_2$); 7.64 (d, 2H, J=8 Hz, Ar—H$_4$); 7.32 (m, 4H, Ar—H$_{5,6}$); 6.43 (t, 1H, NH$_{15'}$); 5.89 (broad s, 1H, NH$_{B1}$); 5.46 (broad s, 2H, NH$_2$); 4.99 (broad s, 1H, NH$_{B3}$); 4.44 (m, 1H, H$_{B6a}$); 4.27 (m, 1H, H$_{B3a}$); 4.11 (s, 2H, H$_{3'}$); 3.70–3.37 (m, 16H, O—CH$_2$—CH$_2$—O); 3.32 (m, 2H, H$_{14'}$); 3.08 (m, 1H, H$_{B4}$); 2.87 and 2.67 (system ABX, 2H, $^2J_{AB}$=5 Hz, $^3J_{AX}$=12 Hz, $^3J_{BX}$=0 Hz, H$_{B6}$); 2.11 (m, 5H, CH$_3$ and H$_{B10}$); 1.64–1.40 (m, 6H, H$_{B9, B8, B7}$).

Diazo Compound 23:

The hydrazone 22 (100 mg; 0.164 mmol) is dissolved in 1 ml of DMF under argon. 80 mg of activated MnO$_2$ are added and the mixture is kept vigorously stirred for 30 min. The mixture is filtered through a celite (3 cm)-powdered molecular sieve (1 cm) mixed layer. The solution is then evaporated to dryness. The oil obtained at the end of the evaporation is triturated until a pink powder is obtained which corresponds to compound 23 (78 mg; 0.128 mmol; 78%).

$^1$H NMR (300 MHz, DMSO-d$_6$) δ=9.60 (broad s, 1H, NH); 7.89 (s, 1H, Ar—H$_2$); 7.76 (t, 1H, NH$_{15'}$); 7.35–7.25 (m, 4H, Ar—H$_{5,6}$); 6.64 (d, 2H, J=8 Hz, Ar—H$_4$); 6.36 (broad s, 1H, NH$_{B1}$); 6.32 (broad s, 1H, NH$_{B3}$); 4.28 (m, 1H, H$_{B6a}$); 4.08 (m, 1H, H$_{B3a}$); 4.06 (s, 2H, H$_3$I); 3.55–3.31 (m, 16H, O—CH$_2$—CH$_2$—O); 3.17 (m, 2H, H$_{14'}$); 3.08 (m, 1H, H$_{B4}$); 2.80 and 2.59 (system ABX, 2H, $^2J_{AB}$=5 Hz, $^3J_{AX}$=12 Hz, $^3J_{BX}$=0 Hz, H$_{B6}$); 2.13 (m, 5H, CH$_3$); 2.13 (t, 2H, J=8 Hz, H$_{B10}$) 1.99–1.30 (m, 6H, H$_{B9, B8, B7}$).

The reactivity of compound 23 was tested on uridine 3'-monophosphate and monitored by capillary electrophoresis. The analytical conditions are those of Example 6.1. The results show a half-life period of 30 minutes.

The stability of the reagent is greater than 1 month at −20° C.

EXAMPLE 22.3

Synthesis of para-Bio-EG3-PMDAM

Synthesis scheme:

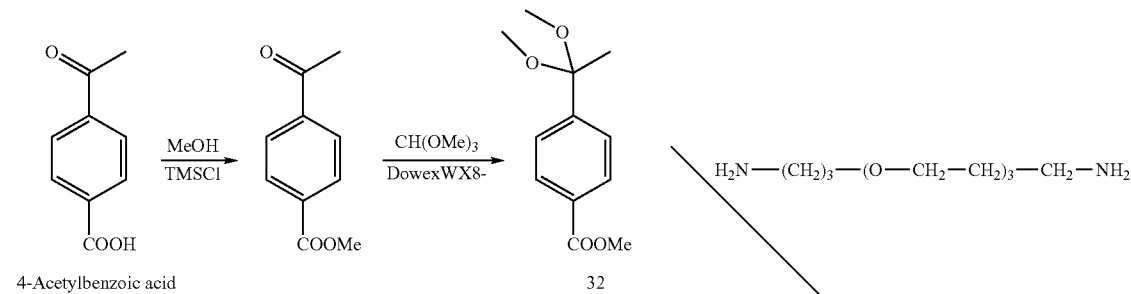

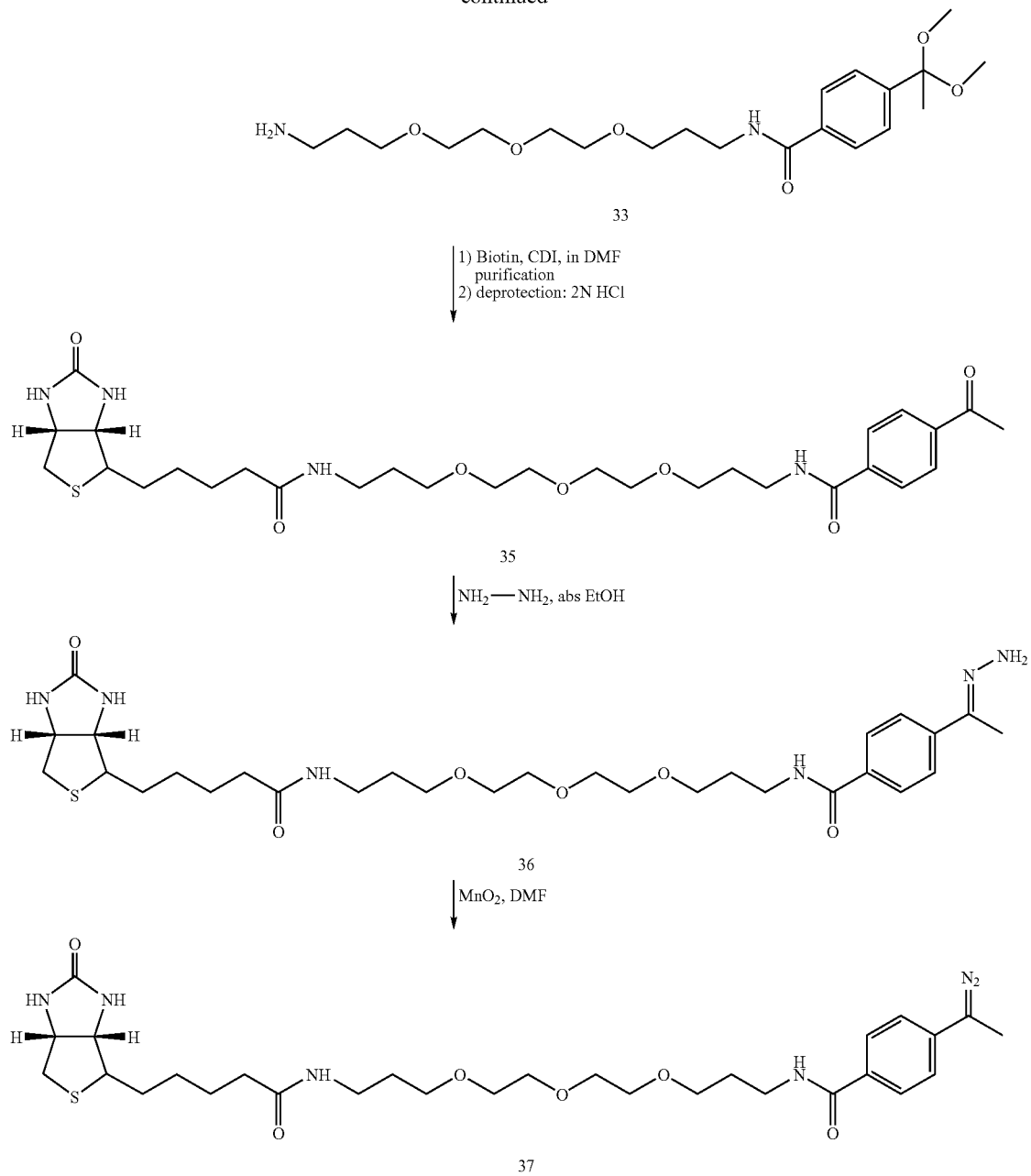

Protection of the 4-acetylbenzoic Acid:

The 4-acetylbenzoic acid (1 g; 6.1 mmol) is dissolved in a trimethylsilyl chloride solution (TMSCl, 10 g; 92 mmol) in 5 ml of MeOH. The mixture is heated at 90° C. overnight. After evaporation, a white solid corresponding to compound 31 (1.21 g; 5.75 mmol) is isolated, characterized by NMR and used as it is for the next reaction.

$^1$H NMR (200 MHz, CDCl$_3$) δ=8.08 (d, 2H, J=8 Hz, Ar—H$_{2,6}$); 7.59 (d, 2H, J=8 Hz, Ar—H$_{3,5}$); 3.18 (s, 6H, —O—CH$_3$); 1.53 (s, 3H, CH$_3$).

Compound 32:

Compound 31 (1.21 g; 5.75 mmol) is dissolved in 5 ml of trimethyl orthoformate in the presence of Dowex 50WX8-100 (0.3 g). The mixture is heated at 60° C. overnight, and then filtered and evaporated to give compound 32 (1.19 g; 5.3 mmol) with a yield of 87%.

$^1$H NMR (200 MHz, CDCl$_3$) δ=8.00 (d, 2H, J=8 Hz, Ar—H$_{2,6}$); 7.54 (d, 2H, J=8 Hz, Ar—H$_{3,5}$); 3.89 (s, 1H, CO—O—CH$_3$); 3.16 (s, 6H, —O—CH$_3$); 1.51 (s, 3H, CH$_3$).

Compound 33:

Compound 32 (1.17 g; 5.22 mmol) is solubilized in 5 ml (22.7 mmol) of 4,7,10-trioxa-1,13-tridecanediamine. The solution obtained is heated at 140° C. for 4 h. The mixture is then dissolved in 30 ml of DCM and washed 3 times with 10 ml of water. The organic phase is dried over MgSO$_4$, and then evaporated until an oil corresponding to product 33 (1.44 g; 3.49 mmol) is obtained with a yield of 67%.

$^1$H NMR (200 MHz, CDCl$_3$) δ=7.76 (d, 2H, J=8 Hz, Ar—H$_{2,6}$); 7.51 (d, 2H, J=8 Hz, Ar—H$_{3,5}$); 3.62–3.47 (m,

14H, $H_{7',8',10',11'}$ and $H_{5',13'}$ and $H_{3'}$); 3.15 (s, 6H, —O—CH$_3$); 2.73 (m, 2H, $H_{15'}$) 1.88 (m, 2H, $H_{4'}$); 1.65 (m, 2H, $H_{14'}$); 1.38 (broad s, 2H, NH$_2$).

Biotinylated Compound 34:

Biotin (780 mg; 3.19 mmol) is suspended in 13 ml of DMF. 590 mg (3.60 mmol) of CDI are then added. This solution is kept stirred for 30 min at room temperature. Compound 33 is dissolved in 1 ml of DMF, and then the preceding solution is added little by little. The mixture thus obtained is kept stirred for 1 h at room temperature. After evaporating the DMF, purification by flash chromatography on a column (column 35 mm in diameter) is carried out with 500 ml of MeOH-DCM 6%, and then with 250 ml of MeOH-DCM 8%, and finally 250 ml of MeOH-DCM 8%. The fractions corresponding to product 34 are combined and then evaporated to dryness to give 1.05 g of oil with a yield estimated at 30%.

$^1$H NMR (300 MHz, CDCl$_3$) δ=8.49 (broad s, 1H, NH$_{imidazole}$); 7-79 (d, 2H, J=8 Hz, Ar—H$_{2,6}$); 7.66 (s, 1H, H$_{imidazole}$); 7.50 (d, 2H, J=8 Hz, Ar—H$_{3,5}$); 7.38 (t, 1H, NH$_{2'}$); 7.11 (s, 2H, H$_{imidazole}$); 6.67 (t, 1H, NH$_{16'}$); 5.99 (broad s, 1H, NH$_{B1}$); 5.15 (broad s, 1H, NH$_{B3}$); 4.46 (m, 1H, H$_{B6a}$); 4.27 (m, 1H, H$_{B3a}$); 3.61–3.45 (m, 14H, H$_{7',8',10',11'}$ and H$_{5',13'}$ and H$_{3'}$); 3.28 (m, 2H, H$_{15'}$); 3.15 (s, 6H, —OCH$_3$); 2.85 (m, 1H, H$_{B4}$); 2.85 and 2.69 (system ABX, 2H, $^2J_{AB}$=5 Hz, $^3J_{AX}$=12 Hz, $^3J_{BX}$=0 Hz, H$_{B6}$); 2.14 (t, 2H, J=8 Hz, H$_{B10}$); 1.86 (m, 2H, H$_{4'}$); 1.69 (m, 2H, H$_{14'}$); 1.49 (s, 3H, CH$_3$); 1.42–1.39 (m, 6H, H$_{B7, B8, B9}$).

Compound 35:

The acetal 34 is dissolved in 45 ml of chloroform, and then 10 ml of 2N HCl are added. The two-phase mixture is vigorously stirred for 5 min. The organic phase is recovered and dried over anhydrous NaHCO$_3$. It is filtered, evaporated, and compound 35 is obtained in the form of a light yellow solid (504 mg; 0.87 mmol) with an overall yield of 27% from biotin.

$^1$H NMR (300 MHz, CDCl$_3$) δ=7.97 (d, 2H, J=8 Hz, Ar—H$_{2,6}$); 7.91 (d, 2H, J=8 Hz, Ar—H$_{3,5}$); 7.51 (t, 1H, NH$_{2'}$); 6.50 (t, 1H, NH$_{16'}$), 6.05 (broad s, 1H, NH$_{B1}$); 5.23 (broad s, 1H, NH$_{B3}$); 4.45 (m, 1H, H$_{B6a}$); 4.27 (m, 1H, H$_{B3a}$); 3.62–3.56 (m, 10H, H$_{7', 8',10',11'}$ and H$_{5'}$); 3.48–3.46 (m, 4H, H$_{3',13'}$); 3.27 (m, 2H, H$_{15'}$); 3.10 (m, 1H, H$_{B4}$); 2.85 and 2.71 (system ABX, 2H, $^2J_{AB}$=5 Hz, $^3J_{AX}$=12 Hz, $^3J_{BX}$=0 Hz, H$_{B6}$); 2.60 (s, 3H, CH$_3$); 2.14 (t, 2H, J=8 Hz, H$_{B10}$); 1.89 (m, 2H, H$_{4'}$); 1.72–1.61 (m, 6H, H$_{14'}$, H$_{B7\ B9}$); 1.40 (m, 2H, H$_{B8}$).

Hydrazone Compound 36:

The ketone 35 (500 mg; 0.864 mmol) is dissolved in 11 ml of absolute EtOH. The hydrazine (335 µl; 6.911 mmol) is added, and then the reaction mixture is heated under reflux for 1 h. The oil obtained after evaporation is dissolved in abs EtOH so as to be evaporated again. A sticky foam corresponding to product 36 (488 mg; 0.823 mmol) is then obtained with a yield of 95%.

$^1$H NMR (300 MHz, CDCl$_3$) δ=7.76 (d, 2H, J=8 Hz, Ar—H$_{2,6}$); 7.67 (d, 2H, J=8 Hz, Ar—H$_{3,5}$); 7.29 (t, 1H, NH$_{2'}$); 6.46 (t, 1H, NH$_{16'}$), 5.98 (broad s, 1H, NH$_{B1}$); 5.55 (broad s, 2H, NH$_2$); 5.14 (broad s, 1H, NH$_{B3}$); 4.45 (m, 1H, H$_{B6a}$); 4.24 (m, 1H, H$_{B3a}$); 3.62–3.51 (m, 10H, H$_{7', 8',10',11'}$ and H$_{5'}$); 3.47–3.45 (m, 4H, H$_{3',13'}$); 3.27 (m, 2H, H$_{15'}$); 3.07 (m, 1H, H$_{B4}$); 2.84 and 2.69 (system ABX, 2H, $^2J_{AB}$=5 Hz, $^3J_{AX}$=12 Hz, $^3J_{BX}$=0 Hz, H$_{B6}$); 2.11 (t, 2H, J=8 Hz, H$_{B10}$ and s, 3H, CH$_3$); 1.86 (m, 2H, H$_{4'}$); 1.72–1.59 (m, 6H, H$_{14'}$, H$_{B7, B9}$); 1.21 (m, 2H, H$_{B8}$).

Diazo Compound 37:

The hydrazone 36 (200 mg; 0.337 mmol) is solubilized in 5 ml of DMF. MnO$_2$ (450 mg; 5.17 mmol) is then added. After 15 min of stirring at room temperature, the mixture is filtered on millipore containing celite (thickness: 2 cm) and 3 Å (0.5 cm) powdered molecular sieve. The reaction mixture is evaporated to dryness. The residual oil obtained is washed with ether three times in succession, until a powder is obtained. Compound 37 (290 mg, 0.491 mmol) is obtained in the form of a pink solid with a yield of 93%.

$^1$H NMR (300 MHz, DMSO-d$_6$) δ=8.33 (t, 1H, NH$_{2'}$); 7.83 (d, 2H, J=8 Hz, Ar—H$_{2,6}$); 7.73 (t, 1H, NH$_{16'}$); 6.98 (d, 2H, J=8 Hz, Ar—H$_{3,5}$); 6.39 (broad s, 1H, NH$_{B1}$); 6.33 (broad s, 1H, NH$_{B3}$); 4.30 (m, 1H, H$_{B6a}$); 4.12 (m, 1H, H$_{B3a}$); 3.51–3.45 (m, 16H, H$_{7',8',10',11'}$ and Hs and H$_{15}$1 and H$_{3',13'}$); 3.07 (m, 1H, H$_{B4}$); 2.79 and 2.58 (system ABX, 2H, $^2J_{AB}$=5 Hz, $^3J_{AX}$=12 Hz, $^3J_{BX}$=0 Hz, H$_{B6}$); 2.14 (s, 3H, CH$_3$); 2.04 (t, 2H, J=8 Hz, H$_{B10}$); 1.77 (m, 2H, H$_{4'}$); 1.62–1.48 (m, 6H, H$_{14'}$, H$_{B7, B9}$); 1.31 (m, 2H, H$_{B8}$).

The reactivity of compound 37 was tested on uridine 3'-monophosphate and monitored by capillary electrophoresis. The analytical conditions are those of Example 6.1. The results show a half-life period of 60 minutes.

The reagent is stable at −20° C. for at least 1 month.

EXAMPLE 22.4

Synthesis of Meta-Bio-EG3-PDAM

Synthesis scheme:

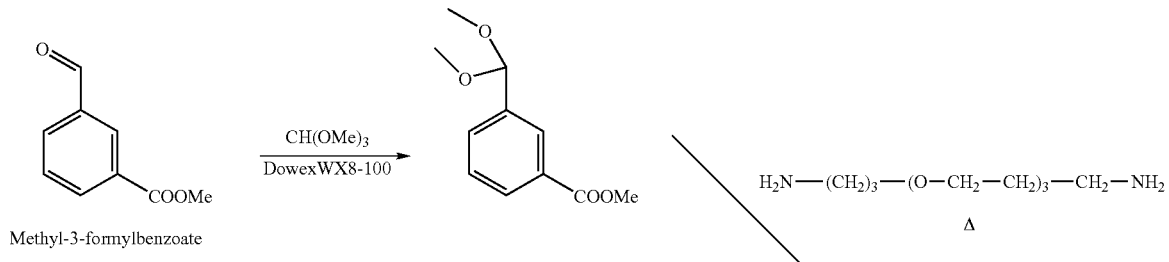

-continued
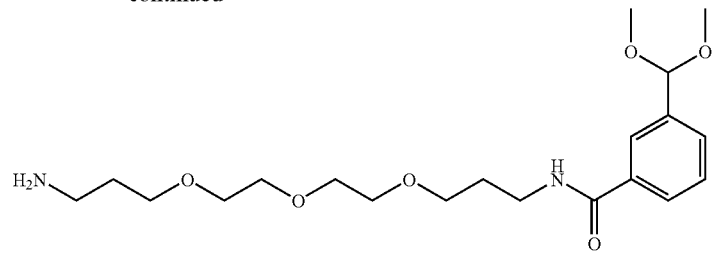
40
1) Biotin, CDI, in DMF
2) Deprotection: 2N HCl
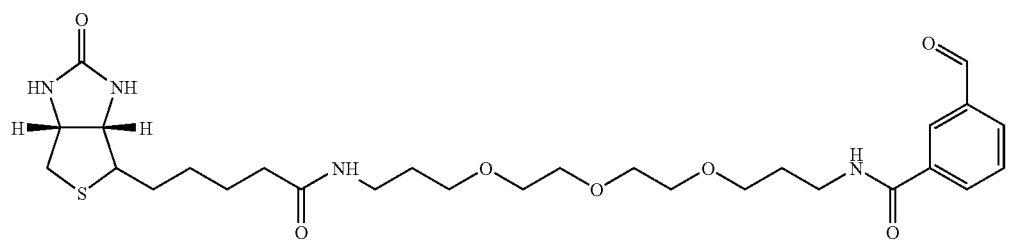
42
NH₂—NH₂, abs EtOH
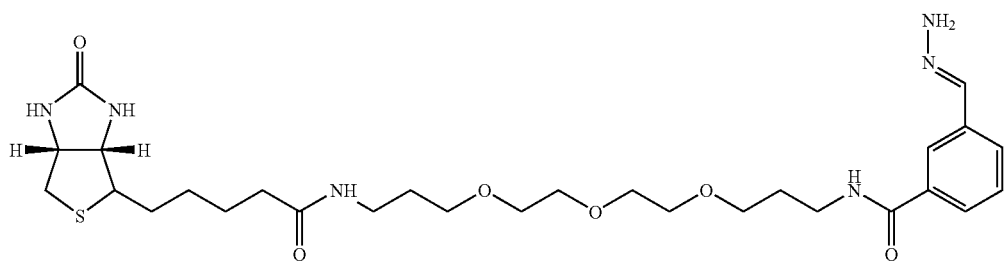
43
MnO₂, DMF
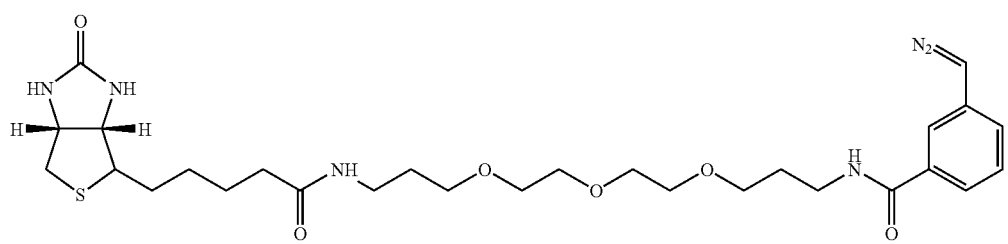
44

Protection of methyl 3-formylbenzoate 38:

The Dowex 50WX8-100 resin (2 g) is dissolved in 25 ml of MeOH and 25 ml of trimethyl orthoformate and then kept stirred for 15 min. After decantation, the resin is washed twice in succession with 20 ml of MeOH. This resin is then placed in 100 ml of MeOH, 50 ml of $CH(OMe)_3$ and 7.12 g (43.4 mmol) of methyl 3-formylbenzoate are added. The solution is kept stirred for 15 min, and then filtered on pleated paper before evaporation. Product 39 (9 g; 43.1 mmol) is isolated in the form of a light yellow liquid with a yield of 99%.

$^1$H NMR (200 MHz, $CDCl_3$) δ=8.10 (s, H, Ar—$H_2$); 7.9 (d, H, J=8 Hz, Ar—$H_4$); 7.63 (d, H, J=8 Hz, Ar—$H_6$); 7.42 (t, H, J=8 Hz, Ar—$H_5$); 5.40 (s, 1H, CH); 3.90 (s, 3H, —CO—O—$CH_3$); 3.31 (s, 6H, —O—$CH_3$).

Compound 40:

Compound 39 (2 g; 9.5 mmol) is solubilized in 10.4 ml (47.6 mmol) of 4,7,10-trioxa-1,13-tridecanediamine. The solution obtained is heated at 165° C. for 2 h. The mixture is then dissolved in 80 ml of DCM and washed 4 times with 20 ml of water. After drying over $MgSO_4$ and evaporation, product 40 is isolated with a yield of 60% (2.27 g; 5.69 mmol).

$^1$H NMR (200 MHz, $CDCl_3$) δ=7.84 (s, H, Ar—$H_2$); 7.75 (d, H, J=8 Hz, Ar—$H_4$); 7.53 (d, H, J=8 Hz, Ar—$H_6$); 7.39 (t, H, J=8 Hz, Ar—$H_5$); 5.38 (s, 1H, CH); 3.64–3.43 (m, 14H, $H_{7',8',10',11'}$ and $H_{5',13'}$ and $H_3$); 3.29 (s, 6H, —O—$CH_3$); 2.72 (m, 2H, $H_{15'}$); 1.87 (m, 2H, $H_{4'}$); 1.64 (m, 2H, $H_{14'}$); 1.30 (broad s, 2H, $NH_2$).

Biotinylated Compound 41:

D-biotin (344 mg; 1.40 mmol) is suspended in 4 ml of DMF and then 250 mg (1.54 mmol) of CDI are added. This solution is kept stirred for 30 min at room temperature. Compound 40 (616 mg; 1.54 mmol) is dissolved in 2 ml of DMF, and then the preceding solution is added little by little. The mixture thus obtained is kept stirred, for 50 min at room temperature. After evaporation, purification by flash chromatography on a column (column 30 mm in diameter) is carried out with 750 ml of MeOH-DCM 10%, and then with 250 ml of MeOH-DCM 15%. The fractions corresponding to product 41 are combined and then evaporated to dryness to give 740 mg of oil with a yield estimated at 50%.

$^1$H NMR (200 MHz, $CDCl_3$) δ=7.87 (s, H, Ar—$H_2$); 7.78 (d, H, J=8 Hz, Ar—$H_4$); 7.65 (s, 1H, $H_{imidazole}$); 7.53 (d, H, J=8 Hz, Ar—$H_6$); 7.39 (t, H, J=8 Hz, Ar—$H_5$); 7.07 (s, 2H, $H_{imidazole}$); 6.65 (t, 1H, $NH_{16'}$); 5.95 (broad s, 1H, $NH_{B1}$); 5.38 (s, 1H, CH); 5.15 (broad s, 1H, $NH_{B3}$); 4.43 (m, 1H, $H_{B6a}$); 4.27 (m, 1H, $H_{B3a}$); 3.59–3.44 (m, 14H, $H_{7',8',10',11'}$ and $H_{5',13'}$ and $H_3$); 3.29 (m, 8H, $H_{15}$ and 2-O—$CH_3$); 3.07 (m, 1H, $H_{B4}$); 2.84 and 2.66 (system ABX, 2H, $^2J_{AB}$=5 Hz, $^3J_{AX}$=12 Hz, $^3J_{BX}$=0 Hz, $H_{B6}$); 2.13 (t, 2H, J=8 Hz, $H_{B10}$); 1.85 (m, 2H, $H_{4'}$); 1.66 (m, 2H, $H_{14'}$); 1.40–1.37 (m, 6H, $H_{B7, B8, B9}$).

Aldehyde Compound 42:

The acetal 41 is dissolved in 20 ml of chloroform, and then 5 ml of 2N HCl are added. The two-phase mixture is vigorously stirred for 15 min. The organic phase is recovered and dried over anhydrous $NaHCO_3$. It is filtered, evaporated and compound 42 is obtained in the form of a yellow oil (593 mg; 1.02 mmol) with an overall yield of 87% from biotin.

$^1$H NMR (300 MHz, $CDCl_3$) δ=10.04 (s, 1H, CHO); 8.34 (s, H, Ar—$H_2$); 8.16 (d, H, J=8 Hz, Ar—$H_4$); 7.96 (d, H, J=8 Hz, Ar—$H_6$); 7.72 (t, 1H, $NH_{2'}$); 7.39 (t, H, J=8 Hz, Ar—$H_5$); 6.51 (t, 1H, $NH_{16'}$); 6.00 (broad s, 1H, $NH_{B1}$); 5.30 (broad s, 1H, $NH_{B3}$); 4.46 (m, 1H, $H_{B6a}$); 4.27 (m, 1H, $H_{B3a}$); 3.66–3.56 (m, 10H, $H_{7',8',10',11'}$ and $H_{5'}$); 3.50–3.29 (m, 4H, $H_{3',13'}$); 3.28 (m, 2H, $H_{15}$); 2.95 (m, 1H, $H_{B4}$); 2.84 and 2.71 (system ABX, 2H, $^2J_{AB}$=5 Hz, $^3J_{AX}$=12 Hz, $^3J_{BX}$=0 Hz, $H_{B6}$); 2.15 (t, 2H, J=8 Hz, $H_{B10}$); 1.89 (m, 2H, $H_{4'}$); 1.72–1.63 (m, 6H, $H_{14'}$, $H_{B7, B9}$); 1.23 (m, 2H, $H_{B8}$).

Hydrazone Compound 43:

The aldehyde 42 (593 mg; 1.02 mmol) is dissolved in 10 ml of absolute ethanol. The hydrazine (400 µl; 8.19 mmol) is added, and then the reaction mixture is heated under reflux for 50 min. The yellow oil obtained after evaporation is triturated with ether until a beige powder corresponding to product 43 (404 mg; 0.68 mmol) is obtained with a yield of 66%. Purification by flash chromatography on a column (column 15 mm in diameter) is then carried out on a 150 mg (0.253 mmol) sample with 200 ml of MeOH-DCM 20%. The fractions are combined and then evaporated to dryness to give 144 mg of product 43 with a yield of 76%.

$^1$H NMR (300 MHz, $CDCl_3$) δ=7.95 (s, H, Ar—$H_2$); 8.16 (d, H, J=8 Hz, Ar—$H_4$); 7.76 (s, 1H, CH); 7.96 (d, H, J=8 Hz, Ar—$H_6$); 7.38 (t, H, J=8 Hz, Ar—$H_5$); 6.45 (t, 1H, $NH_{16'}$); 5.98 (broad s, 1H, $NH_{B1}$); 5.72 (broad s, 2H, $NH_2$); 5.18 (broad s, 1H, $NH_{B3}$); 4.44 (m, 1H, $H_{B6a}$); 4.26 (m, 1H, $H_{B3a}$); 3.62–3.56 (m, 10H, $H_{7',8',10',11'}$ and $H_{5'}$); 3.48–3.45 (m, 4H, $H_{3',13'}$); 3.27 (m, 2H, $H_{15'}$); 3.07 (m, 1H, $H_{B4}$); 2.84 and 2.68 (system ABX, 2H, $^2J_{AB}$=5 Hz, $^3J_{AX}$=12 Hz, $^3J_{BX}$=0 Hz, $H_{B6}$); 2.11 (t, 2H, J=8 Hz, $H_{B10}$); 1.86 (m, 2H, $H_{4'}$); 1.72–1.59 (m, 6H, $H_{14'}$, $H_{B7, B9}$); 1.21 (m, 2H, $H_{B8}$).

Diazo Compound 44:

The hydrazone 43 (100 mg; 0.187 mmol) is solubilized in 4 ml of DMF. $MnO_2$ (200 mg; 2.3 mmol) is then added. After 13 min of stirring at room temperature, the mixture is filtered on millipore containing celite (thickness: 2 cm) and 3 Å (0.5 cm) powdered molecular sieve. The reaction mixture is evaporated to dryness. The residual oil obtained is washed with ether three times in succession. Compound 44 (290 mg, 0.491 mmol) is obtained in the form of an orange solid with a yield of 83%.

$^1$H NMR (300 MHz, DMSO-$d_6$) δ=8.39 (t, 1H, $NH_{2'}$); 7.78 (t, 1H, $NH_{16'}$); 7.39–7.34 (m, Ar—H); 7.09 (d, Ar—H); 6.38 (broad s, 1H, $NH_{B1}$); 6.32 (broad s, 1H, $NH_{B3}$); 5.78 (s, 1H, CH—$N_2$); 4.27 (m, 1H, $H_{B6a}$); 4.11 (m, 1H, $H_{B3a}$); 3.51–3.44 (m, 10H, $H_{7',8',10',11'}$ and $H_{5'}$); 3.37 (m, 2H, $H_{15}$); 3.32 (m, 4H, $H_{3',13'}$); 3.05 (m, 1H, $H_{B4}$); 2.79 and 2.58 (system ABX, 2H, $^2J_{AB}$=5 Hz, $^3J_{AX}$=12 Hz, $^3J_{BX}$=0 Hz, $H_{B6}$); 2.02 (t, 2H, J=8 Hz, $H_{B10}$); 1.69 (m, 2H, $H_{4'}$); 1 59–1.48 (m, 6H, $H_{14'}$, $H_{B7, B9}$); 1.25 (m, 2H, $H_{B8}$).

The stability of the product is greater than 1 month at −20° C.

EXAMPLE 23

Synthesis of Para-Cy5-EG3-PDAM

As has already been mentioned in Example 2, the biotin may be replaced with another marker such as Cy5. This example shows that the diazo functional group, carried by PDAM, may also be linked to this Cy5 marker via a polyethylene glycol linking arm.

Synthesis scheme:
The counter-ion I⁻ is not represented
in the formulae 46, 47, 50', and 51.

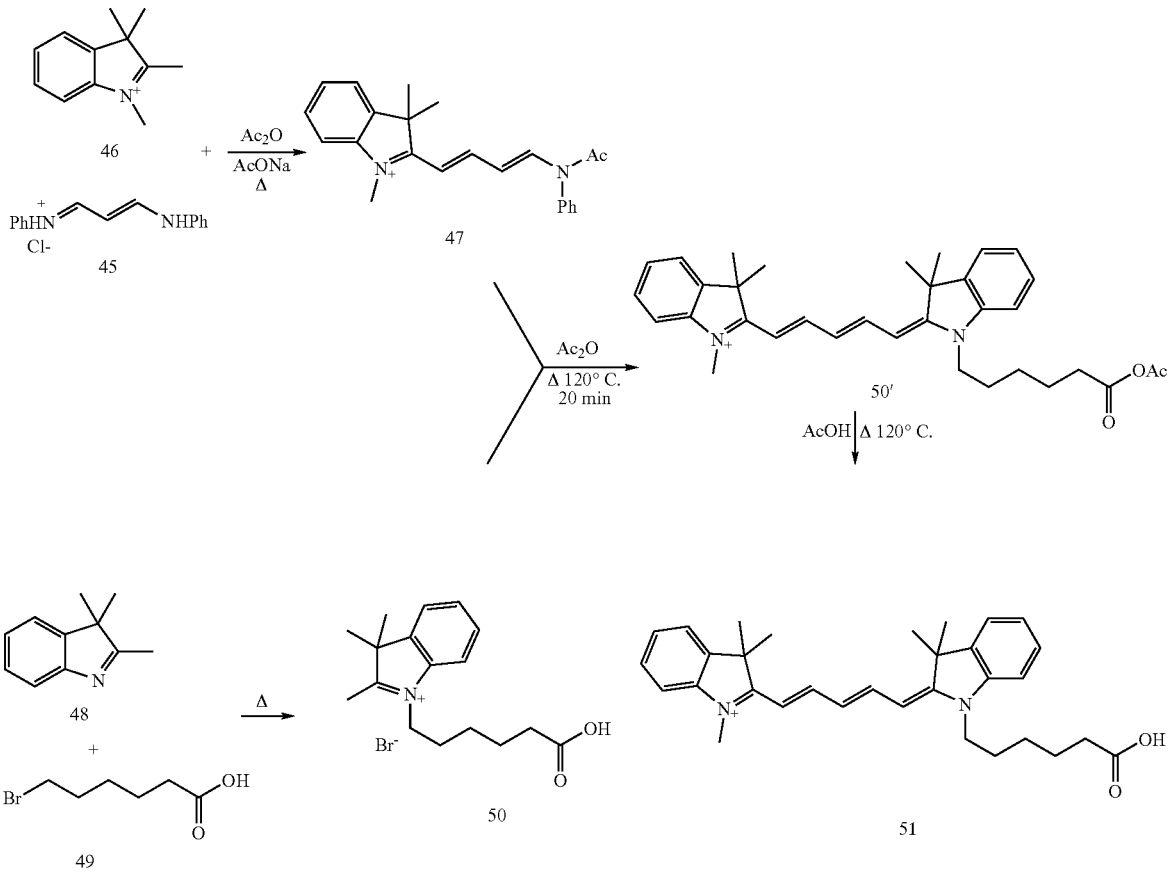

2-[4-(N-Acetyl-N-phenylamino)buta-1,3-dienyl]-1,2,3,3-tetramethyl[3H]indolium Iodide 47:

The mixture of malonaldehydebis(phenylimine) monohydrochloride 45 (13 g; 50.2 mmol), NaOAc (6.0 g; 69.7 mmol) and 1,2,3,3-tetramethyl[3H]indolium iodide 46 (3.01 g; 10 mmol) in acetic anhydride (50 ml) is heated at 100° C. for precisely 20 min. After cooling, ether (350 ml) is added and the brown solid precipitated is filtered and washed with ether (3×100 ml). The solid is redissolved in 150 ml of $CH_2Cl_2$, filtered (removal of the inorganic salts) and then precipitated with 350 ml of ether to give a brown solid (3.54 g, 54%).

$^1$H NMR (CDCl$_3$): δ=8.64 (d; 1H; J=12 Hz; 1-H); 8.14 (t; 1H; J=16; 12 Hz; 3-H); 7.63–7.19 (m; 9H); 6.90 (d; 1H; J=15 Hz; 4-H); 5.82 (t; 1H; J=12; 13 Hz; 2-H); 4.06 (s; 3H; NCH$_3$); (2.16 (s; 3H; —COCH$_3$); 1.74 (s; 6H; CH$_3$)—

1-(5-Carboxypentyl)-2,3,3-trimethyl[3H]indolium Bromide 50:

2,3,3-Trimethylindole 48 (10.0 g; 62.8 mmol) and 6-bromohexanoic acid 49 (12.3 g; 62.8 mmol) are mixed without solvent and heated at 110° C. for 12 h under argon. The violet-red pasty reaction mixture is washed with ethyl acetate (2×60 ml, the paste is triturated with the specula and the supernatant is decanted off), and then with acetone (50 ml, the paste solidifies). The pink solid is filtered and then dried under vacuum (16.0 g; 73%).

Cy5COOH Compound 51:

The mixture of the iodide 47 (2.5 g; 5.3 mmol), of the bromide 50 (1.87 g; 5.3 mmol) and of NaOAc (1.08 g; 12.1 mmol) in acetic anhydride (11 ml) is heated at 120° C. for 25 min. After cooling, ether (200 ml) is added and the precipitate is filtered and washed with ether (3×50 ml). The solid corresponding to product 50' is dissolved in 100 ml of $CH_2Cl_2$ and then evaporated. It is then dissolved in 15 ml of acetic acid and stirred for 30 min at 120° C. The precipitate corresponding to product 51 is then obtained after addition of 200 ml of ether and filtration on sintered glass, with a yield of 84% (2.71 g; 4.44 mmol).

$^1$H NMR (CDCl$_3$): δ=8.03 (t; 2H; J=10; 11 Hz, 2-H, 4-H); 7.38–6.91 (m; 9H; Ar—H, 3-H); 6.41 (d; 1H; J=14 Hz; 1-H); 6.31 (d; 1H; J=13 Hz; 5-H); 4,07 (t; 2H; J=7; 7 Hz; α-CH$_2$); 3.68 (s; 3H; NCH$_3$); 2.47 (t; 2H; J=7; 7 Hz; ε-CH$_2$); 1.71 (m; 18H; CH$_3$, β, γ and δ-CH$_2$).

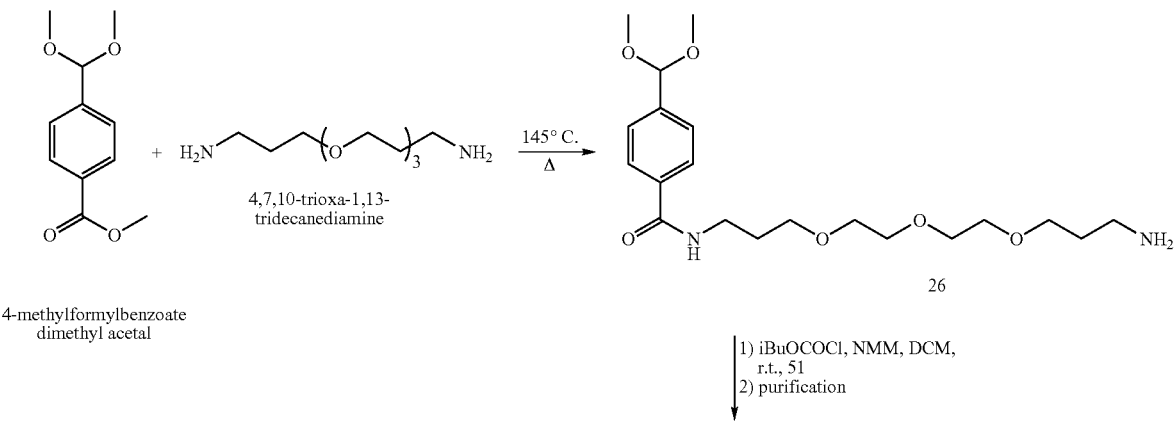
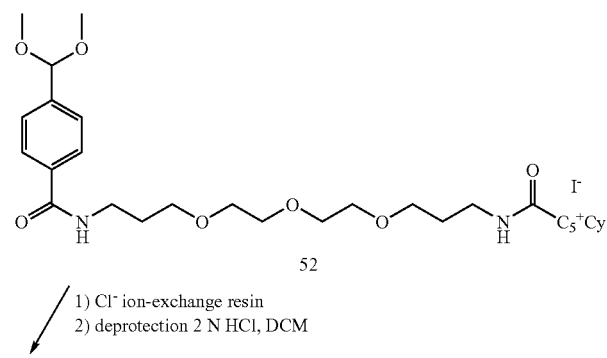
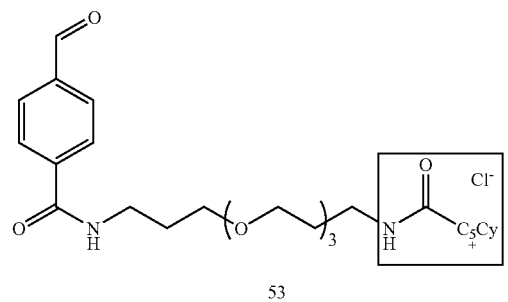
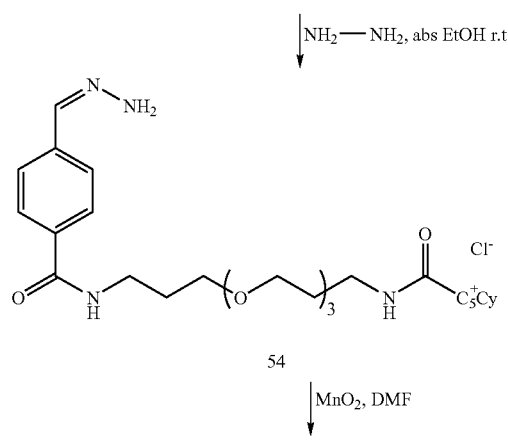

-continued

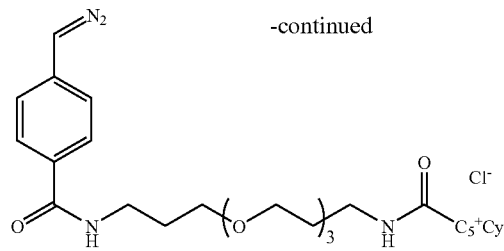

55

Coupling of Compound 26 with Cy5COOH 51 (Product 52):

To a solution of Cy5COOH 51 (1.5 g; 2.46 mmol) in 15 ml of CH$_2$Cl$_2$, N-methylmorpholine (NMM, 405 µl; 3.68 mmol) is added. The solution is cooled with an ice bath and placed under argon, and then isobutyl chloroformate (494 µl; 3.81 mmol) is added. After 10 min of stirring, the amine 26 (1.86 mg; 4.67 mmol) diluted in 8 ml of CH$_2$Cl$_2$ is added. The mixture is kept stirred at room temperature for 1 h 30 min. 20 ml of CH$_2$Cl$_2$ are added and the mixture is washed with 25 ml of NaHCO$_3$ (1N) three times in succession. After drying over Na$_2$CO$_3$, the solution is filtered in order to recover the dichloromethane phase which is evaporated.

Purification by flash chromatography on a column (column 45 mm in diameter, 20 ml fractions) is carried out with, as eluent, MeOH-DCM 10%. The fractions corresponding to product 52 are combined and then evaporated to dryness to give a blue solid which is dissolved in CH$_2$Cl$_2$. Product 52 is then precipitated and washed with ether to give a blue product with a yield of 72% (1.45 g; 1.77 mmol).

Product 52 (iodide) is then dissolved in 54 ml of methanol and then passed over an amberlite IRA900 column (Cl$^-$; 15 g). The methanolic solution recovered is evaporated to dryness to give a sticky oil which is redissolved in CH$_2$Cl$_2$. The evaporation makes it possible to obtain product 52' with a yield of 87%.

Aldehyde 53:

The acetal 52' is dissolved in 10 ml of DCM, and then 10 ml of 2N HCl are added. The solution is kept vigorously stirred for 3 h 30 min. After adding 20 ml of DCM, the dichloromethane phase is recovered and then dried over NaHCO$_3$. The product obtained after evaporation is washed with ether to give the aldehyde 53 with a yield of 90% (1.18 g; 1.46 mmol).

Hydrazone 54:

The aldehyde 53 (200 mg; 0.247 mmol) is dissolved in 1 ml of absolute ethanol and hydrazine monohydrate (15.6 µl; 0.321 mmol) is added. The solution is stirred at room temperature for 30 min. 8 ml of ether are added; the mixture is washed with ether by decantation three times in succession and then dried under vacuum. 172 mg of hydrazine 54 (0.209 mmol; 85% yield) is obtained and stored in a freezer.

Diazo 55:

To a solution of 20 mg (0.243 mmol) of hydrazone 54 in 2 ml of DMF, 100 mg of MnO$_2$ are added and the mixture is vigorously stirred for 5 min under argon at room temperature. The suspension is filtered through a layer of celite (thickness: 2 cm) and powdered molecular sieve 3 Å (0.5 cm) and washed with DMF. The solution is evaporated and then the residue is triturated with ether. The solid thus obtained is dried. 18 mg (0.185 mmol; 76%) of diazo 55 are obtained.

The stability of the reagent is greater than 1 month at −20° C.

EXAMPLE 24

Synthesis of meta-Fluo-EG3-PMDAM

As already mentioned in Example 23, the biotin may be replaced with another marker. This example shows that it is also possible to link the diazo functional group, carried by PMDAM, to this fluorescein marker via a polyethylene glycol linking arm.

Synthesis scheme

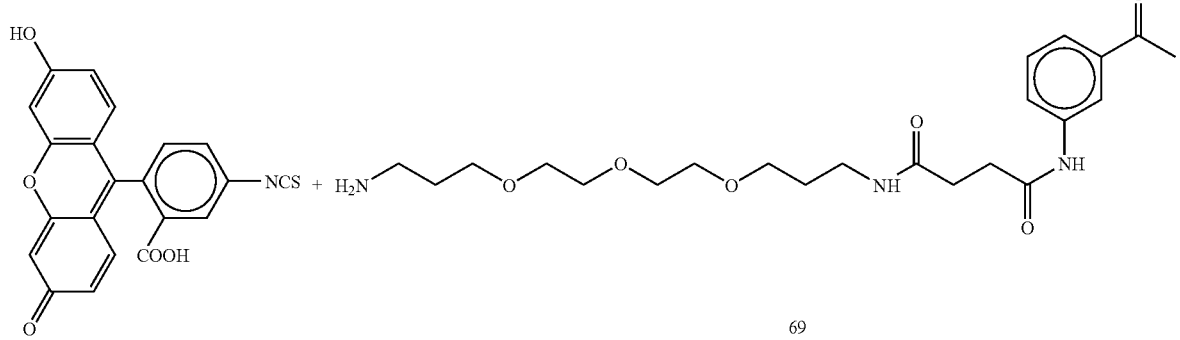

69

↓

-continued

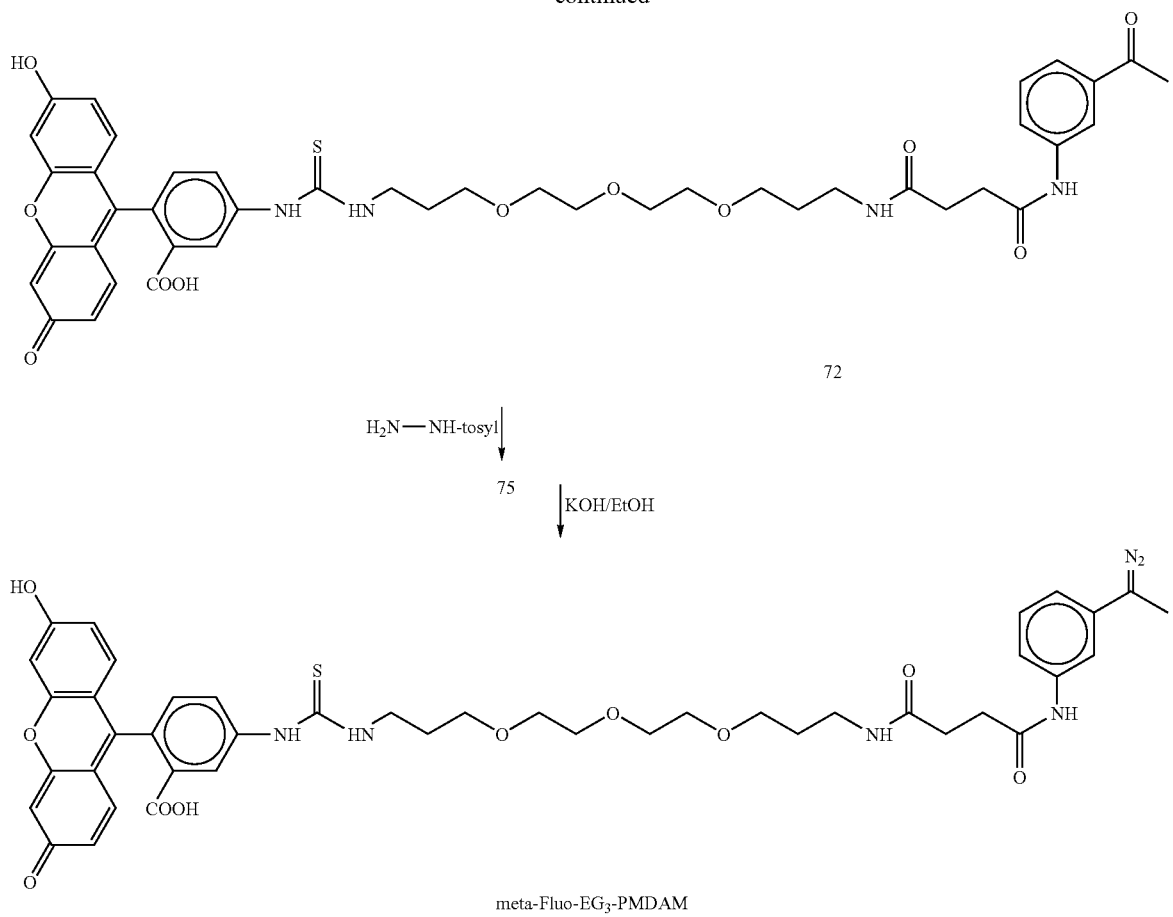

Compound 72:

Fluorescein isothiocyanate (250 mg, 0.64 mmol) is solubilized in 1.6 ml of anhydrous DMF, with 2% of pyridine, under argon. The product 69 (0.356 g, 0.81 mmol), dissolved in 1.6 ml of anhydrous DMF, is added. The mixture is allowed to react for 3.5 h at room temperature, and then the DMF is evaporated and the residue is taken up in 25 ml of $H_2O$. Three extractions are then made with 50 ml of $CH_2Cl_2$, and the aqueous phase is evaporated. 255 mg (48%) of product 72 are obtained.

meta-Fluo-$EG_3$-Hydrazone-Tosyl Compound 75:

Compound 72 (255 mg, 0.31 mmol) is dissolved in 1.5 ml of ethanol under reflux. p-Toluenesulfonyl-hydrazine (69.2 mg, 0.37 mmol) in 1.5 ml of ethanol is added and the mixture is allowed to react for 6 h. The mixture is evaporated to dryness, and the solid is washed with $CH_2Cl_2$, $H_2O$ and ether. 18.5 mg (74%) of product 75 are obtained in the form of an orange powder.

$^1$H NMR (200 MHz, DMSO-$d_6$): δ=1.6–1.8 (m, 4H); 2.13 (s, 1H); 2.28 (s, 1H); 2.36 (s, 1H); 2.80 (m, 1H); 3.07 (m, 2H); 3.46 (m, 12H); 6.5–6.7 (m, 6H); 7.1–8.3 (m, 9H).

meta-Fluo-$EG_3$-PMDAM Compound 74:

The hydrazone 75 (176 mg, 0.18 mmol) is solubilized in 720 μl of a 10% KOH solution in anhydrous methanol. The solution is kept under reflux for 3 h. The solution is allowed to cool and a precipitate appears. The solution is filtered and evaporated to dryness. The residue is washed with ether and dried.

The NMR analysis shows the disappearance of signals at 2.36 and 2.13 ppm (corresponding to the methyls of the tosyl and of the hydrazone) and the appearance of a peak at 1.96 ppm (corresponding to the methyl of the diazo).

EXAMPLE 25

Diazomethyl Intermediate Allowing Subsequent Labeling

It may be advantageous to have not a direct labeling with the diazomethyl labeling reagent also carrying the marker $R^2$ but to proceed in two stages with an indirect labeling. In this case, the labeling reagent comprising the diazomethyl functional group is said to be prefunctionalized, that is to say that it also comprises a chemical functional group capable of subsequently reacting with direct or indirect markers. The prefunctionalization may occur by introducing a reactive covalent functional group into the labeling reagent which may react with an anti-reactive covalent functional group of the direct or indirect marker. These functional groups may consist of an electrophilic organic chemical functional group and a nucleophilic organic chemical functional group, or conversely.

An example of such a labeling strategy is illustrated by the scheme below

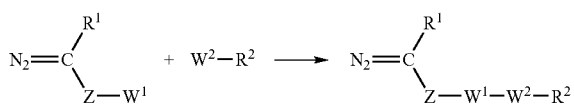

in which the labeling reagent comprises, in addition to a diazomethyl functional group, an electrophilic or nucleophilic functional group $W^1$ capable of reacting with a marker $R^2$ comprising a functional group $W^2$ complementary to $W^1$.

For example, if $W^1$ is a methyl ketone or aldehyde functional group, $W^2$ is an alkoxyamine functional group.

In a method for labeling a biological molecule such as a nucleic acid, the nucleic acid is brought into contact with the labeling reagent comprising the diazomethyl functional group and, in a subsequent step, the marker $W^2$—$R^2$ reacts with the nucleic acid via the functional group $W^1$.

One of the uses consists, for example, in a method for amplifying a sequence of a nucleic acid or in a method for signal amplification. Additional information on this type of labeling may be found in patent application WO-A-98/05766, under the priority of Aug. 2, 1996, and in patent application WO-A-00/40590 under the priority of Jan. 5, 1999.

EXAMPLE 25.1

Synthesis of MeCO-PMDAM

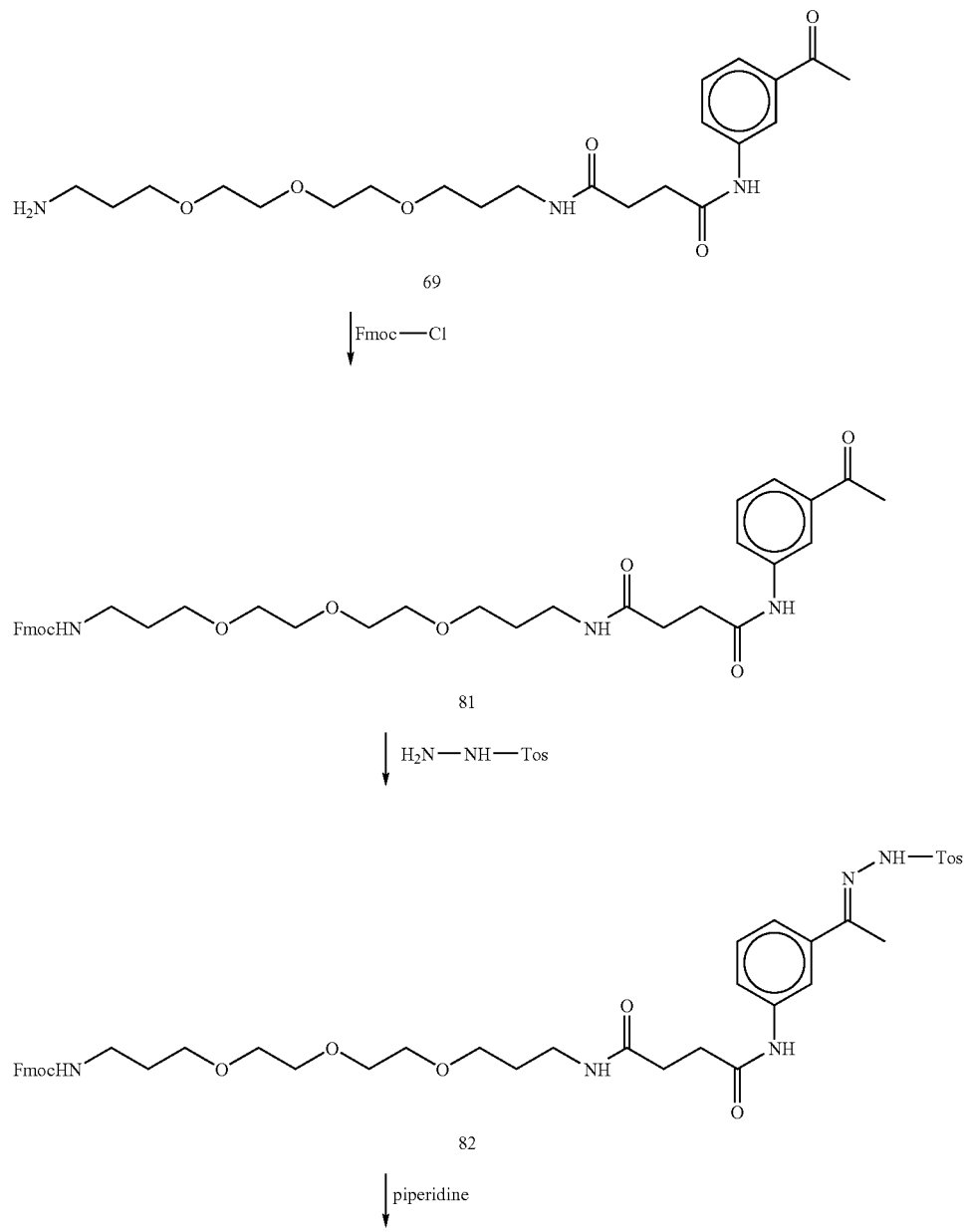

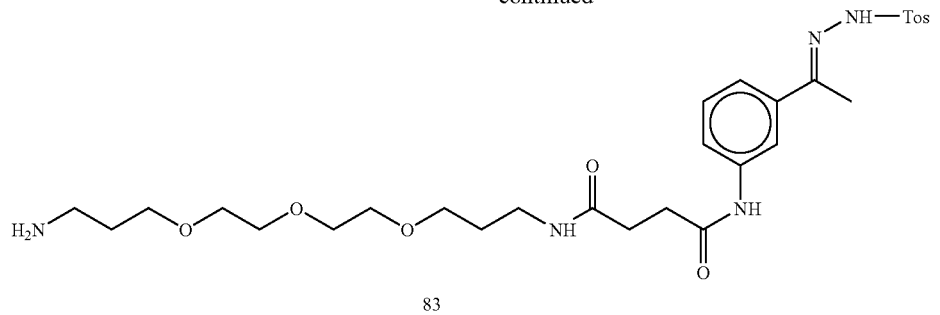

83

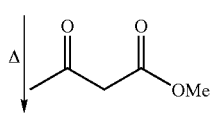

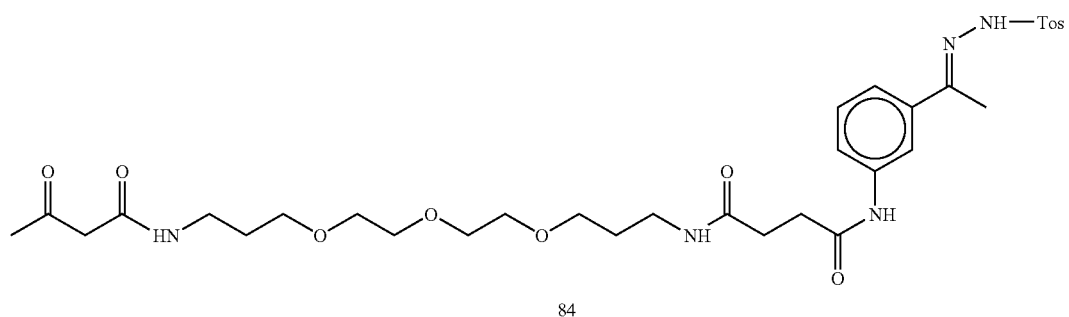

84

MnO₂

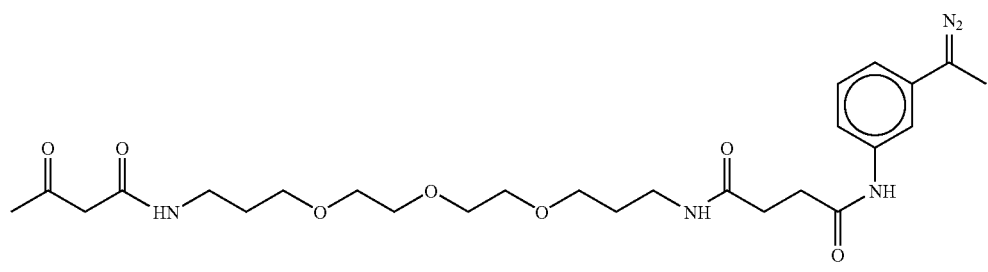

85
MeCO—PMDAM

Product 85, whose synthesis is described in this example, makes it possible to carry out the labeling of natural nucleic acids by virtue of the reactivity of the diazomethyl functional group with phosphate groups, and to thus introduce a methyl ketone functional group, which may be subsequently used to introduce a detectable (fluorescent, biotin) molecule possessing an alkoxyamine group.

This synthesis is based on known methods which are routinely used in chemistry. The starting material is the same as for the synthesis of the markers 71 and 74. The first step consists in the protection of the terminal amine with Fluorenylmethyl formate (Fmoc, 99). The choice of this protecting group is based on its stability and cleavage conditions.

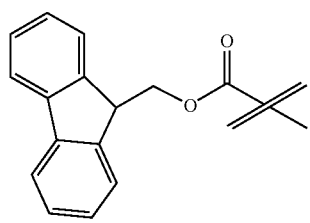

99 example), the terminal amine is deprotected under gentle basic conditions which ensure the stability of the hydrazone. Methyl acetoacetate is used to create the methyl ketonefunctional group by a reaction of acylation of the terminal amine (see formation of compounds 26 and 36). The formation of the diazomethyl is then carried out by one of the methods described above.

EXAMPLE 25.2

After formation of the protected hydrazone 82 by the method previously used (meta-Fluo-EG$_3$-PMDAM Synthesis of H$_2$NO-PMDAM

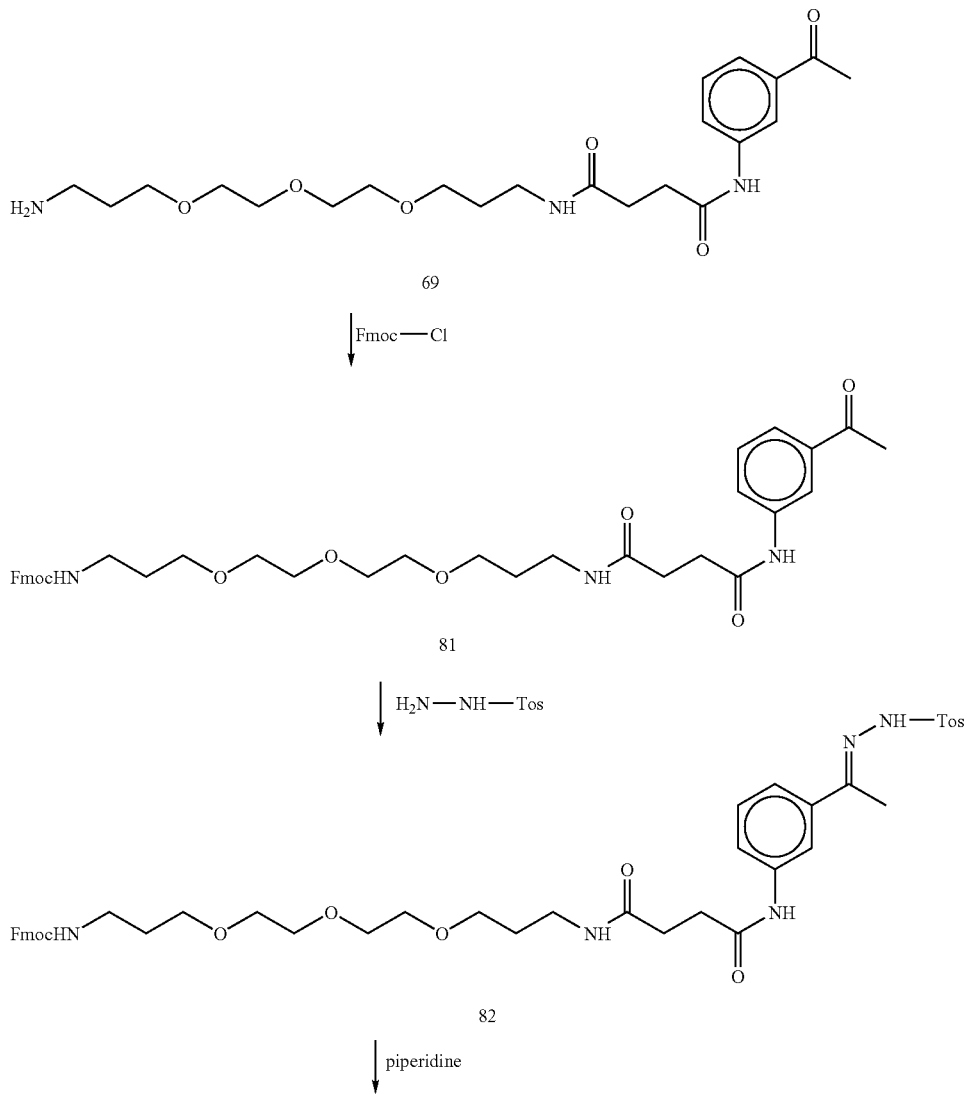

Synthesis scheme:

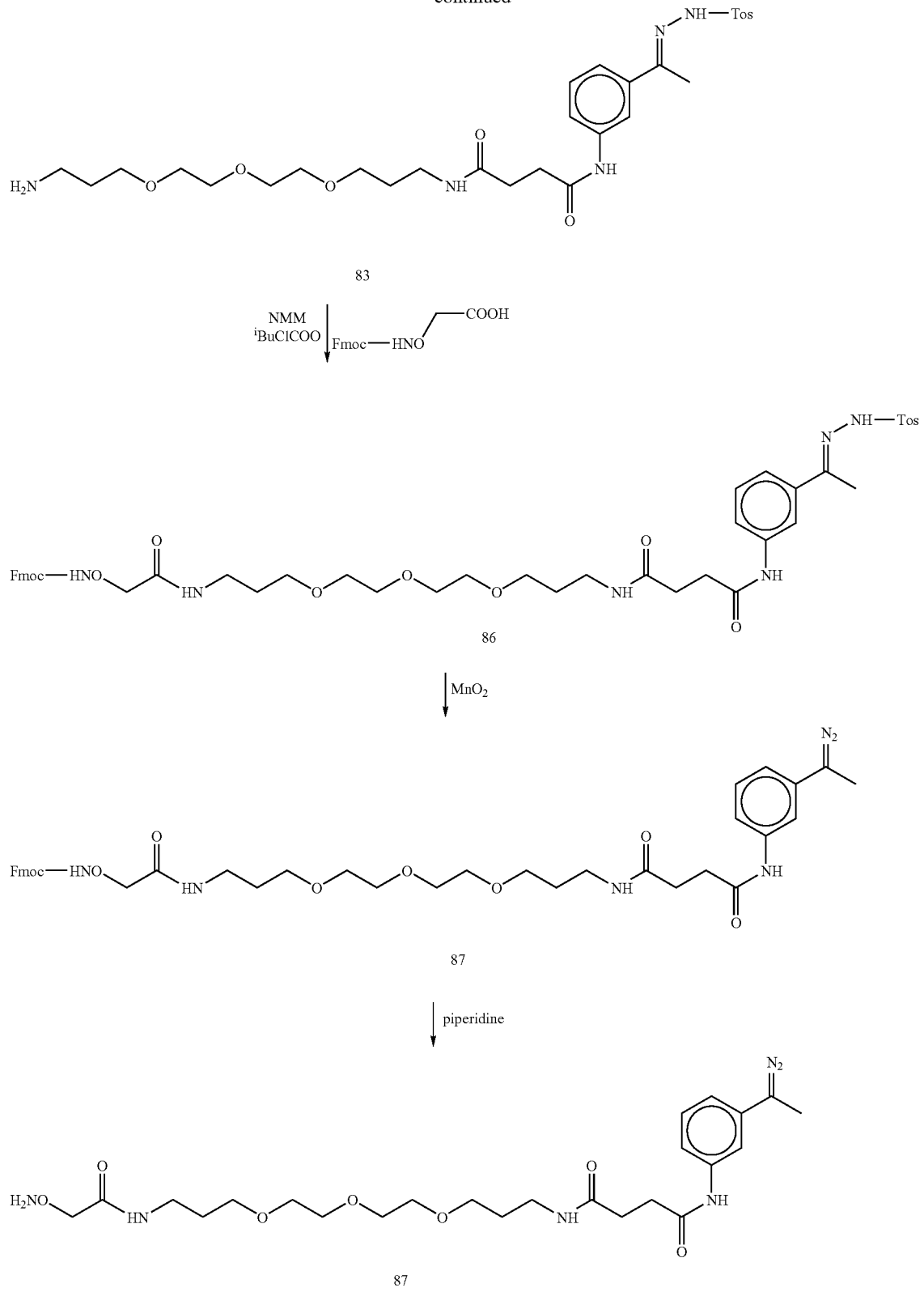

The product 88, whose synthesis is described in this example, makes it possible to carry out the labeling of natural nucleic acids, by virtue of the reactivity of the diazomethyl functional group with phosphate groups, and to thus introduce an alkoxyamine functional group, which may be subsequently used to introduce a detectable (fluorescent, biotin) molecule possessing a methyl ketone group.

This synthesis is based on the model of the preceding synthesis, that is to say the use of the precursor 69, of Fmoc for the protection of the amine and of tosyl for the protection of the hydrazone. The introduction of the alkoxyamine functional group (compound 86) takes place using the carboxymethoxylamine (commercial) protected by the Fmoc functional group (E. Trévisiol Thesis, LEDSS Grenoble, 1999). Given the gentle conditions for the final deprotection (compound 88), the latter is carried out immediately after the formation of the diazomethyl.

EXAMPLE 26

Preparation of the PDAM Derivatives Allowing the Amplification of the Signal

EXAMPLE 26.1

Synthesis of the Bis-Biotinylated Markers such as [Bio-EG3]2-PDAM

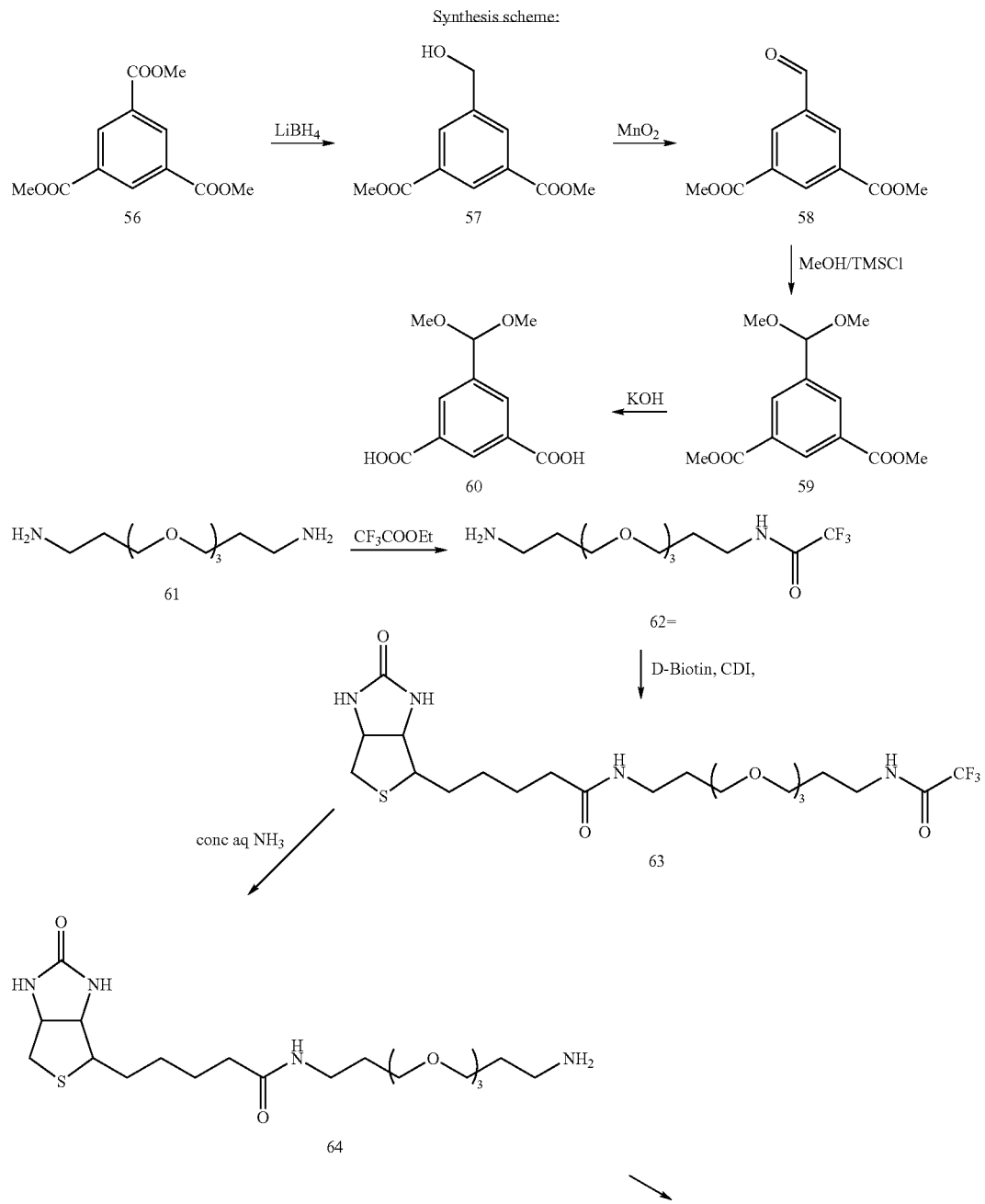

Synthesis scheme:

-continued
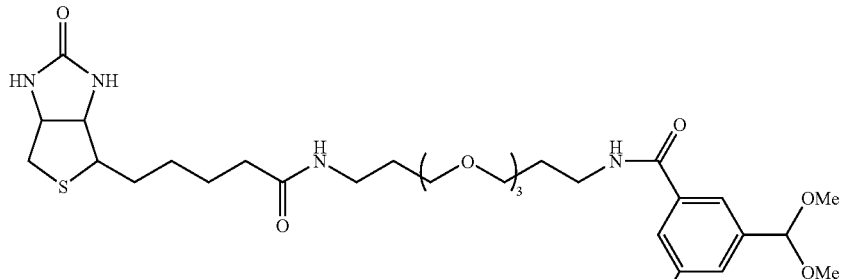
65
↓ HCl
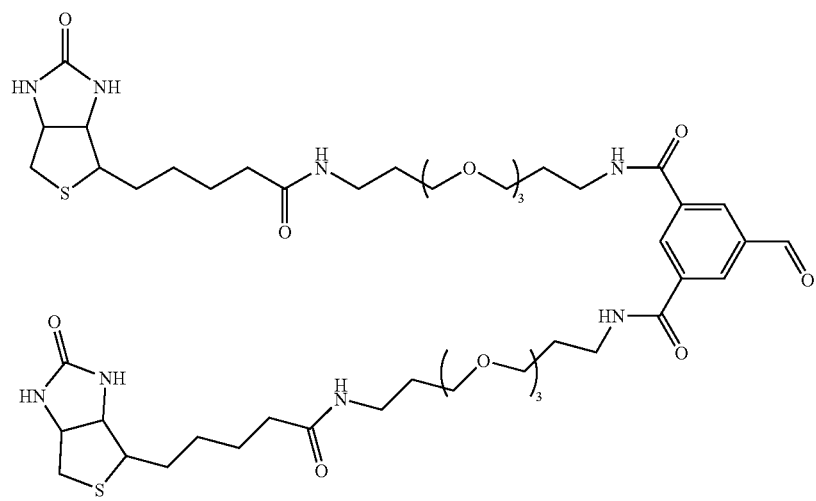
66
↓ 1 NH₂NH₂
2 MnO₂

-continued

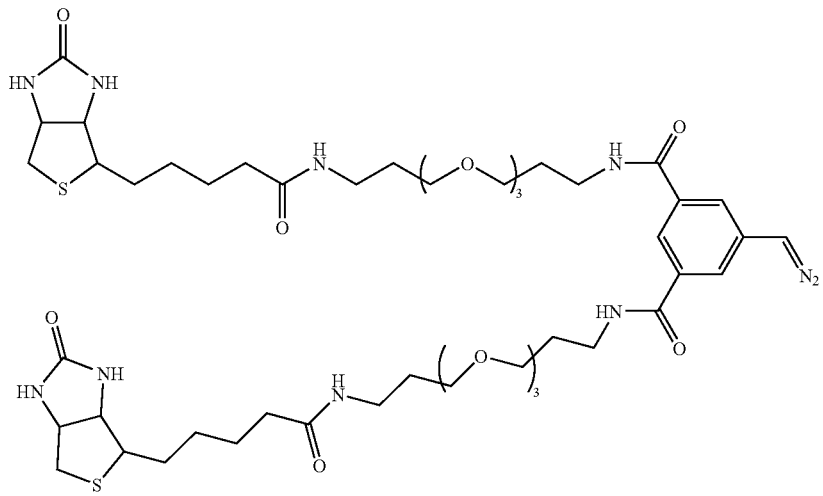

67

Reduction of trimethyl 1,3,5-benzenetricarboxylate 56 to the Alcohol 57:

The triester 56 (12.6 g; 50.0 mmol) is dissolved in 100 ml of THF and then 1.1 g (50.5 mmol) of LiBH$_4$ are added at room temperature. The red solution is heated at 40–45° C., with stirring under argon, for 1 h. After cooling (ice), the excess hydride is carefully destroyed (emission of H$_2$) by addition of water (200 ml) and then of 2N HCl (30 ml). The change of color to light yellow is observed. This solution is extracted with CH$_2$Cl$_2$ (100 ml and then 3 times 50 ml), the organic phase is washed with anhydrous NaHCO$_3$, dried over MgSO$_4$, and then the solvent is evaporated until an oil (11.1 g) is obtained. Using flash chromatography on a silica column (diameter=40 mm, eluent: ethyl acetate/cyclohexane=1/1), the alcohol 57 (6.38 g, 57%) is obtained.

$^1$H NMR (200 MHz, CDCl$_3$): δ=8.53 (t, 1H, J=2 Hz) 8.18 (d, 2H, J=2 Hz); 4.76 (s, 2H); 3.91 (s, 6H); 2.30 (s, 1H).

Oxidation of the Alcohol 57 to Aldehyde 58:

The alcohol 57 (5.86 g; 26.1 mmol) is dissolved in 100 ml of THF and then 40.0 g of MnO$_2$ are added little by little over 5 min at room temperature. The solution is kept stirred overnight under argon. The solution is filtered through a Büchner funnel provided with a layer of celite 545, washed with CH$_2$Cl$_2$ and then the solvents are evaporated. The crude solid (4.4 g) is purified by flash chromatography on a silica column (diameter=50 mm, eluent: ethyl acetate/cyclohexane 3/7). 3.44 g (59%) of the aldehyde 58 are obtained.

$^1$H NMR (200 MHz, CDCl$_3$): δ=10.11 (s, 1H); 8.89 (t, 1H, J=1 Hz); 8.69 (d, 2H, J=1 Hz); 3.98 (s, 6H).

Formation of the Acetal 59:

The aldehyde 58 (3.21 g; 14.4 mmol) is dissolved in 30 ml of methanol and then 6.0 ml of TMSCl are added. The solution is kept stirred at room temperature under argon for 1 h. The solution is diluted with 200 ml of CH$_2$Cl$_2$, and stirred with 1M NaHCO$_3$ (100 ml) (caution emission of CO$_2$). The two phases are separated, the aqueous phase is extracted three times with CH$_2$Cl$_2$ (25 ml), the organic phases are combined, dried over MgSO$_4$ and then the solvent is evaporated. 3.55 g (92%) of the acetal 59 are obtained.

$^1$H NMR (200 MHz, CDCl$_3$) δ=8.63 (t, 1H, J=2 Hz); 8.29 (d, 2H, J=2 Hz); 5.45 (s, 2H); 3.93 (s, 6H) 3.32 (s, 6H).

Hydrolysis of the Diester 59 to the Diacid 60:

The diester 59 (3.18 g; 11.9 mmol) is dissolved in 10 ml of THF and then a KOH solution (2.0 g, pellet 85%) in 10 ml of methanol is added. After 15 min at room temperature, the solvents are evaporated. The residue is dissolved in H$_2$O (50 ml). H$_3$PO$_4$ (about 2.5 ml, 85%) is added to pH 3 and the white precipitate is filtered on sintered glass (#3), washed with water and dried under vacuum. 2.59 g (91%) of the diacid 60 are obtained.

$^1$H NMR (200 MHz, DMSO-d$_6$): δ=8.43 (t, 1H, J=1 Hz); 8.15 (d, 2H, J=1 Hz); 5.53 (s, 1H); 3.27 (s, 6H).

Trifluoroacetamide 62:

The diamine 61 (66 g; 0.30 mol) is dissolved in 250 ml of CH$_2$Cl$_2$ and then ethyl trifluoroacetate (11.8 ml, 0.10 mol) is added dropwise over 5 min at 10° C. with stirring under argon. After 15 min at room temperature, the solution is transferred to a separating funnel, washed with H$_2$O (3×100 ml), dried over MgSO$_4$ and the solvent evaporated. 22.4 g (71%) of the monoamide 62 having a purity of about 85% (determined by $^{19}$F NMR) are obtained. This compound is stored at −20° C. and used without purification.

$^1$H NMR (200 MHz, CDCl$_3$): δ=3.5–3.6 (m, 12H); 3.42 (t, 2H, J=6 Hz); 2.75 (t, 2H, J=6 Hz); 1.81 (quantiplet, 2H, J=6 Hz); 1.67 (quantiplet, 2H, J=6 Hz); 1.30 (broad s, 2H).
$^{19}$F NMR (190 MHz, CDCl$_3$): δ=−76.3.

Compound 63:

To a suspension of D-biotin (6.39 g; 26.2 mmol) in 50 ml of DMF, carbonyldiimidazole (CDI, 6.32 g, 80%, 31.2 mmol) is added. The mixture is heated at 55–60° C., with stirring under argon, for 30 min. Complete dissolution of the material is initially observed followed by collection into a mass with precipitation of a white solid (CO$_2$ emission). The amine (oil) is added with the aid of 5 ml of CH$_2$Cl$_2$ in order to rinse and the mixture is heated at 55–60° C. for 3 h. The DMF is evaporated under vacuum (<1 mmHg) and the residue is stirred with CH$_2$Cl$_2$ (700 ml) and 2N HCl (100 ml). After filtration of the two phases through a layer of celite 545, the phases are separated, the aqueous phase is extracted with CH$_2$Cl$_2$ (15×100 ml), the organic phases are combined, dried over anhydrous NaHCO$_3$ and MgSO$_4$, and then the solvent is evaporated. The oily residue is triturated with 150 ml of ether to give a suspension. The pasty solid is difficult to filter. The supernatant is decanted off and the washing with ether is repeated. After drying under vacuum, 9.13 g (64%) of compound 63 are obtained.

$^1$H NMR (200 MHz, CDCl$_3$): δ=3.5–3.6 (m, 12H); 3.42 (t, 2H, J=6 Hz); 2.75 (t, 2H, J=6 Hz); 1.81 (quantiplet, 2H, J=6 Hz); 1,67 (quantiplet, 2H, J=6 Hz); 1.30 (broad s, 2H).

Compound 64:

A solution of compound 63 in aqueous ammonia (100 ml, 22% aqueous) is heated in a 250 ml round-bottomed flask with a septum at 55–60° C. for 2 h. After cooling, the solvent is evaporated. The residue is dissolved in methanol (20 ml) and passed over a column of Dowex 21K anion-exchange resin [height 12 cm×diameter 35 mm, OH⁻ form obtained by prior washing with 1N NaOH (1.5 l) and then H$_2$O (1.5 l) and then methanol (1.5 l)]. The compound 64 free of the trifluoroacetate ion passes in the first fractions with 200 ml of methanol. After evaporation, the residue is triturated with 50 ml of ether and then it is decanted off. The washing with ether is repeated five times in succession. After drying, the compound 64 (6.43 g, 86%) is obtained.

$^1$H NMR (300 MHz, CDCl$_3$): δ=6.77 (t, 1H, J=4 Hz); 6.32 (s, 1H); 5.52 (s, 1H): 4.45 (m, 1H); 4.28 (m, 1H); 3.50–3.68 (m, 12H); 3.30 (m, 2H), 3.11 (m, 1H); 2.86 (dd, 1H, J=13 and 5 Hz), 2.75 (t, 2H, J=13 Hz), 2.68 (d, 1H, J=13 Hz); 2.16 (t, 2H, J=7 Hz); 1.60–1.85 (m, 8H); 1.41 (m, 2H).

[Bio-EG$_3$]$_2$-acetal 65:

To a suspension of the diacid 60 (120 mg; 0.500 mmol) in dichloroethane (5 ml), carbonyl-diimdazole (225 mg, 90%, 1.25 mmol) is added and the mixture is heated at 55–60° C. for 30 min, with stirring under argon. The amine 64 (550 mg; 1.23 mmol) is added and the solution is heated at 55–60° C. for 6 h. After evaporation, the residue is passed over a silica column (diameter: 25 mm, eluent: methanol 15–30% in CH$_2$Cl$_2$). 413 mg (75%) of compound 65 are obtained.

$^1$H NMR (300 MHz, CDCl$_3$): δ=8.34 (s, 1H); 8.06 (s, 2H); 7.87 (m, 2H); 6.85 (m, 2H); 6.60 (s, 2H); 5.93 (s, 2H): 5.40 (s, 1H); 4.45 (m, 2H); 4.27 (m, 2H), 3.43–3.68 (m, 24H); 3.31 (s, 6H); 3.25 (m, 4H), 3.08 (m, 2H); 2.83 (dd, 2H, J=13 and 5 Hz), 2.70 (t, 2H, J=13 Hz); 2.13 (t, 4H, J=7 Hz); 1.89 (quintuplet, 4H, J=7 Hz); 1.55–1.70 (m, 12H); 1,37 (m, 4H).

[Bio-EG$_3$]$_2$-aldehyde 66:

The acetal 65 (413 mg; 0.376 mmol) dissolved in methanol is treated with 2N HCl (0.5 ml). After evaporation and washing with ether, the aldehyde 66 (0.37 g, 90%) is obtained.

$^1$H NMR (300 MHz, DMSO-d$_6$): δ=10.11 (s, 1H); 8.82 (t, 2H, J=6 Hz); 8.62 (s, 1H); 8.47 (s, 2H); 7.73 (t, 2H, J=5 Hz); 4.30 (m, 2H); 4.11 (m, 2H), 3.30–3.60 (m, 24H); 3.06 (m, 6H); 2.80 (dd, 2H, J=12 and 5 Hz), 2.56 (t, 2H, J=12 Hz); 2.03 (t, 4H, J=7 Hz); 1.78 (quintuplet, 4H, J=7 Hz); 1.35–1.60 (m, 12H); 1.28 (m, 4H).

[Bio-EG$_3$]$_2$-PDAM 67:

The aldehyde 66 is converted to the diazomethane 67 according to the method used for the preparation of diazomethanes (Example 1).

The stability of the reagent is greater than 1 month at −20° C.

EXAMPLE 26.2

Synthesis of meta-Bio7-EG3-PMDAM

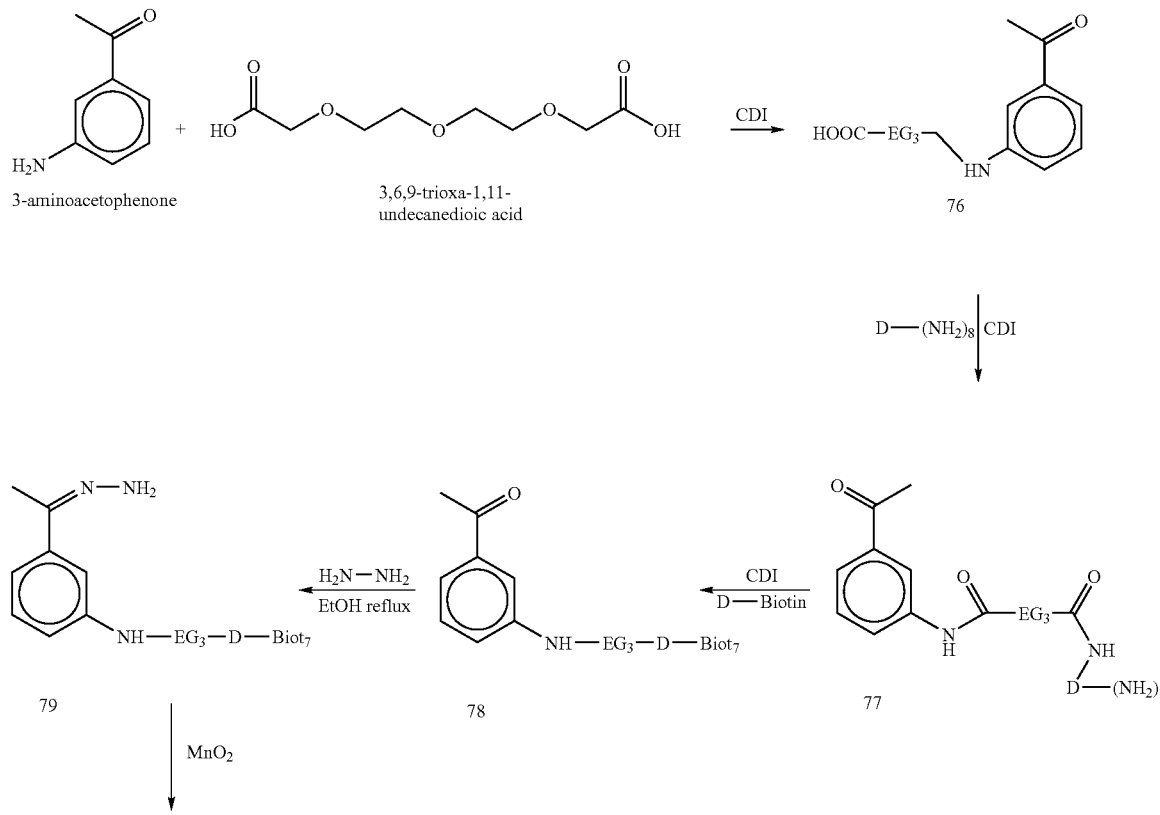

-continued

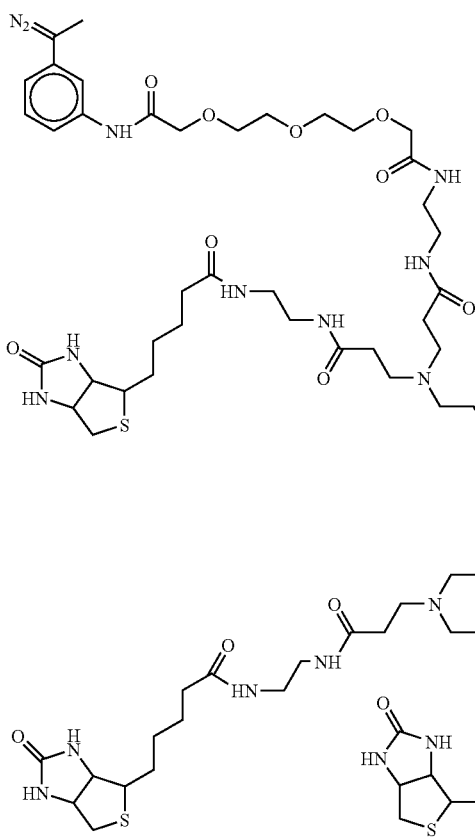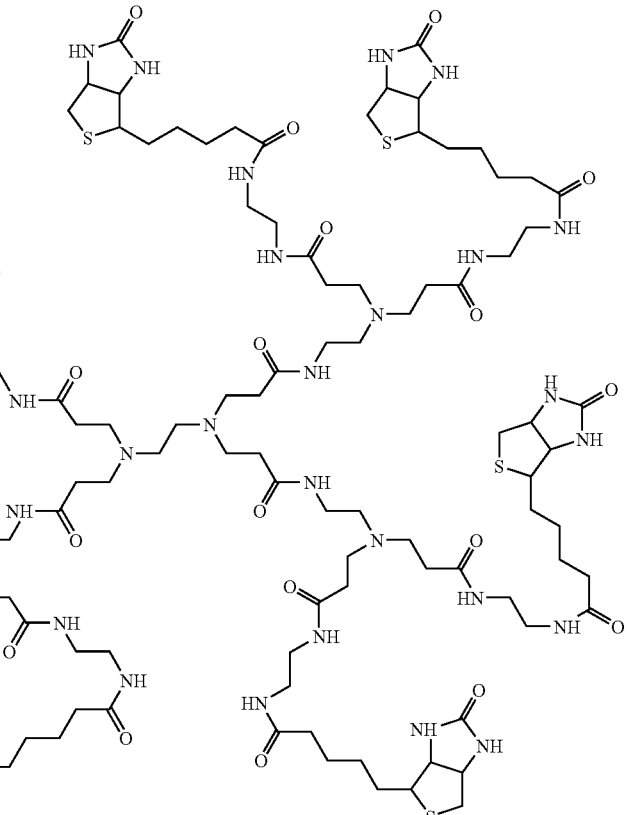

meta-Bio₇—EG₃—PMDAM
80

EG₃-acetophenone Compound 76:

3,6,9-Trioxa-1,11-undecanedioic acid (EC₃, 12.64 ml, 74 mmol) is dissolved in 80 ml of anhydrous DMF under argon and cooled on an ice bath. Dicyclohexylcarbodiimide (DCC, 11.45 g, 55.5 mmol) is then dissolved in 20 ml of anhydrous DMF and slowly added. After 30 min, 3-aminoacetophenone (5.0 g, 37 mmol) is added and the reaction is allowed to proceed for 1 h at room temperature under argon. The DMF is then evaporated under vacuum and 70 ml of CH₂Cl₂ are added. The solution is filtered and extracted with 3×25 ml of 1% acetic acid. The aqueous phases are combined and washed with 25 ml of CH₂Cl₂. The organic phases are mixed, dried over anhydrous sodium sulfate and evaporated to dryness. The product is recrystallized from the MeOH: H₂O pair. 8.74 g (70%) of product 76 are thus obtained.

$^1$H NMR (200 MHz, DMSO-d₆): δ=2.55 (s, 3H); 3.5–3.7 (m, 8H); 4.0 (s, 2H); 4.1 (s, 2H); 7.45 (t, 1H); 7.65 (d, 1H); 7.90 (d, 2H); 8.2 (s, 1H); 9.8 (s, 1H).

(NH₂)₇-EG₃-acetophenone Compound 77:

The product 76 (120 mg, 0.35 mmol) is dissolved in 15 ml of anhydrous DMF under argon, cooled on ice, and DCC (110 mg, 0.53 mmol) is then added. After 30 min, this solution is added over a solution of the commercial dendrimer "Starburst PAMAM Dendrimer, Generation 1" (Aldrich, St Quentin Fallavier) (1 g, 0.71 mmol, in 5 ml of methanol), slowly and with vigorous stirring. The reaction is allowed to proceed for 1 h at room temperature and the mixture is evaporated. The residue is taken up in 10 ml of CH₂Cl₂ and extracted twice with 30 ml of 1% acetic acid.

Biot₇-EG₃-acetophenone Compound 78:

D-biotin (1.73 g, 7.08 mmol) is solubilized in 80 ml of anhydrous DMF under argon, and the solution is cooled on ice. N-methylmorpholine (NMM, 856 μl, 7.7 mmol) and isobutyl chloroformate (1 022 μl, 7.7 mmol) are successively added. After 30 min, the product 77 (1.13 g, 0.7 mmol, in 5 ml of methanol) is added and the reaction is allowed to proceed for 3 h on ice and under argon. The mixture is concentrated under vacuum to 50 ml and 100 ml of CH₂Cl₂ are added. A precipitate forms, which is filtered, washed with ether and dried under vacuum. 1.3 g of 78 are obtained in the form of a white powder.

Biot₇-EG₃-Hydrazone Compound 79:

The compound 78 (300 mg, 0.09 mmol) is dissolved in 10 ml of absolute ethanol under reflux. Hydrazine monohydrate (20 ml, 0.40 mmol) is added and the reaction is allowed to proceed for 3 h under reflux. After cooling, a precipitate forms, which is filtered, washed with ether and dried under vacuum. 109 mg (36%) of the product 79 are thus obtained in the form of a white powder.

Biot₇-EG₃-PMDAM Compound 80:

The hydrazone 79 (100 mg, 0.03 mmol) is solubilized in 5 ml of anhydrous DMF at 70° C. The mixture is allowed to return to room temperature and MnO₂ (31 mg, 0.36 mmol) is added. The reaction is allowed to proceed for 10 min and the manganese oxide is removed by filtration on sintered glass with celite (0.5 cm) and powdered molecular sieve (0.5 cm). The filtrate is evaporated to dryness, washed with ether and dried under vacuum. 78 mg (78%) of product 80 are thus obtained.

Dendrimers are arborescent molecules possessing, at the ends, several reactive groups such as amines, carboxyls, hydroxyls and the like (for a review, see Newcome et al., (1996) *Dendritic Molecules: Concept, Syntheses, Perspectives*. VCH Ed., Weinheim, Germany). The synthesis of these molecules is nowadays perfectly controlled, and many dendrimers are marketed by the chemical industry. The choice of PAMAM (Sigma-Aldrich) was made on the basis of its stability, solubility and flexibility, since several versions of this molecule, with different number and type of endings, are available. "PAMAM Generation 1" makes it possible to add seven molecules of the marker (in a single synthesis step) for each diazomethyl group.

EXAMPLE 27

Labeling and Fragmentation in Two Steps of DNA Amplicons with meta-BioPMDAM

The DNA amplicons were prepared by PCR amplification according to the protocol described in Example 5. Two labeling reactions were carried out.

a. Labeling and Fragmentation in Two Steps:

To 10 µl of PCR there are added 10 µl of meta-BioPMDAM (100 mM in DMSO) and 77 µl of DNase/RNase-free water. The solution is incubated for 10 min at 95° C. 3 µl of 0.1M HCl are then added and the solution is incubated for 10 min at 95° C.

b. Labeling and Fragmentation in One Step:

To 10 µl of PCR there are added 10 µl of meta-BioPMDAM (100 mM in DMSO), 5 µl of 0.1M HCl and 75 µl of DNase/RNase-free water. The solution is incubated for 30 min at 60° C.

The remainder of the protocol is identical to that of Example 9.

Results:

TABLE 13

Comparative study of the labeling and fragmentation in two distinct steps and in a single step

| Protocol used | Homology (%) | I (rfu) | B (rfu) | I/B |
|---|---|---|---|---|
| a. Labeling and fragmentation in two steps | 99.5 | 14129 | 624 | 22.7 |
| b. Labeling and fragmentation in one step | 98.9 | 4431 | 667 | 6.6 |

As demonstrated in Table 13, the results obtained with the protocol in one step are satisfactory. Those obtained with a labeling and a fragmentation in two steps are even better. This example shows that the labeling and cleavage steps may be separated in order to improve the labeling according to the target used.

EXAMPLE 28

Labeling and Fragmentation of DNA Amplicons in Various Reaction Formats

The DNA amplicons were prepared by PCR amplification according to the protocol described in Example 5. Three labeling reactions were carried out.

a. Labeling and Fragmentation in a 250 µl Format:

To 50 µl of PCR there are added 75 µl of meta-BioPMDAM (100 mM in DMSO) and 102.5 µl of DNase/RNase-free water. The solution is incubated for 25 min at 95° C. 22.5 µl of 0.1M HCl are then added and the solution is incubated for 5 min at 95° C.

b. Labeling and Fragmentation in a 200 µl Format:

To 50 µl of PCR there are added 75 µl of meta-BioPMDAM (100 mM in DMSO) and 52.5 µl of DNase/RNase-free water. The solution is incubated for 25 min at 95° C. 22.5 µl of 0.1M HCl are then added and the solution is incubated for 5 min at 95° C.

c. Labeling and Fragmentation in a 150 µl Format:

To 50 µl of PCR there are added 75 µl of meta-BioPMDAM (100 mM in DMSO) and 2.5 µl of DNase/RNase-free water. The solution is incubated for 25 min at 95° C.

22.5 µl of 0.1M HCl are then added and the solution is incubated for 5 min at 95° C.

The remainder of the protocol is identical to that of Example 9.

Results:

TABLE 14

Labeling and fragmentation according to different formats

| Protocol used | Homology (%) | I (rfu) | B (rfu) | I/B |
|---|---|---|---|---|
| a. 250 µl format | 100.0 | 5606 | 549 | 10.2 |
| b. 200 µl format | 99.4 | 5886 | 557 | 10.6 |
| c. 150 µl format | 99.4 | 6800 | 537 | 12.7 |

The results obtained in terms of signal and percentage homology are very satisfactory in all cases. Furthermore, although the reaction format varies from 150 to 250 µl, the results have similar values.

This example shows a flexibility of the reaction format of the labeling protocol which can accept different volumes and in particular different volumes of amplification products.

EXAMPLE 29

Comparison between a Protocol Using a Purification Step before Fragmentation and a Protocol Using a Purification Step After Fragmentation The DNA amplicons were prepared by PCR amplification according to the protocol described in Example 5. Two labeling reactions were carried out.

a. Labeling, Purification and then Fragmentation of the DNA Amplicons:

To 10 µl of PCR there are added 10 µl of meta-BioPMDAM (100 mM in DMSO) and 80 µl of DNase/RNase-free water. The solution is incubated for 10 min at 95° C. The purification is then carried out according to the protocol described in Example 9. To the solution of purified labeled amplicons 6 µl of 0.1M HCl are added. The solution is incubated for 10 min at 95° C. Four hundred (400) µl of hybridization buffer, preheated at 95° C. for 10 min, are added.

The composition of the hybridization buffer and the remainder of the protocol are identical to that of Example 9.

b. Labeling, Fragmentation and then Purification of the DNA Amplicons:

To 10 μl of PCR there are added 10 μl of meta-BioPM-DAM (100 mM in DMSO) and 77 μl of DNase/RNase-free water. The solution is incubated for 10 min at 95° C.

3 μl of 0.1M HCl are then added and the solution is again incubated for 10 min at 95° C. The remainder of the protocol is identical to that of Example 9.

Results:

TABLE 15

Comparison between a protocol using a purification step before fragmentation and a protocol using a purification step after fragmentation

| Protocol used | Homology (%) | I (rfu) | B (rfu) | I/B |
|---|---|---|---|---|
| a. Purification before fragmentation | 98.9 | 6256 | 473 | 13 |
| b. Fragmentation before purification | 96.1 | 6066 | 556 | 11 |

This result, presented in Table 15, shows that the purification step may be introduced between the labeling and fragmentation steps. Furthermore, the introduction of purification between the labeling and fragmentation steps makes it possible to carry out the denaturation during the cleavage and to hybridize onto the chip all of the labeled amplicon fragments.

EXAMPLE 30

Synthesis of 2-nitro-para-BioPDAM

Synthesis scheme:

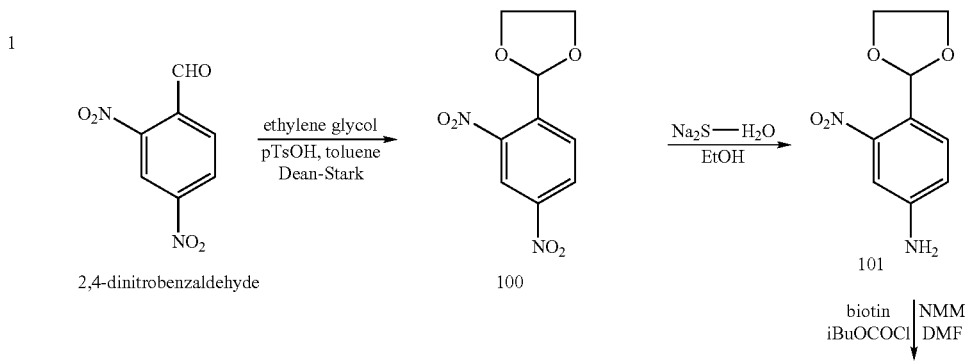

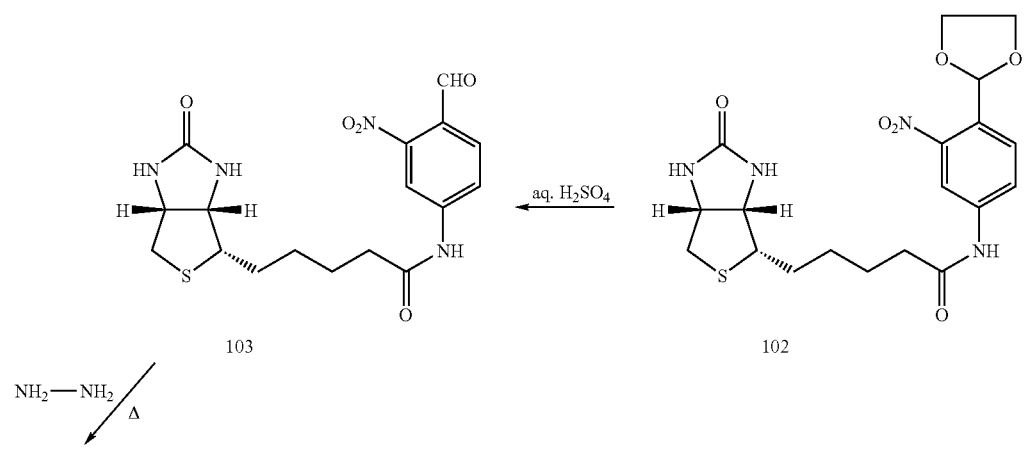

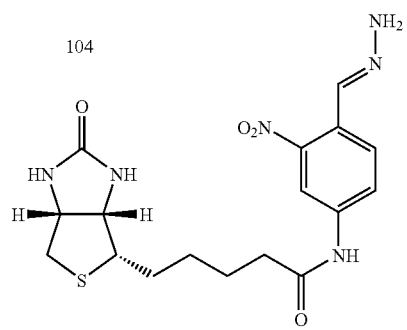 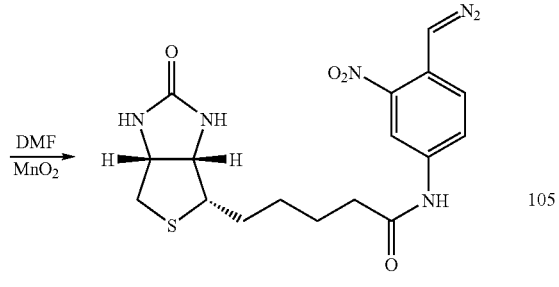

2-nitro-para-BioPDAM

Protection of the Aldehyde:

5 g (25.5 mmol) of 2,4-dinitrobenzaldehyde are dissolved in 250 ml of toluene, and 20 ml of ethylene glycol and 150 mg of para-toluenesulfonic acid are added. The mixture is heated under reflux, the water being recovered in a Dean-Stark system for 6 h. The mixture is treated with 150 ml of EtOAc and 100 ml of H$_2$O. The solution is extracted twice with ethyl acetate, the organic phase is dried with MgSO$_4$ and then evaporated. The oil obtained, corresponding to product 100, is used for the next reaction.

$^1$H NMR (200 MHz, CDCl$_3$) δ=8.70 (d, 1H$_{aro}$, J=2 Hz, H$_3$); 8.44 (dd, 1H$_{aro}$, J=2 Hz, J=6 Hz, H$_5$); 8.02 (d, 1H$_{aro}$, J=8 Hz, H$_6$); 6.49 (s, 1H, CH); 4.12–4.06 (m, 4H, CH$_2$—CH$_2$).

Reduction of the Dinitro Derivative 100:

The protected 2,4-dinitrobenzaldehyde (6.4 g; 25.5 mmol) is dissolved in an ethanol-water (6/1) mixture, and then 2 equivalents of Na$_2$S nonahydrate (12.3 g; 51.1 mmol) are added. The reaction mixture is then heated for 30 min. Evaporation and then extraction using dichloromethane are carried out. After drying and filtration, the reaction medium is evaporated so as to obtain an oil which is directly purified on a silica column (cyclohexane/ethyl acetate 60/40). Compound 101 is isolated with a yield of 45%.

Compound 101:

m.p. 58–60° C.—$^1$H NMR (200 MHz, CDCl$_3$) 7.49 (d, 1H$_{aro}$, J=2 Hz, H$_3$); 7.09 (d, 1H$_{aro}$, J=2 Hz, H$_6$); 6.80 (dd, 1H$_{aro}$, J=2 Hz, J=6 Hz, H$_5$); 6.27 (s, 1H, CH); 3.99–3.97 (m, 4H, CH$_2$—CH$_2$).

Coupling with Biotin:

D-biotin (1.0 g; 4.1 mmol) is solubilized in 20 ml of anhydrous DMF and 600 μl of N-methylmorpholine. Isobutyl chloroformate (700 μl; 5.5 mmol) is added under argon while cooling on an ice bath. The mixture is kept stirred for 5 min, and then 1 g (4.75 mmol) of compound 101 and 500 μl of N-methylmorpholine are added. The solution is kept stirred at room temperature for 4 h, and then evaporated to dryness. The oil obtained is directly passed over a silica column with, as elution solvent, MeOH-DCM 7% and then 10%. Product 102 (1.1 g; 2.52 mmol) is obtained with a yield of 62%.

$^1$H NMR (200 MHz, DMSO-d$_6$) δ=10.40 (s, 1H, NH—CO); 8.31 (d, 1H$_{aro}$, J=2 Hz, H$_3$); 7.77 (dd, 1H$_{aro}$, J=2 Hz, J=6 Hz, H$_5$); 7.68 (d, 1H$_{aro}$, J=2 Hz, H$_6$); 6.43 (broad s, 1H, NH—CO—NH); 6.36 (broad s, 1H, NH—CO—NH); 6.23 (s, 1H, CH); 4.28 (m, 1H, CH$_2$—CH—NH); 4.14 (m, 1H, CH—CH—NH); 3.92 (s, 4H, CH$_2$—CH$_2$); 3.12 (m, 1H, CH—S); 2.85 and 2.76 (system ABX, 2H, $^2$J$_{AB}$=5 Hz, $^3$J$_{AX}$=12 Hz, $^3$J$_{BX}$=0 Hz, CH$_2$—S); 2.29 (t, 2H, J=8 Hz, CH$_2$—CO); 1.61–1.39 (m, 6H, (CH$_2$)$_3$).

Deprotection of the Acetal:

The product 102 (768 mg; 1.76 mmol) is suspended in 25 ml of THF. The whole is dissolved after addition of 4 ml of 2N H$_2$SO$_4$. The mixture is kept stirred for 2 h. It is evaporated and then rinsed and washed with water on sintered glass. Compound 103 (694 mg) is obtained in the form of a yellow powder with a yield of 90%.

m.p. 165° C.—$^1$H NMR (200 MHz, DMSO-d$_6$) δ=10.69 (s, 1H, NH—CO); 10.09 (s, H, CHO); 8.43 (d, 1H$_{aro}$, J=2 Hz, H$_3$); 7.91 (s, 2H$_{aro}$, H$_5$ and H$_6$); 6.42 (broad s, 1H, NH—CO—NH); 6.35 (broad s, 1H, NH—CO—NH); δ6.23 (s, 1H, CH); 4.29 (m, 1H, CH$_2$—CH—NH); 4.13 (m, 1H, CH—CH—NH); 3.12 (m, 1H, CH—S); 2.84 and 2.78 (system ABX, 2H, $^2$J$_{AB}$=5 Hz, $^3$J$_{AX}$=12 Hz, $^3$J$_{BX}$=0 Hz, CH$_2$—S); 2.29 (t, 2H, J=8 Hz, CH$_2$—CO); 1.61–1.39 (m, 6H, (CH$_2$)$_3$).

Formation of the Hydrazone 104:

The aldehyde 103 is suspended in ethanol and the suspension is heated to 80° C. When hydrazine is added, the whole dissolves and the solution is immediately colored orange. A precipitate forms after 5 min. The mixture is heated with stirring for 1 h. It is filtered on sintered glass and then the precipitate is dried. Product 104 (700 mg; 690 mmol) is obtained with a yield of 98%.

m.p. 169° C.—$^1$H NMR (200 MHz, DMSO-d$_6$) δ=10.31 (s, 1H, NH—CO); 8.31 (d, 1H$_{aro}$, J=2 Hz, H$_3$); 7.96 (s, H, CHO); 7.87 (d, 1H$_{aro}$, J=2 Hz, H$_6$); 7.68 (dd, 1H$_{aro}$, J=2 Hz, J=6 Hz, H$_5$); 7.31 (s, 2H, NH$_2$); 6.42 (broad s, 1H, NH—CO—NH); 6.34 (broad s, 1H, NH—CO—NH); 4.29 (m, 1H, CH$_2$—CH—NH); 4.13 (m, 1H, CH—CH—NH); 3.12 (m, 1H, CH—S); 2.84 and 2.78 (system ABX, 2H, $^2$J$_{AB}$=5 Hz, $^3$J$_{AX}$=12 Hz, $^3$J$_{BX}$=0 Hz, CH$_2$—S); 2.29 (t, 2H, J=8 Hz, CH$_2$—CO); 1.61–1.39 (m, 6H, (CH$_2$)$_3$).

Formation of the Diazo 105:

Compound 104 (200 mg; 0.492 mmol) is dissolved in 8 ml of DMF. 400 mg of MnO$_2$ are added. The mixture is vigorously stirred for 10 min. It is filtered on millipore containing celite (thickness: 2 cm) and powdered molecular sieve 3 Å (0.5 cm). It is evaporated to dryness and then washed with ether. The mixture is again filtered on millipore. Compound 105 (180 mg; 0.445 mmol) is obtained in the form of an orange powder with a yield of 98%.

m.p. 155° C.—$^1$H NMR (200 MHz, DMSO-d$_6$) δ=10.21 (s, 1H, NH—CO); 8.60 (d, 1H$_{aro}$, J=2 Hz, H$_3$); 7.77 (d, 1H$_{aro}$, J=6 Hz, H$_5$); 7.22 (d, 1H$_{aro}$, J=6 Hz, H$_6$); 6.60 (s, H, CH—N); 6.41 (broad s, 1H, NH—CO—NH); 6.33 (broad S, 1H, NH—CO—NH); 4.29 (m, 1H, CH$_2$—NH—NH); 4.13 (m, 1H, CH—CH—NH); 3.12 (m, 1H, CH—S); 2.84 and 2.78 (system ABX, 2H, $^2$J$_{AB}$=5 Hz, $^3$J$_{AX}$=12 Hz, $^3$J$_{BX}$=0 Hz, CH$_2$—S); 2.29 (t, 2H, J=8 Hz, CH$_2$—CO); 1.61–1.39 (m, 6H, (CH$_2$)$_3$).

The reactivity of compound 105 was tested on uridine 3'-monophosphate followed by capillary electrophoresis. The analytical conditions are those of Example 6.1. The results show a Half-Reaction period of 45 minutes.

The stability of the reagent is greater than 1 month at −20° C.

EXAMPLE 31

Labeling and Fragmentation of the DNA Amplicons with the Labeling Reagent 2-nitro-para-BioPDAM The 2-nitro-para-BioPDAM derivative was obtained according to the reaction scheme described in Example 30. The DNA amplicons were prepared by PCR amplification according to the protocol described in Example 5. Two labeling reactions were carried out.

a. Labeling with the 2-nitro-para-BioPDAM Reagent:

To 10 μl of PCR there are added 2 μl of 2-nitro-para-BioPDAM (100 mM in DMSO), 5 μl of 0.1M HCl and 83 μl of DNase/RNase-free water. This solution is incubated for 30 min at 60° C.

b. Labeling with the meta-bioPMDAM Reagent:

To 10 μl of PCR there are added 2 μl of meta-BioPMDAM (100 mM in DMSO), 5 μl of 0.1M HCl and 83 μl of DNase/RNase-free water. This solution is incubated for 30 min at 60° C.

The remainder of the protocol is identical to that of Example 9.

Result:

TABLE 16

Comparative study of the labeling of DNA with the 2-nitro-para-BioPDAM derivative compared with the meta-BioPMDAM derivative

| Protocol used | Homology (%) | I (rfu) | B (rfu) | I/B |
|---|---|---|---|---|
| a. Labeling with the 2-nitro-para-BioPDAM reagent | 100.0 | 24392 | 899 | 27.1 |
| b. Labeling with the meta-BioPMDAM reagent | 98.9 | 21883 | 774 | 28.3 |

The 2-nitro-para-BioPDAM reagent used for the labeling of the DNA gives advantageous results in terms of labeling intensity and percentage homology.

EXAMPLE 32

Insertion of a Double Bond between the Diazomethyl Functional Group and the Phenyl Nucleus, Distancing of the DAM and Synthesis of a Molecule which is Particularly Suitable for this Distancing The objective aimed at is the distancing of the diazomethyl (DAM) functional group of the aromatic structure in order to minimize the effect of steric hinderance during the alkylation of the phosphates and also during the hybridization of the labeled nucleic acid with its complementary sequence.

Synthesis sheme:

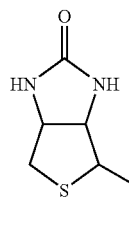
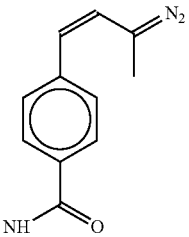

90

For the aldol reaction for formation of (para-methoxycarbonyl)styrylmethyl ketone 89, ethyl acetoacetate is used for the high acidity of the protons of the methylene, which facilitates attack of the formyl group, with subsequent elimination of $H_2O$ (promoted by the conjugation of the double bond with the aromatic ring) and decarboxylation with hydrolysis due to the basic medium. The remainder of the synthesis is similar to what was shown in the other examples.

The final product para-Bio-EG$_3$-SMDAM 90 possesses two more carbons between the diazomethyl and the aromatic ring, which limits the possible steric problems, while preserving the stabilization of the diazomethyl by the aromatic system by conjugation.

EXAMPLE 33

Capture and Detection of a Nucleic Acid on a Solid Support Carrying Diazomethyl Groups The reactivity of a resin carrying diazomethyl groups was studied to determine its capacity to bind nucleic acids.

4-(Diazomethyl)phenoxymethylpolystyrene (reference 17338, Fluka) is a resin described for its capacity to bind carboxyl groups, in particular those present in proteins (G. Bhalay, A. R. Dunstan, Tetrahedron Lett. 39, 7803–1998), but it is not described for its capacity to bind DNA molecules. We tested the possibility of capturing nucleic acids with this reagent, and of visualizing them by a calorimetric test.

The experiment is carried out with a portion of the reagents present in the HLA-DR oligo-detection kit (reference 33 202, bioMérieux, France, basic principle described in patent EP 549 776-B1), allowing the detection of nucleic acids amplified by PCR in microplates, by calorimetric reading. In the context of the experiment described, nucleic acids produced by PCR are caused to simultaneously react with the resin tested, and with a molecule of para-Bio-EG3-PDAM, whose synthesis is mentioned in Example 20. If the DNA reacts with the diazomethyl functional groups present on the two compounds, it will be possible to visualize it, after washing and removing the molecules which are non-covalently bound, using a colorimetric reaction involving an enzyme coupled to streptavidin. The streptavidin is combined with horseradish peroxidase, it being possible for this enzyme to decompose an OrthoPhenyleneDiamine molecule (Color 1 reagent of the kit) to a compound which can be detected at a wavelength of 492 nm.

EXAMPLE 33.1

Capture and Detection of the DNA 10 mg of resin are incubated for 30 minutes at 60° C. with 50 µl of PCR performed as described in Example 5, in 400 µl of pure water (Sigma) supplemented with 5 µl of para-Bio-EG3-PDAM. This resin is then washed with 500 µl of PBS Tween buffer (Color 0 HLA reagent of the kit, PBS pH 7.0; 1% Tween, 0.2 g/l BND; 0.01 g/l Ciproflaxacin). The resin is then resuspended in 100 µl of PBS Tween, and 250 µl of streptavidin hybridization buffer (PBS pH 7.0 0.5% TWEEN) supplemented with streptavidin HRP (S-911, MOLECULAR PROBES, EUGENE, Oreg., USA) diluted 1/10 000. The reaction mixture is incubated for 30 min at room temperature. The resin is then washed three (3) times with 500 µl of PBS Tween buffer, and it is incubated at room temperature in the presence of a chromogenic reagent (1 Color 1 Tablet, ortho-phenylenediamine hydrochloride, diluted in 5 ml of Color 2 buffer, 100 mM sodium phosphate, 50 mM citric acid, 0.03% $H_2O_2$). After an incubation of 20 min in the dark, the reaction is then blocked with 50 µl of $H_2SO_4$ (1.8N Color 3 reagent). The supernatant is then pipetted and placed in a microplate in order to read the absorbence of the reaction medium at 492 nm.

EXAMPLE 33.2

Control without Nucleic Acid 10 mg of resin are incubated for 30 minutes at 60° C. in 425 µl of pure water (Sigma) supplemented with 5 µl of para-Bio-EG3-PDAM. This resin is then washed with 500 µl of PBS buffer. The sample is then treated in a manner identical to the process described in Example 33.1.

EXAMPLE 33.3

Control with PCR Carried out without Targets 10 mg of resin are incubated in 400 µl of pure water supplemented with 5 µl of para-Bio-EG3-PDAM for 30 minutes at 60° C., with 50 µl of PCR performed with a volume of 25 µl of pure water in place of the volume of the genomic DNA described. This resin is then washed with 500 µl of PBS buffer. The sample is then treated in a manner identical to the procedure described in Example 33.1.

EXAMPLE 33.4

Control with PCR without a Revealing Molecule 10 mg of resin are incubated with 50 µl of PCR in 400 µl of pure water for 30 minutes at 60° C. This resin is then washed with 500 µl of PBS buffer. The sample is then treated in a manner identical to the procedure described in Example 33.1.

EXAMPLE 33.5

Control with Noncaptured Nucleic Acid 10 mg of resin are incubated for 30 minutes at 60° C. with 400 µl of pure water supplemented with 5 µl of para-Bio-EG3-PDAM. This resin is then washed with 500 µl of PBS Tween buffer (Color 0 HLA reagent of the kit, PBS pH 7.0; 1% Tween, 0.2 g/l BND; 0.01 g/l Ciproflaxacin). The resin is then resuspended in 100 µl of PBS Tween, and 250 µl of streptavidin hybridization buffer supplemented with streptavidin HRP diluted 1/10 000. To this preparation are added 50 µl of a DNA preparation prepared as follows:

5 µl of para-Bio-EG3-PDAM and 70 µl of pure water are added to 25 µl of DNA obtained from a PCR prepared as described in Example 5. This mixture is incubated for 30 min at 60° C., and then the excess marker is removed by subjecting the preparation to purification on a QIAquick column (Nucleotide Removal Kit, Qiagen, Hilden, Germany) according to the protocol recommended by the supplier, carrying out a final elution in a volume of 50 µl.

The reaction mixture is incubated for 30 min at room temperature, and then it is treated according to the procedure described in Example 33.1.

Results

TABLE 17

Study of the reactivity of a resin carrying diazomethyl groups

| Conditions | Absorbence at 492 nm |
|---|---|
| Ex. 33.1: DNA captured on Resin | 527 |
| Ex. 33.2: without nucleic acid | 249 |
| Ex. 33.3: PCR without target | 261 |
| Ex. 33.4: Control without marker | 264 |
| Ex. 33.5: Noncaptured nucleic acid | 249 |

In Table 17, a high calorimetric value indicates a high concentration of enzymes in the reaction medium, corresponding to a large presence of nucleic acid carrying biotin derivatives. The controls indicate that the signal is not due to a nonspecific adsorption of the DNA to the bead, to a reaction of the para-Bio-EG3-PDAM on the resin, or to an adsorption of the streptavidin HRP on the resin, but indeed to the presence of DNA captured covalently and labeled with para-Bio-EG3-PDAM.

EXAMPLE 34

Labeling of a PCR Product Allowing its Capture and its Detection in a Microplate The possibility of labeling a DNA molecule with only one type of molecule carrying a diazomethyl functional group, so as to capture and to detect this nucleic acid in a single step, on a microplate, is shown in this example.

The experiment is carried out with a portion of the reagents present in the HLA-DR oligo-detection kit (reference 33 202, bioMérieux), allowing the detection of nucleic acids amplifed by PCR in microplates, by calorimetric reading. In the context of the experiment described, para-Bio-EG3-PDAM, whose synthesis is described in Example 20, is reacted with nucleic acids produced by PCR. The DNA reacts with the diazomethyl groups of the molecule, and thus becomes equipped with biotins grafted on its phosphate. It will then be possible to capture the nucleic acid by incubation on a microplate where streptavidin molecules are adsorbed, and to visualize it by a colorimetric reaction. A detection reagent is used which is also a streptavidin molecule, combined with horseradish peroxidase (HRP). Under the conditions used, the peroxidase can decompose an OrthoPhenyleneDiamine molecule (Color 1 reagent of the kit) to a compound which can be detected at a wavelength of 492 nm.

EXAMPLE 34.1

Capture and Detection of the DNA Derived from PCR, on a Microplate:

10 µl of DNA obtained by PCR amplification as described in Example 5 are labeled by incubating them for 30 min at 60° C. in 80 µl of pure water (Sigma) supplemented with 10 µl of para-Bio-EG3-PDAM. After labeling, the DNA is purified on a QIAquick column (Nucleotide Removal Kit, Qiagen, Hilden, Germany) according to the protocol recommended by the supplier, and the final eluate is collected in 50 µl of EB buffer (10 mM Tris EDTA, pH 8.5). Twenty (20) µl of this eluate are diluted in 180 µl of PEG buffer (0.1M $NaPO_3$; 0.5M NaCl; 0.65% Tween 20; 0.14 mg/ml salmon sperm DNA (Gibco); 2% PEG 4000) supplemented with streptavidin HRP (S-911, Molecular Probes, Eugene, Oreg., USA) diluted to 1/10 000. One hundred (100) µl of this preparation are then incubated for 1 hour at 37° C., either in a well of a streptavidin-coated Combiplate 8 (reference 95029263, Labsystem, Helsinki, Finland) or in a control well, from a Maxisorb strip (Nunc, Denmark).

EXAMPLE 34.2

Preparation of Controls

Controls are simultaneously prepared in the following manner:

A—Labeling Control without DNA:

Ninety (90) µl of pure water supplemented with 10 µl of para-Bio-EG3-PDAM are incubated for 30 min at 60° C. The reaction mixture is then treated in a manner similar to the procedure described above in Example 34.1.

B—Labeling Control without Markers:

Ten (10) µl of DNA obtained by PCR amplification, as described in Example 5, are incubated for 30 min at 60° C. in 90 µl of pure water. The reaction mixture is then treated in a manner similar to the procedure described above in Example 34.1.

All the strips are then washed with three times 100 µl of PBS Tween buffer (Color 0 HLA reagent of the kit, PBS pH 7.0; 1% Tween, 0.2 g/l BND; 0.01 g/l Ciproflaxacin) and the presence of streptavidin HRP is then visualized by addition of 100 µl of chromogenic reagent (1 Color 1 tablet, ortho-phenylenediamine hydrochloride, diluted in 5 ml of Color 2 buffer, 100 mM sodium phosphate, 50 mM citric acid, 0.03% $H_2O_2$), incubated for 20 min in the dark, the reaction then being blocked with 50 µl of $H_2SO_4$ (1.8N Color 3 reagent). The absorbence of the reaction medium is then measured at 492 nm.

Results:

TABLE 18

Detection of DNA captured and labeled with para-Bio-EG3-PDAM

| Conditions | Combiplate | Maxisorp control |
|---|---|---|
| A - labeled DNA | 1382 | 152 |
| B - nonlabeled DNA | 178 | 136 |
| C - without DNA | 140 | 192 |

The experiment, presented in Table 18, therefore shows that the DNA labeled with para-Bio-EG3-PDAM can be captured and detected in a single step in a microplate well. As the reaction controls indicate, the signal generated is only due to the DNA and does not result from a nonspecific adsorption of the nucleic acid to the wall of the microplate, or to streptavidin, or alternatively to a nonspecific reaction of streptavidin HRP with nonlabeled DNA, or with the plastic of the microplate.

EXAMPLE 35

Double labeling of a PCR Product Allowing its Capture and its Detection on a Microplate Type Solid Support The possibility of labeling with two molecules, carrying diazomethyl functional groups, and in a single step, a DNA molecule, so as to capture it and to detect it on a microplate, is shown in this example.

The experiment is carried out with a portion of the reagents present in the HLA-DR oligo-detection kit, allowing the detection of nucleic acids amplified by PCR in microplates, by simple calorimetric reading. In the context of the experiment described:

1-pyrenyldiazomethane (PDAM), and
para-Bio-EG3-PDAM.

are simultaneously reacted with nucleic acids produced by PCR.

If the DNA reacts with the diazomethyl functional groups present on the two compounds, it will be able to bind to a support carrying anti-pyrene antibodies, and it will be possible to visualize it with a streptavidin molecule combined with horseradish peroxidase. This enzyme can decompose a molecule of Ortho-PhenyleneDiamine, acting as revealing reagent, to a compound which can be detected at a wavelength of 492 nm.

EXAMPLE 35.1

Double Labeling of the DNA and Detection on a Microplate

Anti-pyrene antibodies were adsorbed onto eight (8)-well Maxisorp strips by incubating overnight at room temperature 100 µl of a solution of 1.1 µl of anti-pyrene antibodies diluted in 100 µl of bicarbonate buffer (0.05M pH 9.6) Such antibodies, called Rabbit anti-pyrene (Ref.: YSRT-AHP236) are available from Accurate Chemical & Scientific (Westbury, N.Y., United States of America). Of course, this might have been carried out with other commercially available antibodies, without there being divergent results compared with those which were obtained in this example.

10 µl of DNA obtained by PCR amplification, as described in Example 5, were then labeled by incubating them for 30 min at 60° C. in 40 µl of pure water (Sigma), 10 µl of para-Bio-EG3-PDAM, 2 µl of PDAM (P-1405, 1-pyrenyldiazomethane, Molecular Probes, Eugene, Oreg., USA) and 38 µl of DMSO.

After labeling, the DNA was purified using a QIAquick kit (QIAGEN) and the final eluate was collected in 50 µl of EB buffer (10 mM Tris EDTA, pH 8.5). Twenty (20) µl of this eluate were diluted in 180 µl of PEG buffer (0.1M $NaPO_3$; 0.5M NaCl; 0.65% Tween 20; 0.14 mg/ml salmon sperm DNA (Gibco); 2% PEG 4000) supplemented with streptavidin HRP (S-911, MOLECULAR PROBES, EUGENE, Oreg., USA) diluted 1/10 000. One hundred (100) µl of this preparation were then incubated for 1 hour at 37° C., either in an adsorbed Maxisorp strip well, or in a nonadsorbed control well.

EXAMPLE 35.2

Preparation of Controls

Controls were simultaneously prepared in the following manner:

A—Control for Labeling with para-Bio-EG3-PDAM Alone:

Ten (10) µl of DNA obtained by PCR amplification, as described in Example 5, are labeled by incubation for 30 min at 60° C. in 90 µl of pure water supplemented with 10 µl of para-Bio-EG3-PDAM. After labeling, the DNA is purified using a QIAquick kit and the final eluate is collected in 50 µl of EB buffer. Twenty (20) µl of this eluate are diluted in 180 µl of PEG buffer supplemented with streptavidin HRP diluted 1/10 000. One hundred (100) µl of this preparation are then incubated for 1 hour at 37° C., either in an adsorbed Maxisorp strip well, or in a nonadsorbed well.

B—Control for Labeling with PDAM Alone:

Ten (10) µl of DNA obtained by PCR amplification, as described in Example 5, are labeled by incubation for 30 min at 60° C. in 90 µl of pure water supplemented with 2 µl of PDAM and 38 µl of DMSO. After labeling, the DNA is purified using a QIAquick kit and the final eluate is collected in 50 µl of EB buffer. Twenty (20) µl of this eluate are diluted in 180 µl of PEG buffer supplemented with streptavidin HRP diluted 1/10 000. One hundred (100) µl of this preparation are then incubated for 1 hour at 37° C., either in an adsorbed Maxisorp strip well, or in a nonadsorbed well.

C—Control without Labeling:

Ten (10) µl of DNA obtained by PCR amplification, as described in Example 5, are incubated for 30 min at 60° C. in 100 µl of pure water. After labeling, the DNA is purified using a QIAquick kit and the final eluate is collected in 50 µl of EB buffer. Twenty (20) µl of this eluate are diluted in 180 µl of PEG buffer supplemented with streptavidin HRP diluted 1/10 000. One hundred (100) µl of this preparation are then incubated for 1 hour at 37° C., either in an adsorbed Maxisorp strip well, or in a nonadsorbed well.

The strips are then washed with three times 100 µl of PBS Tween buffer (Color 0) and then the presence of streptavidin HRP is visualized by addition of 100 µl of chromogenic reagent (Color 2), incubated for 20 min in the dark, the reaction then being blocked with 50 µl of $H_2SO_4$ (Color 3). The absorbence of the reaction medium is then measured at 492 nm.

Results:

TABLE 19

Double labeling of the DNA with PDAM and para-Bio-EG3-PDAM

| Conditions | Anti-pyrene antibodies adsorbed on a plate (rfu) | Nonadsorbed control plate (rfu) |
|---|---|---|
| Ex. 35.1: PDAM + para-Bio-EG3-PDAM-labeled DNA | 348 | 16 |
| Ex. 35.2.A: para-Bio-EG3-PDAM-labeled DNA | 44 | 19 |
| Ex. 35.2.B: PDAM-labeled DNA | 68 | 12 |
| Ex. 35.2.C: nonlabeled DNA | 75 | 19 |

The result of Table 19 clearly shows a large signal resulting from the capture of the DNA in the wells by the anti-pyrene antibodies, as well as the simultaneous labeling thereof with streptavidin HRP, which has become attached. As the absence of signal in the controls shows, this detection is specific for the labeled DNA, and is not due to the nonspecific adsorption of the DNA or of the streptavidin HRP to the plastic, or to a nonspecific binding of the enzyme to the captured DNA. This example therefore shows that it is possible to carry out a double labeling of the DNA in a single step, it being possible for this double labeling to be used to capture it and to detect it simultaneously.

EXAMPLE 36

Labeling of a PCR Product Simultaneously Allowing its Capture and its Detection by Complementary Nucleic Probes This experiment makes it possible to demonstrate that it is possible to specifically detect a DNA, said DNA being captured on a solid surface using the reactivity of the diazomethyl functional group toward a phosphate group of the DNA.

The experiment is carried out with a portion of the reagents present in the HLA-DR oligo-detection kit (reference 33 202, bioMérieux, France), allowing the detection of nucleic acids amplifed by PCR in microplates, by calorimetric reading. In the context of the experiment described, para-Bio-EG3-PDAM is reacted with nucleic acids produced by PCR. The DNA reacts with the diazomethyl functional groups of the molecule, and thus becomes equipped with biotins grafted on its phosphates. It will then be possible to capture the nucleic acid by incubation on a microplate where streptavidin molecules are adsorbed, and to visualize it by a probe consisting of an oligonucleotide complementary to the captured sequence, combined with horseradish peroxidase, it being possible for this enzyme to decompose colorless molecules of OrthoPhenyleneDiamine (Color 1 reagent of the kit) to a compound which can be detected at a wavelength of 492 nm.

EXAMPLE 36.1

Capture and Specific Detection of the DNA on a Microplate

The labeling of 10 μl of DNA obtained by PCR amplification is carried out in duplicate by incubating them for 30 min at 60° C. with 20 μl of para-Bio-EG3-PDAM. After labeling, the DNA is purified on a QIAquick column (Nucleotide Removal Kit, Qiagen, Hilden, Germany) according to the protocol recommended by the supplier and the final eluate is collected in 50 μl of EB buffer (10 mM Tris-HCl, pH 8.5). Eighty-five (85) μl of the mixture of these eluates are denatured with 8.5 μl of reagent R4 (2N NaOH) for 5 min at room temperature, and the solution is then neutralized with 8.5 μl of reagent R5 (2N acetic acid). 850 μl of hybridization buffer (R6—10 mM Tris-HCl, pH 7.0, 0.2 g/l BND, 0.01 g/l Ciproflaxacin) and 85 μl of detection oligonucleotide (R7-4 mM sodium phosphate, 1 mM potassium phosphate, pH 7.0, 0.1% bovine serum albumin, 0.5% phenol) are added to the mixture. One hundred (100) μl of this preparation are deposited either on the positive control of a strip R1 provided with the kit (capture by a consensus sequence of the amplified gene), or on a streptavidin-coated Combiplate 8 plate (reference 95029263, Labsystem, Helsinki, Finland), or on a control Maxisorp plate (Nunc, Denmark).

In parallel, the same hybridization reaction is carried out on a ten-fold and one hundred-fold dilution, in EB buffer, of the DNA preparation in order to test the sensitivity of the technique.

EXAMPLE 36.2

Preparation of the Controls

Controls were simultaneously prepared in the following manner:

A—Comparison to the HLA-DR Kit:

Ten (10) μl of DNA obtained by PCR amplification, as described in Example 5, are incubated for 30 min at 60° C. with 20 μl of para-Bio-EG3-PDAM. After labeling, the DNA is purified on a QIAquick column, the final eluate is collected in a volume of 50 μl EB buffer. The 45 μl of eluate are denatured with 4.5 μl of reagent R4 for 5 min at room temperature, and the solution is neutralized with 4.5 μl of reagent R5. 450 μl of hybridization buffer R6 and 45 μl of detection oligonucleotide are added to the mixture. One hundred (100) μl of this preparation are deposited either on the positive control of a strip R1 provided with the kit (hybridization with a consensus sequence of the amplified gene), or on a streptavidin Combiplate 8 plate, or on a control Maxisorp plate.

B—Hybridization Performed on a DNA which does not Hybridize to the Specific Probe:

Ten (10) μl of DNA obtained by PCR amplification, as described in Example 5, are incubated for 30 min at 60° C. with 20 μl of para-Bio-EG3-PDAM. The sample is then treated in a manner identical to the procedure described above in Example A.

C—Control without DNA:

Ten (10) μl of reagent R6 (hybridization buffer) and 100 μl of reagent R7 (detection oligonucleotide) are deposited either on the positive control of a strip R1 provided with the kit, on a streptavidin plate, or on a Maxisorp-type control plate.

All the strips of the above protocols are incubated for one and a half hours at 37° C., and then washed with three times 100 μl of PBS Tween buffer (Color 0 HLA reagent) and then the presence of the specific detection probe is visualized by addition of 100 μl of chromogenic reagent (Color 2 reagent, PBS pH 7.0; 1% Tween, 0.2 g/l BND; 0.01 g/l Ciproflaxacin), incubated for 20 min in the dark, the reaction then being blocked with 50 μl of $H_2SO_4$ (1.8N Color 3 reagent). The absorbence of the reaction medium is then measured at 492 nm.

Results:

TABLE 20

Specific detection on a microplate of a DNA obtained from PCR

| Conditions | R1 strip HLA DR Kit (Specific capture) | Combiplate (Streptavidin) | Maxisorp (Control) |
|---|---|---|---|
| A - Labeled DNA - Ex. 36.1 | 1215 | 2160 | 16 |
| A - Labeled DNA (diluted 1/10) | NA | 900 | NA |
| A - Labeled DNA (diluted 1/100) | NA | 53 | NA |
| B - Control nonlabeled DNA - Ex. 36.2 A | 1153 | 40 | 17 |
| C - Control bacterial DNA - Ex. 36.2 B | 24 | 15 | NA |
| D - Control without DNA - Ex. 36.2 C | 13 | 12 | 17 |

The results of Table 20 indicate excellent amplification of the target which makes it possible to envisage a use in a diagnostic context. This example shows that the labeling on the phosphate groups allows the capture of DNA and does not prevent specific hybridization thereto.

EXAMPLE 37

Capture and Amplification of DNA Obtained from a Bacterial Lysate and Labeled with para-Bio-EG3-PDAM This example shows that it is possible to capture and to amplify a bacterial DNA using a capture based on the reactivity of the diazomethyl functional group on the phosphate of the nucleic acid.

In the present case, the nucleic acids contained in a bacterial lysate and labeled with para-Bio-EG3-PDAM are captured on streptavidin-coated magnetic beads. The use of magnetic beads makes it possible to immobilize the latter by magnetization during successive washings aimed at removing the cellular residues present in the reaction medium, it being necessary to remove these residues because they can inhibit the PCR amplification which is subsequently performed.

The amplification products were able to be analyzed by passage over DNA chips.

The bacterial DNA is obtained by lysing the cells contained in a *Mycobacterium tuberculosis* culture. The lysis is performed by mechanical lysis. More precisely, it is carried out by sonication, the treated liquid sample containing glass beads. Such a method is already indeed described by the applicant in its patent application WO-A-99/15621, as regards the beads, and in its patent application WO-A-00/60049, as regards the sonication. The sonication may also be carried out using a liquid bath.

However, other techniques, known to a person skilled in the art, may be used, such as those described in patent U.S. Pat. No. 5,902,746 and patent applications WO-A-98/54306 and WO-A-00/05338. All these Industrial Property titles belong to the applicant.

The bacterial DNA was quantified by Picogreen (P-7589; Molecular Probes, Eugene, Oreg., USA) according to the protocol described by the supplier, at a concentration of $10^7$ copies per μl.

Ten (10) μl of lysate are incubated in the presence of 20 μl of para-Bio-EG3-PDAM for 30 minutes at 60° C. In parallel, 10 μl of lysate are incubated in 20 μl of pure water (Sigma) under the same conditions.

The reaction medium is then purified on a QIAquick column (Nucleotide Removal Kit, Qiagen, Hilden, Germany). The purification protocol used is that recommended by the supplier. The final elution volume is 50 μl.

The labeled DNA fragments are then captured on Dynal magnetic beads (Dynabeads M-280 streptavidin; reference 112.05; Dynal Biotech ASA, Oslo, Norway), which are prepared according to the following protocol:

Ninety (90) μl of Dynal beads are washed twice with 200 μl of Free pure water (Sigma), and are then taken up in 200 μl of PEG buffer (0.1M $NaPO_4$, pH 7, 0.5M NaCl; 0.65% Tween 20; 0.14 ml Herring sperm DNA (reference 15634-017, GibcoBRL); 2% PEG 4000) and incubated for 30 min at 37° C. They are then washed twice with 200 μl 1×PBS buffer containing 0.5% Tween 20, and finally taken up in 90 μl of the same buffer.

Ten (10) μl of the labeled or nonlabeled DNA eluates are incubated for 5 min at room temperature with 40 μl of PEG buffer and 2.5 μl of the magnetic bead preparation described above.

The beads are then washed three times with 200 μl of 1×PBS buffer containing 0.5% Tween, taken up in 200 μl of water and incubated for 20 min at 60° C., and then washed again four times with 200 μl of PBS Tween The beads are finally taken up in 25 μl of water and a PCR is carried out according to the protocol described in Example 5. Two reaction controls are performed, one with 25 μl of pure water and the other with 2.5 μl of beads prepared and washed under the same conditions as the biological samples, and taken up in 25 μl of water.

Result:

The PCR products are then quantified by Picogreen (P-7589; Molecular Probes, Eugene, Oreg., USA) according to the protocol described by the supplier. This method is based on the use of a molecule (Picogreen) having the characteristic of becoming fluorescent only when it is positioned inside a DNA molecule (by becoming intercalated between the bases). Because of the very specific character of this intercalation, and because the fluorescent signal produced is directly proportional to the quantity of DNA present in the medium, it is possible to assay in this manner, very accurately, the concentration of nucleic acid present in a sample. The signal is then expressed in rfu (relative fluorescent unit).

Analysis of the results of PCR on gel shows the presence of a single specific band at the expected size in the samples prepared from genomic DNA labeled with para-Bio-EG3-PDAM. The bands are not detected when the PCR was carried out using a nonlabeled genomic DNA. Quantification of the DNA with Picogreen makes it possible to confirm the production of DNA from genomic DNA captured on beads.

TABLE 21

Quantification of the DNA produced by PCR, from a bacterial lysate, captured and purified by para-Bio-EG3-PDAM

| Conditions | rfu |
|---|---|
| Nonlabeled controls | 51 |
| Labeled DNAs | 170 |
| Background noise | 20 |

Analysis on a DNA chip, according to the protocol described in Example 8, makes it possible to confirm the specificity of the amplification as shown in Table 34 below.

TABLE 22

Specific detection of the target captured and purified with para-Bio-EG3-PDAM

|  | Homology | I (rfu) | B (rfu) | I/B |
|---|---|---|---|---|
| Sample | 98 | 11531 | 723 | 16 |

This example shows that it is possible to prepare a biological sample so as to amplify the nucleic acid which it contains, using a capture technique based on the reactivity of the diazomethyl functional group on the phosphate groups thereof.

EXAMPLE 38

Successive Amplification of Two Genes from a Bacterial DNA Captured on a Solid Support This example shows that it is possible to amplify several times and on different targets a DNA captured by virtue of the reactivity of the diazomethyl functional group on the phosphate groups thereof.

In the present case, the nucleic acids, contained in a bacterial lysate and labeled with para-Bio-EG3-PDAM, are captured on streptavidin-coated magnetic beads. The use of magnetic beads makes it possible to preserve the latter by magnetization during successive washings aimed at removing the cellular residues present in the reaction medium, it being necessary for these residues to be removed because they can inhibit the PCR amplifications which will be subsequently performed. These amplifications will take place on two different genes present in the genomic DNA, designated by the names 16S and rpoB respectively. These two genes are then analyzed using DNA chips.

The bacterial DNA is obtained by lysing the cells contained in a Mycobacterium tuberculosis culture, according to the protocol already described in Example 37. The bacterial DNA was quantified with Picogreen according to the protocol described by the supplier, at a concentration of $10^7$ copies per µl.

Ten (10) µl of lysate are incubated in the presence of 20 µl of para-Bio-EG3-PDAM for 30 minutes at 60° C. In parallel, 10 µl of lysate are incubated in 20 µl of pure water (Sigma) under the same conditions.

The reaction medium is then purified on a QIAquick column (Nucleotide Removal Kit, Qiagen, Hilden, Germany). The purification protocol used is that recommended by the supplier. The final elution volume is 50 µl.

The labeled DNA fragments are then captured on Dynal magnetic beads, which are prepared according to the following protocol:

Ninety (90) µl of Dynal beads are washed twice with 200 µl of Free pure water (Sigma), and are then taken up in 200 µl of PEG buffer (0.1M NaPO$_4$, pH 7, 0.5M NaCl; 0.65% Tween 20; 0.14 ml salmon sperm DNA (GibcoBRL); 2% PEG 4000) and incubated for 30 min at 37° C. They are then washed twice with 200 µl 1×PBS buffer containing 0.5% Tween 20, and finally taken up in 90 µl of the same buffer.

Ten (10) µl of the labeled or nonlabeled DNA eluates are incubated for 5 min at room temperature with 40 µl of PEG buffer and 2.5 µl of the magnetic bead preparation described above.

The beads are then washed three times with 200 µl of 1×PBS buffer containing 0.5% Tween, taken up in 200 µl of water and incubated for 20 min at 60° C., and then washed again four times with 200 µl of PBS Tween. The beads are finally taken up in 25 µl of water and a PCR is carried out according to the protocol described in Example 5. Two reaction controls are performed, one with 25 µl of pure water (Sigma) and the other with 2.5 µl of beads prepared and washed under the same conditions as the biological samples, and taken up in 25 µl of water.

After amplification, the reaction medium is collected, and the beads are separated and washed with 150 µl of 1×PBS containing 0.5% Tween, and then resuspended in 25 µl of pure water (Sigma). Another amplification is performed on the beads, but in the presence of primers intended to amplify the rpoB gene.

Control amplifications performed using noncaptured genomic DNA are performed in parallel on the two amplification systems (rpoB and 16S).

Result:

The PCR products obtained are then analyzed using DNA chips according to the protocol described in Example 8.

TABLE 23

Analysis on DNA chips of the DNA amplicons obtained from PCRs amplified successively or otherwise

| Conditions | | Homology (%) | I (rfu) | B (rfu) | I/B |
|---|---|---|---|---|---|
| Control PCR 16S | 16S | 96 | 4662 | 387 | 12 |
| Results on rpoB sequence | RpoB | 23 | 237 | 358 | 1 |
| Control PCR rpoB | RpoB | 98 | 5438 | 397 | 14 |
| Results on 16S sequence | 16S | 17 | 183 | 391 | 1 |
| PCR 16S on beads | 16S | 98 | 2726 | 534 | 5 |
| Results on rpoB sequence | RpoB | 8 | 161 | 480 | <1 |
| PCR rpoB on washed beads | RpoB | 97 | 3205 | 349 | 9 |
| Results on 16S sequence | 16S | 14 | 84 | 358 | <1 |

Analysis of the results of PCR on gel shows the presence of a single specific band at the expected size in the samples prepared from genomic DNA labeled with para-Bio-EG3-PDAM. The bands are not detected when the PCR was carried out using nonlabeled genomic DNA.

Analysis using a DNA chip, as presented in Table 23 above, makes it possible to confirm the specificity of the two successive amplifications, and therefore the capacity to carry out a successive amplification of several genes from DNA immobilized on a solid support, this making it possible to avoid the development of multiplex systems, which often substantially reduce the sensitivity and efficiency of nucleic acid amplifications.

EXAMPLE 39

Capture and Amplification of DNA on a Nylon Membrane Carrying Diazomethyl Groups A Nylon membrane activated so as to carry diazomethyl groups was used to capture bacterial DNA, with the aim of amplifying it by PCR.

EXAMPLE 39.1
Modification of the Biodyne C Filter:
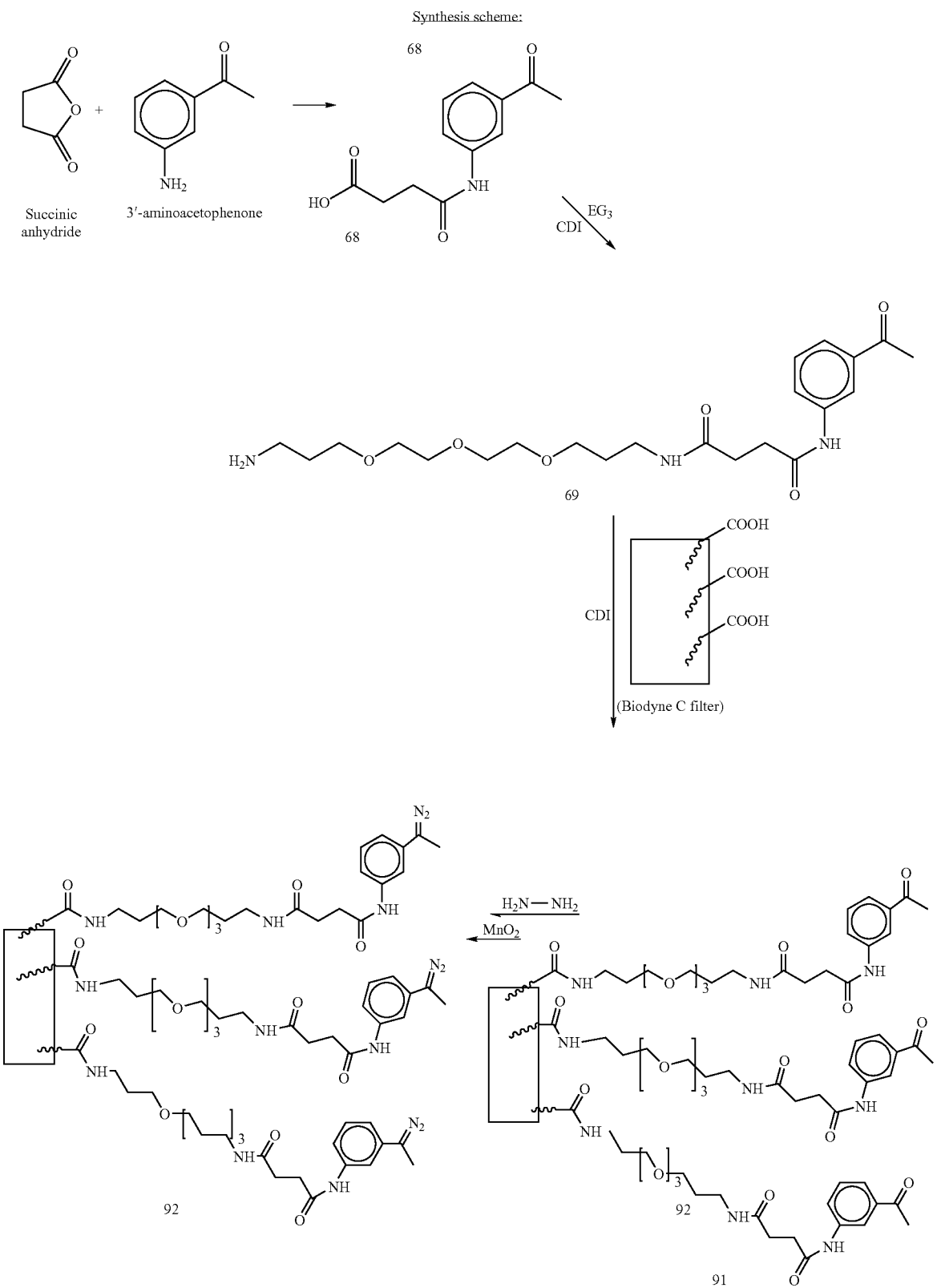

Compound 68:

3'-Aminoacetophenone (14.5 g, 107 mmol) is solubilized in 50 ml of anhydrous DMF. Succinic anhydride (10.7 g, 107 mmol) is added and the mixture is kept stirred under argon and at room temperature. After 6 h, the solution is concentrated under vacuum and 50 ml of methanol are added. The precipitate obtained is filtered and washed with methanol and ether. 19.4 g (81%) of product 68 are thus obtained in the form of an off-white powder.

$^1$H NMR (200 MHz, DMSO-$d_6$): δ=2.5–2.6 (m, 7H); 7.45 (t, 1H); 7.64 (d, 1H); 7.83 (d, 1H); 8.19 (s, 1H); 10.16 (s, 1H); 12.12 (s, 1H).

Compound 69:

5.07 g (22 mmol) of compound 68 are solubilized in 10 ml of anhydrous DMF, under argon. The solution is placed on ice and 5.00 g (32 mmol) of carbonyldiimidazole are added. After 20 min, 20 ml (94.6 mmol) of 4,7,10-trioxatridecanediamine ($EG_3$) are slowly added. After 3 h of reaction at room temperature, the DMF is evaporated and the residue is taken up in 100 ml of $CH_2Cl_2$. Extractions are carried out with saturated $NaHCO_3$ and $H_2O$, after which the organic phase is dried with anhydrous $Na_2SO_4$ and the solvent evaporated. 4.34 g (46%) of product 69 are thus obtained.

$^1$H NMR (200 MHz, DMSO-$d_6$) δ=1.59 (m, 2H); 1.87 (m, 2H); 2.16 (s, 3H); 2.40 (m, 2H); 2.55 (m, 2H); 3.08 (m, 2H); 3.45 (m, 16H); 7.30 (t, 1H); 7.42 (d, 1H); 7.70 (d, 1H); 7.83 (t, 1H); 7.97 (s, 1H); 10.00 (s, 1H).

Compound 91:

A 4 cm$^2$ rectangle is cut out on a sheet of Biodyne C filter (reference 60314; Pall Gelman Laboratory; Ann Arbor; Mich.; USA), introduced into a bottle and brought into contact with 0.97 g (6 mmol) of carbonyldiimidazole (CDI) in 3 ml of anhydrous DMF, on ice, under argon and with vigorous stirring. After 20 min, the solution is removed and the filter washed with DMF. A quantity of 0.53 g of product 68 (1 mmol) in 3 ml of anhydrous DMF is then added, and the reaction occurs overnight at room temperature. The solution is then removed and the filter is rinsed with ethanol, dried under vacuum and kept under argon.

Compound 92:

The modified filter 91 is placed in a solution of 97 ml of hydrazine hydrate (2 mmol) in 4 ml of absolute ethanol. The solution is refluxed for 5 h. After having allowed it to cool, the filter is washed with $H_2O$, ethanol and ether, dried under vacuum and placed under argon. Next, 4 ml of anhydrous DMF and 86 mg of $MnO_2$ (1 mmol) are added, and the mixture is allowed to react, with vigorous stirring. After 20 min, the solution is discarded, and the filter is rinsed with DMF and ether. The diazomethyl-modified filter 92 is stored under argon, at a temperature of –19 to –31° C.

EXAMPLE 39.2

Biological Tests

The activated membrane is cut into small fragments of 2 mm$^2$ which will be incubated for 30 minutes at room temperature in 25 µl of *Mycobacterium tuberculosis* bacterial lysate, prepared by mechanical lysis, using the same technique and the same final concentration as in Example 37, and 375 µl of pure water (Sigma).

The membrane is then placed at 65° C. for 60 min in 100 ml of washing buffer (5% Formamide (Sigma), 1×SSPE (Perbio), 0.01% Triton X-100) so as to remove the nonspecific nucleic acids adsorbed onto the membrane, and then the latter is stored in 1 ml of pure water before amplification.

The PCR is carried out as described in paragraph 5.1, the reaction volume being adjusted with a sufficient quantity of pure water.

In parallel, controls are made according to the same procedure with membranes which cannot covalently bind nucleic acids:

nonmodified Biodyne C membrane (membrane A),

Biodyne membrane chemically modified according to the procedure described, but not treated with anhydrous DMF and $MnO_2$; this control makes it possible to verify the behavior of the membrane in the absence of diazomethyl groups (membrane B), and Biodyne C membrane which has not been modified, but has been treated for 20 min, with vigorous stirring, with anhydrous DMF and $MnO_2$, this control making it possible to verify that the latter step does not modify the adsorption of DNA to the membrane (membrane C).

To check for the absence of inhibition of PCR caused by the treatment of the membranes, another fragment of the membranes A, B and C is amplified simultaneously with 25 µl of bacterial lysate (tubes A', B' and C').

The PCR products are then quantified with Picogreen according to the protocol described by the supplier.

Result:

TABLE 24

Quantification of the DNA obtained by PCR from DNA of bacterial lysate captured on solid support

| Tests performed | Signal (rfu) |
| --- | --- |
| Modified membrane | 111 |
| Nonmodified membrane (A) | 18 |
| Nonmodified membrane, coamplified with 25 µl of bacterial lysate (A') | 260 |
| Nonactivated modified membrane (B) | 26 |
| Nonactivated modified membrane, coamplified with 25 µl of bacterial lysate (B') | 264 |
| Nonmodified membrane which has undergone activation (C) | 21 |
| Nonmodified membrane which has undergone activation, coamplified with 25 µl of bacterial lysate (C') | 268 |

These results of Table 24 indicate that it is possible to covalently capture on a solid support nucleic acids, obtained from a lysate, by virtue of the diazomethyl chemistry. The amplification observed is not due to nonspecific adsorption of the DNA to the membrane. On the other hand, it is observed, with the controls performed with the PCRs, that the membranes do not cause inhibition of the amplification reaction.

In order to check the nature of the amplified product on the membrane, the amplification product was analyzed by passing over a DNA chip, according to the protocol described above.

The invention claimed is:

1. A method for fragmenting and labeling a single- or double-stranded deoxyribonucleic acid (DNA) comprising the following steps:

fragmenting the DNA by creating at least one abasic site on said DNA, attaching a marker to at least one of the fragments by means of a labeling reagent, said reagent covalently and predominantly coupling to at least one phosphate of said fragment.

2. The method as claimed by claim 1, wherein the fragmentation and labeling are carried out in two steps.

3. The method as claimed in claim 1, wherein the fragmentation and labeling are carried out in one step.

4. The method as claimed in claim 1, wherein the abasic site is generated by the action of an acidic aqueous medium.

5. The method as claimed in claim 4, wherein the pH of the acidic medium is less than 5.

6. The method as claimed in claim 5, wherein the acidic aqueous medium is a sodium formate buffer at a pH of about 3.

7. The method as claimed in claim 1, wherein the DNA contains at least one modified base capable of generating an abasic site.

8. The method as claimed in claim 7, wherein the modified base capable of generating an abasic site is chosen from 8-bromopurine derivatives.

9. The method as claimed in claim 1, wherein the abasic site is generated by an alkylating agent or an oxidizing agent.

10. The method for labeling and fragmenting as claimed in claim 1, wherein the labeling reagent comprises, as reactive functional group, a motif chosen from the following compounds: diazomethyl; alkyl halide; nitrosourea; spirocyclopropane; aziridine; epoxide; and trifluoromethanesulfonates.

11. The method as claimed in claim 10, wherein said labeling reagent is 5-(bromomethyl)fluorescein.

12. The method as claimed in claim 10, wherein the labeling reagent is chosen from the compounds of formula (I):

in which
R$^1$ represents H or an alkyl, substituted alkyl, aryl or substituted aryl group, and
Z comprises a detectable marker.

13. The method as claimed in claim 12, wherein Z is:

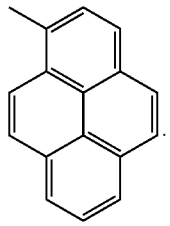

14. The method as claimed in claim 12, wherein the labeling reagent is chosen from the compounds of formula (2):

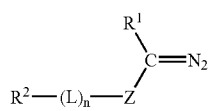

in which:
R$^1$ represents H or an alkyl, aryl or substituted aryl group,
R$^2$ is a detectable marker,
L is a linking arm containing a linear succession of at least two covalent bonds and n is equal to 0 or 1, and
Z is chosen from:

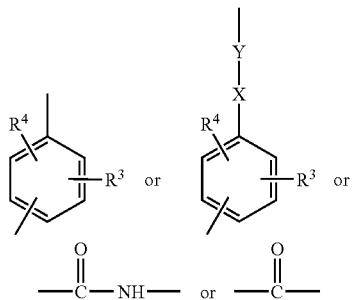

in which:
R$^3$ and R$^1$ represent independently of each other: H, NO$_2$, Cl, Br, F, I, OR, SR, NR$_2$, R, NHCOR, CONHR, or COOR with R=alkyl or aryl, and
—Y—X— represents —CONH—, —NHCO—, —CH$_2$O— or —CH$_2$S—.

15. The method as claimed in claim 14, wherein the labeling reagent has the formula (3):

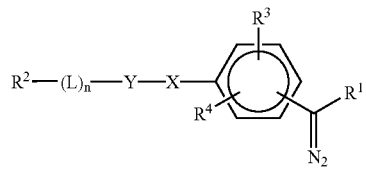

in which:
R$_1$ represents H or an alkyl, aryl or substituted aryl group,
R$_2$ represents a detectable marker,
L is a linking arm containing a linear succession of at least 2 covalent bonds and n is an integer equal to 0 or 1,
R$_3$ and R$_4$ represent independently of each other: H, NO$_2$, Cl, Br, F, I, OR, SR, NR$_2$, R, NHCOR, CONHR, or COOR with R=alkyl or aryl, and
—Y—X— represents —CONH—, —NHCO—, —CH$_2$O— or —CH$_2$S—.

16. The method as claimed in claim 14, wherein R$^2$ is a fluorescent compound or a hapten.

17. The method as claimed in claim 10, wherein said labeling reagent is soluble in a water-miscible solvent.

18. A method for detecting a single- or double-stranded target deoxyribonucleic acid (DNA) comprising the following steps:
fragmenting and labeling said DNAs according to a method as claimed in claim 1,
under hybridization conditions, contacting the labeled fragments to at least one nucleic acid probe which is sufficiently specific for the target nucleic acid, and
detecting any hybrid formed using the marker.

19. The method for detecting a double-stranded target deoxyribonucleic acid (DNA) as claimed in claim 18, comprising, in addition, a denaturation step after the fragmentation and the labeling.

20. The method as claimed in claim 19, wherein the fragmentation, labeling and denaturation are carried out in a single step.

21. A method for detecting a target nucleic acid comprising the following steps:
  enzymatically amplifying the target nucleic acid in order to generate a multitude of double-stranded DNA amplicons,
  fragmenting and labeling said DNA amplicons according to a method as claimed in claim 1,
  under hybridization conditions, contacting the labeled fragments to at least one nucleic acid probe which is sufficiently specific for the target nucleic acid, and
  detecting any hybrid formed using the marker.

22. The method as claimed in claim 21, comprising, in addition, a denaturation step after the fragmentation and labeling step.

23. A method as claimed in claim 22, wherein the fragmentation, labeling and denaturation are carried out in a single step.

24. A method for detecting a polymorphism distributed in predetermined or nonpredetermined positions of a target nucleic acid by the presence of a plurality of deletions and/or insertions and/or mutations in the sequence of said target nucleic acid relative to a so-called reference sequence, comprising the following steps:
  having a target DNA containing the entire polymorphism to be studied, said DNA being optionally generated by an enzymatic amplification technique,
  fragmenting and labeling said DNA by a method as claimed in claim 1,
  under hybridization conditions, contacting said fragments to a plurality of nucleic acid probes termed capture probes, the plurality of capture probes being attached to a solid support and the plurality of capture probes covering in its entirety at least the polymorphism to be studied, and
  detecting any hybrids formed between the labeled fragments and at least part of the nucleic acid probes using the marker and deducing therefrom the polymorphism of the target DNA.

25. The method as claimed in claim 24, comprising, in addition, a denaturation step after the fragmentation and labeling step.

26. The method as claimed in claim 25, wherein the fragmentation, labelings and denaturation are carried out in a single step.

27. The method as claimed in claim 24, wherein the solid support contains at least ten (10) nucleic acid probes of different sequences.

28. The method as claimed in claim 4, wherein the pH of the acidic medium is less than 4.

29. The method as claimed in claim 24, wherein the solid support contains at least four hundred (400) nucleic acid probes of different sequences.

30. The method as claimed in claim 24, wherein the solid support contains at least one thousand (1000) nucleic acid probes of different sequences.

31. A method for detecting a target nucleic acid, comprising:
  fragmenting and labeling a deoxyribonucleic acid (DNA) by a method according to claim 1, wherein the fragment that is attached to the marker is sufficiently specific for the target nucleic acid,
  under hybridization conditions, contacting the fragment that is attached to the marker with potential target nucleic acid, and
  detecting any hybrid formed using the marker.

* * * * *